(12) United States Patent
Svedman

(10) Patent No.: US 6,855,133 B2
(45) Date of Patent: Feb. 15, 2005

(54) TRANSDERMAL PERFUSION OF FLUIDS

(75) Inventor: Pal Svedman, Malmo (SE)

(73) Assignee: Principal AB, Malmo (SE)

(*) Notice: Subject to any disclaimer, the term of this patent is extended or adjusted under 35 U.S.C. 154(b) by 104 days.

(21) Appl. No.: 10/115,472

(22) Filed: Apr. 2, 2002

(65) Prior Publication Data

US 2002/0115967 A1 Aug. 22, 2002

Related U.S. Application Data

(63) Continuation of application No. 09/538,372, filed on Mar. 29, 2000, now Pat. No. 6,436,078, which is a division of application No. 08/350,488, filed on Dec. 6, 1994, now Pat. No. 6,048,337, which is a continuation-in-part of application No. 08/084,267, filed on Nov. 23, 1993, now Pat. No. 5,441,490.

(30) Foreign Application Priority Data

Jan. 7, 1992 (WO) .............................. PCT/EP/92/00029

(51) Int. Cl.[7] .............................................. A61M 35/00
(52) U.S. Cl. ...................................... 604/290; 604/289
(58) Field of Search ................................. 600/573, 576, 600/578, 583, 538; 606/181, 182; 604/289, 290, 19, 22, 36, 46, 48, 500, 304–308, 311, 313, 315, 316; 424/443–449; 128/573, 578, 579

(56) References Cited

U.S. PATENT DOCUMENTS 5,441,490 A * 8/1995 Svedman ..................... 604/289
5,857,983 A * 1/1999 Douglas et al. ............. 600/583
6,048,337 A * 4/2000 Svedman ..................... 604/313
6,436,078 B1 * 8/2002 Svedman ..................... 604/313

FOREIGN PATENT DOCUMENTS

WO  WO9211879  * 7/1992
WO  WO9515783  * 6/1995

* cited by examiner

Primary Examiner—Kim M. Lewis
(74) Attorney, Agent, or Firm—Dorsey & Whitney LLP; David J. Brezner

(57) ABSTRACT

A housing is secured to an area of skin to allow suction to be applied to a local area of skin through an aperture. After formation of a suction blister, a blade is actuated to sever a suction cup thereby detaching the means for creating suction at the aperture and at the same time removing the roof of the suction blister to expose an area of dermis from which the skin's epidermis has been removed.

A rotatable portion of the apparatus is then moved into a position in which a port communicates with a compartment within the rotatable portion. The compartment may contain a reservoir of fluid substance to be transdermally absorbed or may contain means for taking a sample of exudate produced at the exposed dermis. A modified apparatus has means for applying suction to the exposed dermis to enhance the rate at which exudate is formed and for handling a sample of exudate for analysis. Transdermal delivery and sampling are thereby achieved non-invasively and without the impediment of the skin's epidermis.

1 Claim, 48 Drawing Sheets

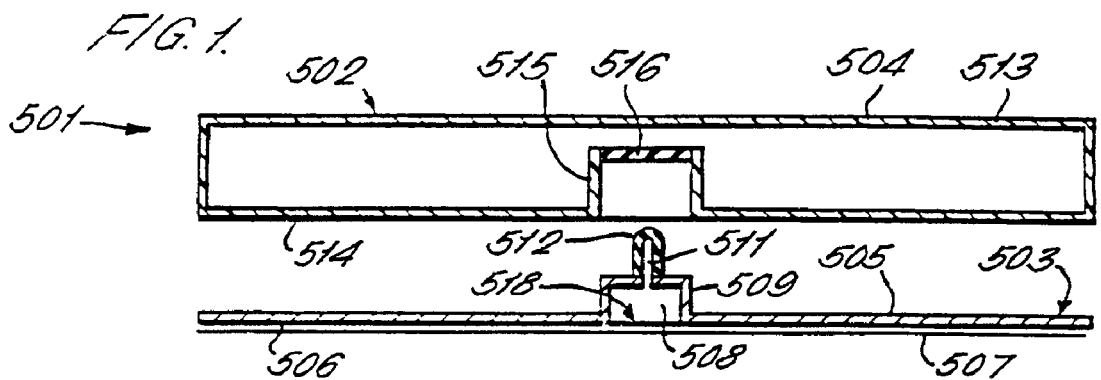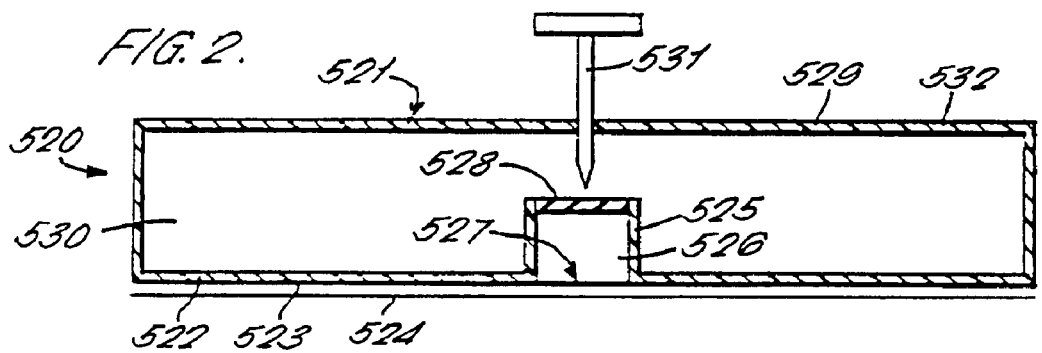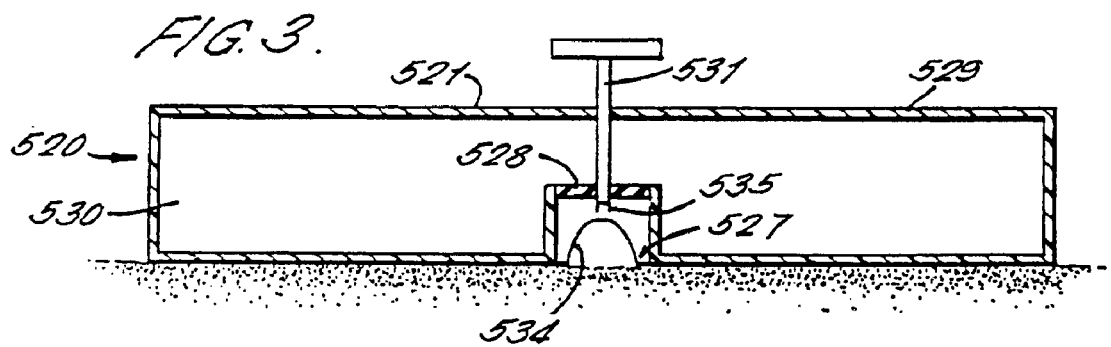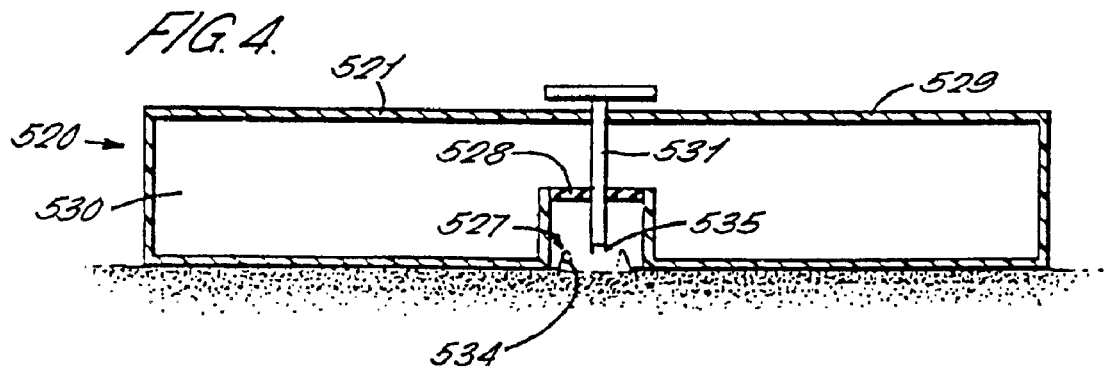

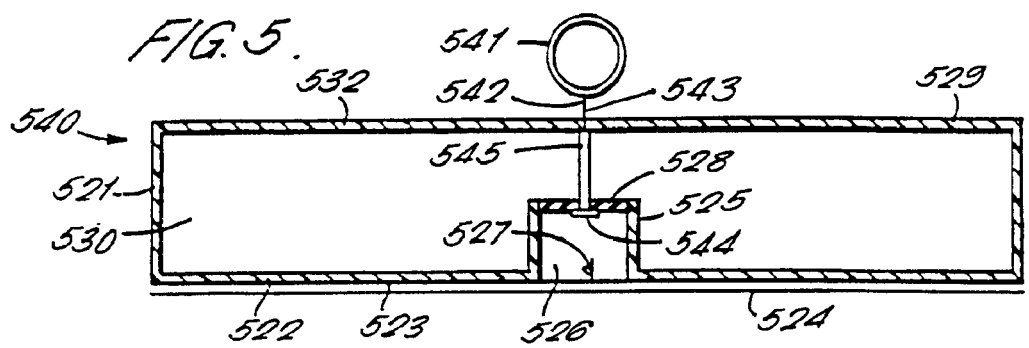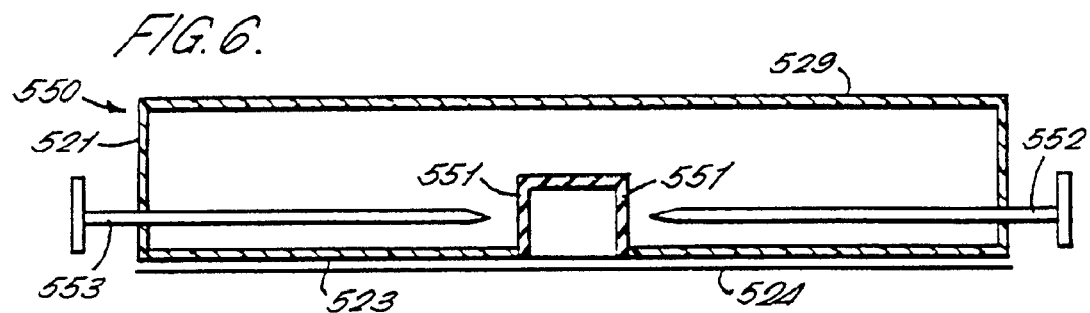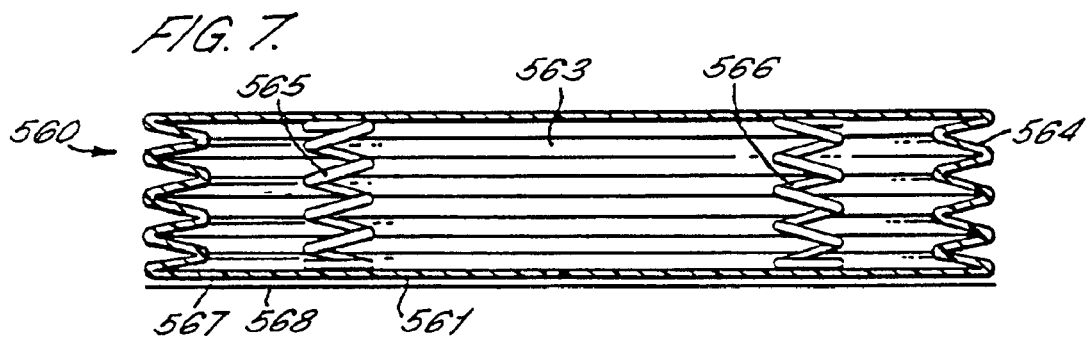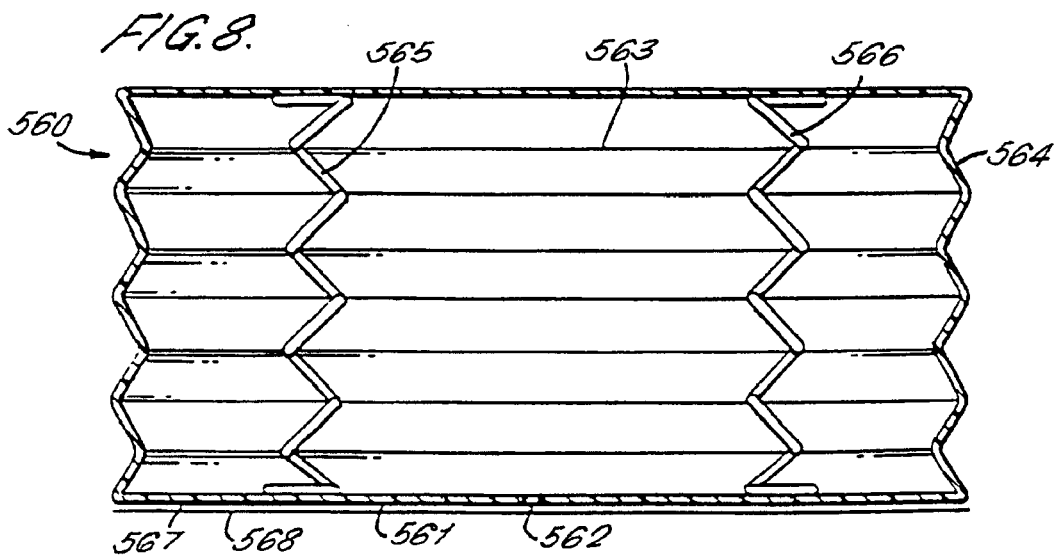

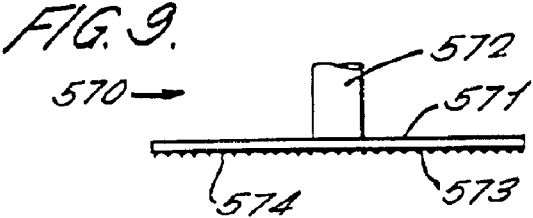
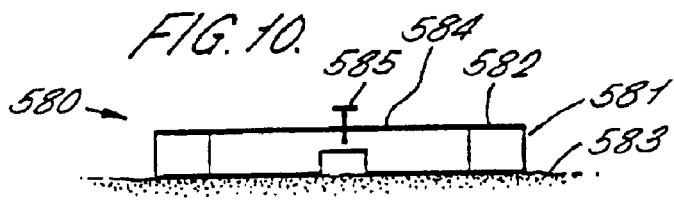
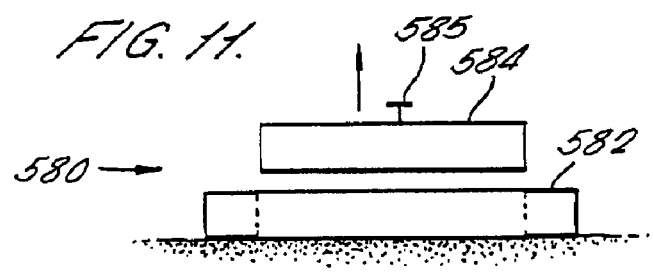
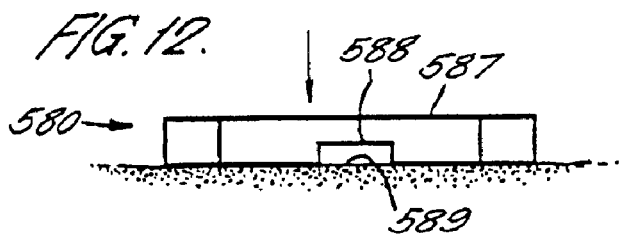
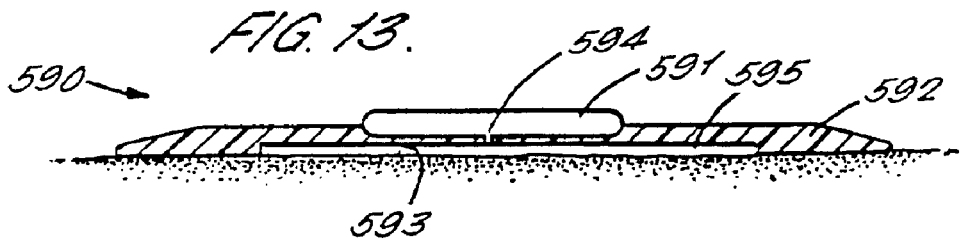

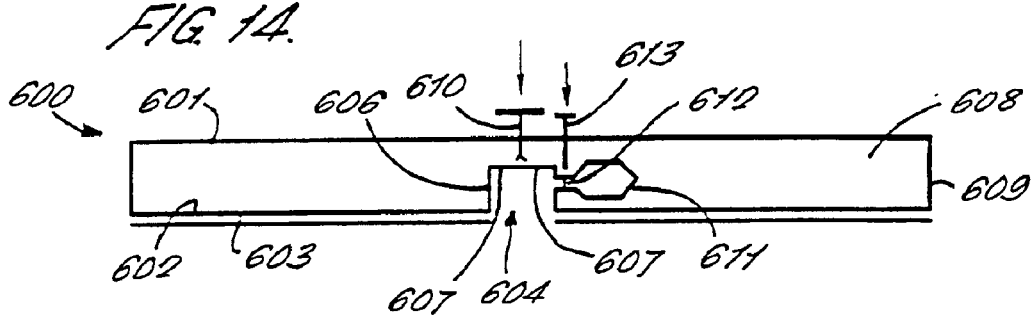
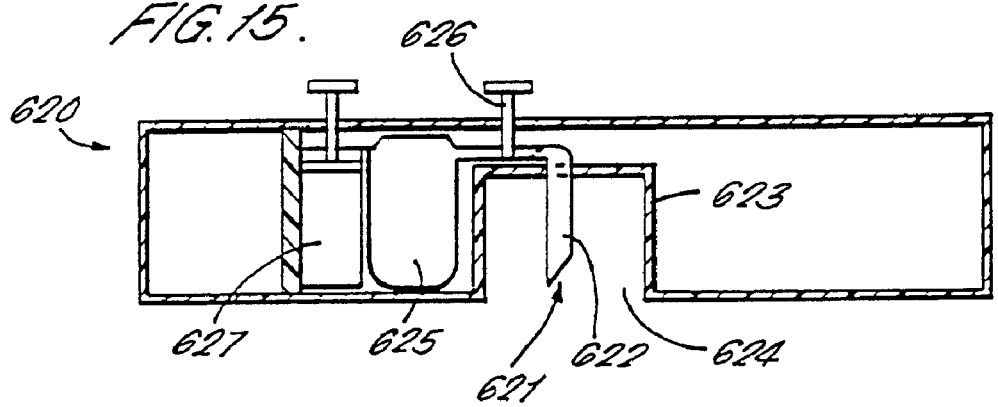
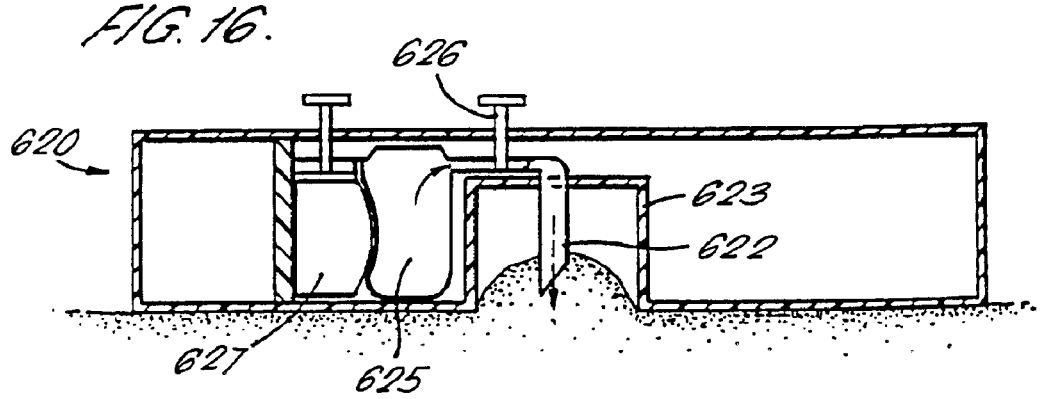

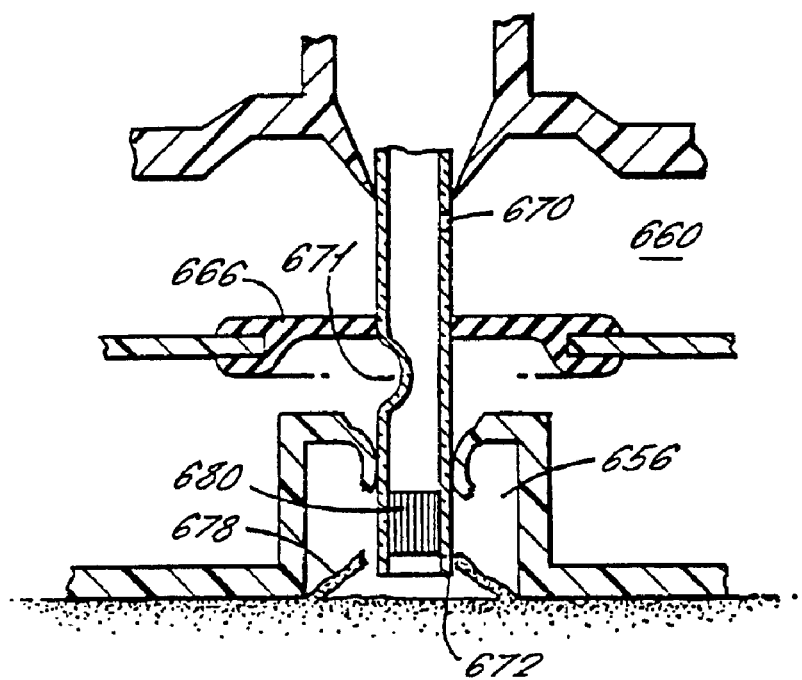
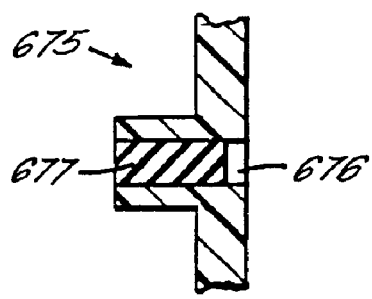
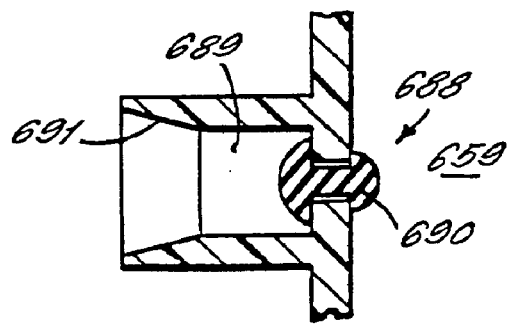
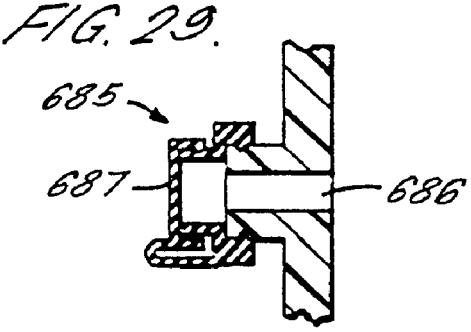

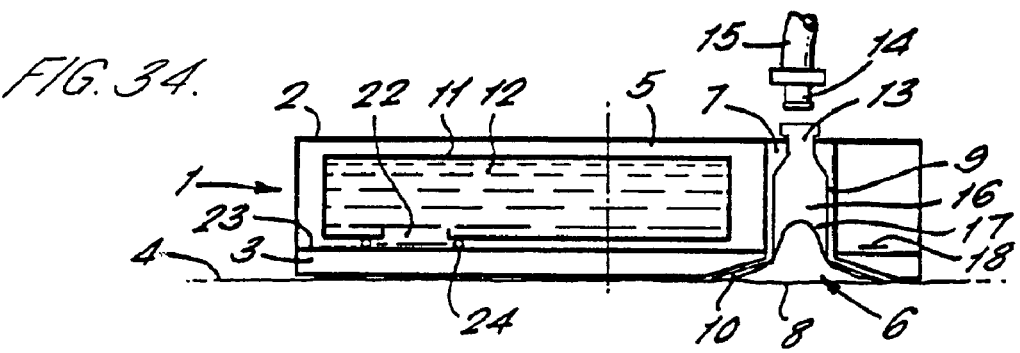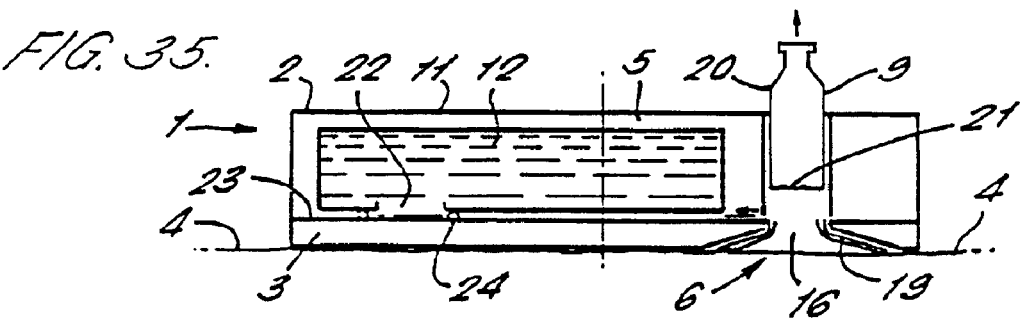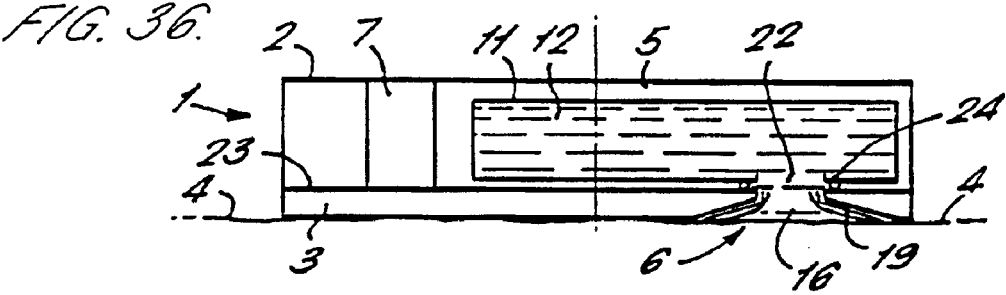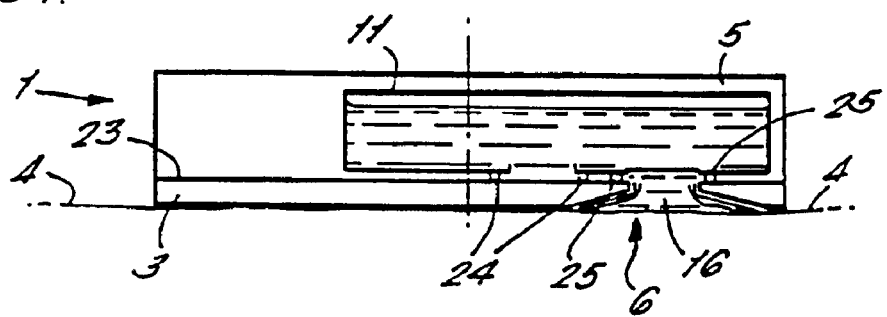

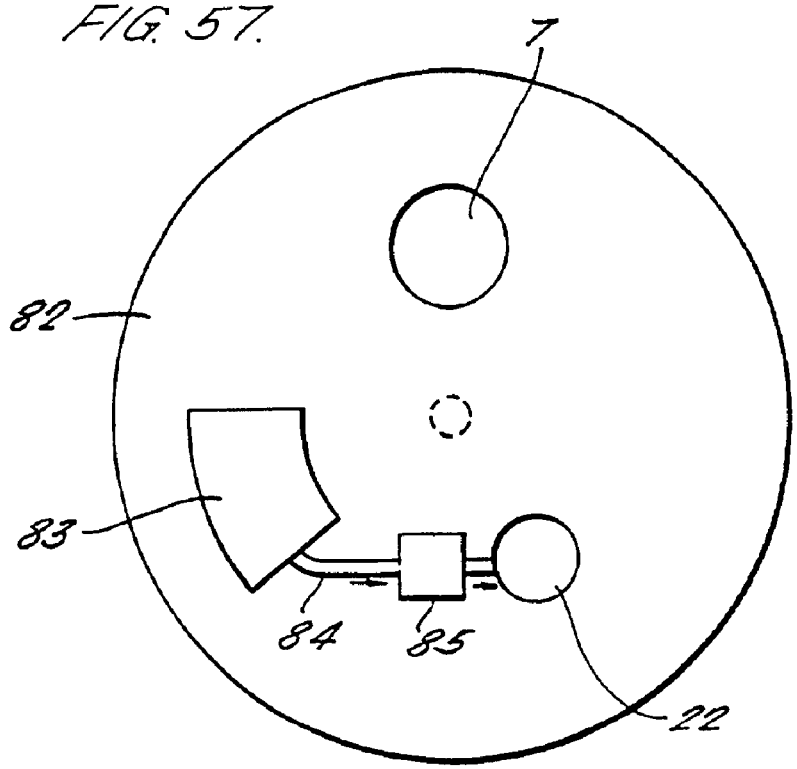
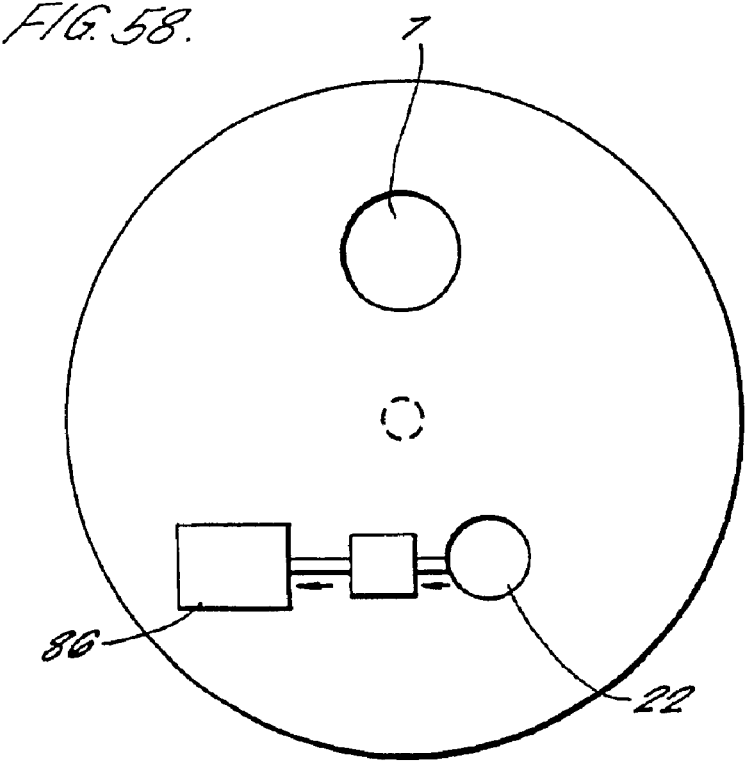

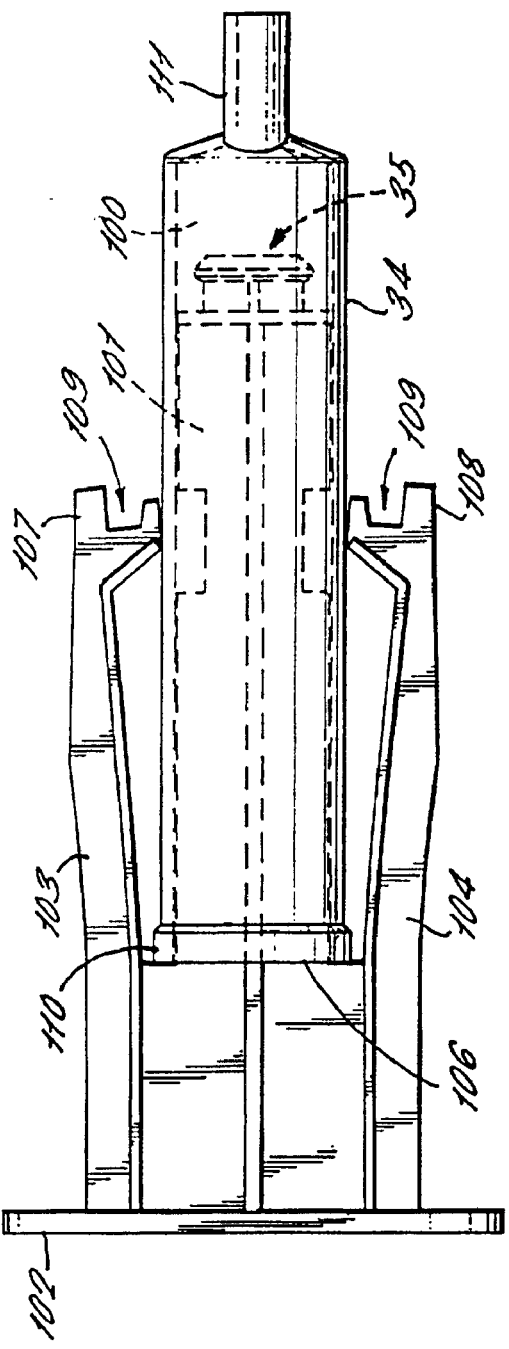
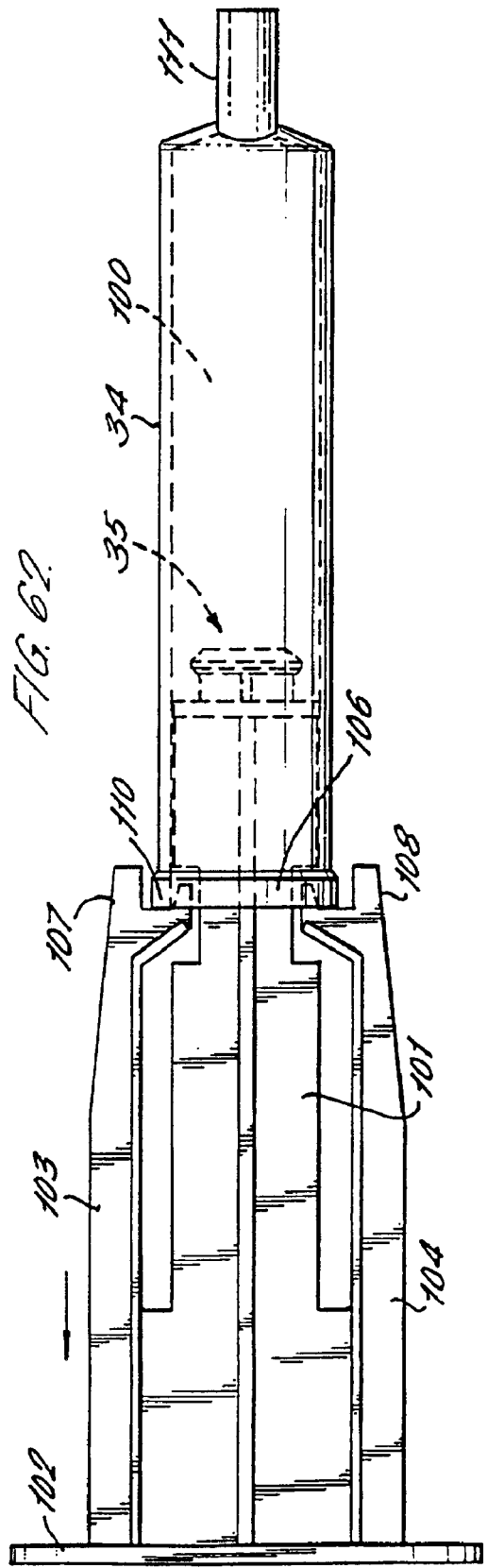

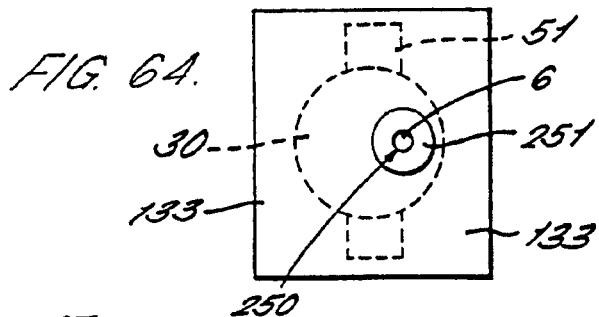
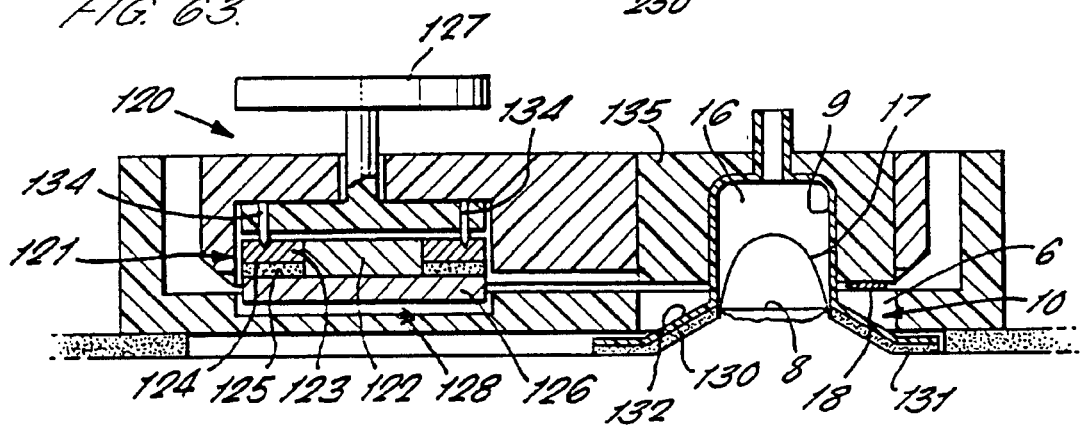
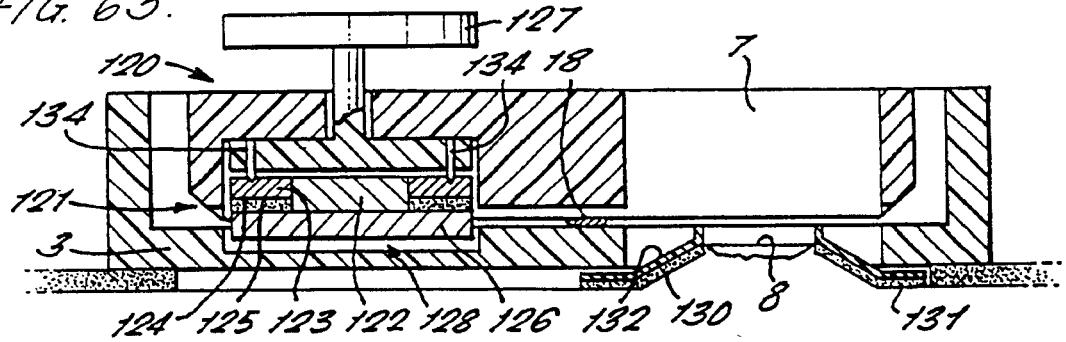
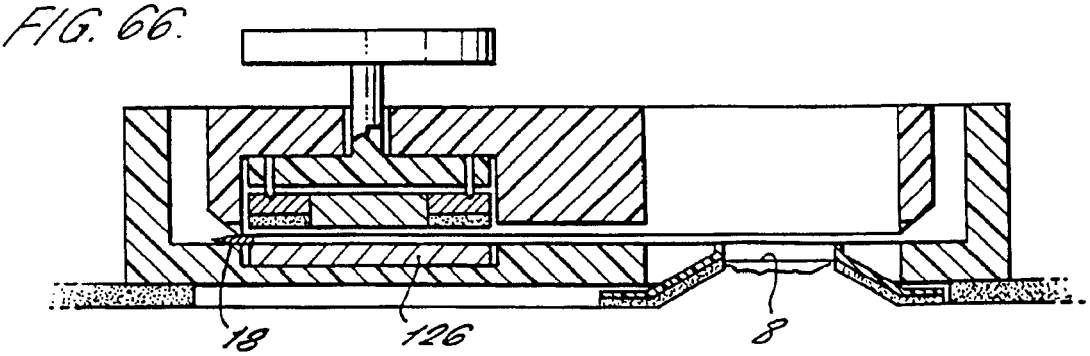

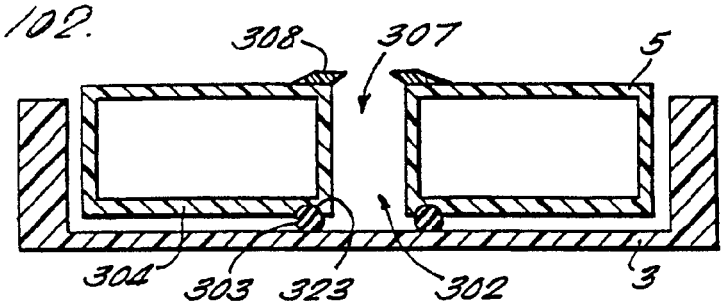
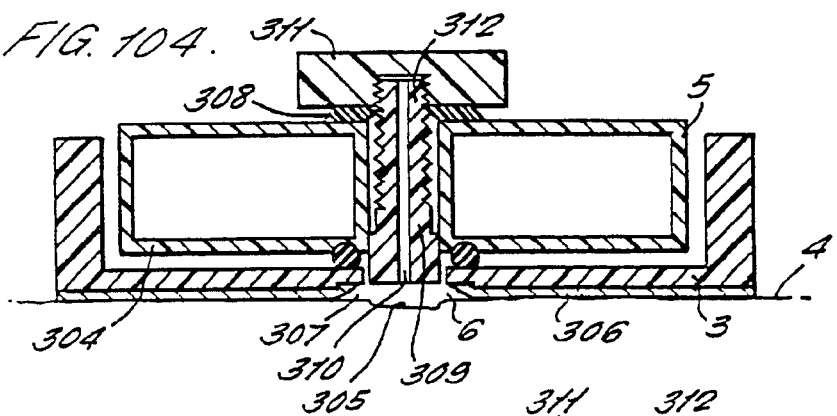
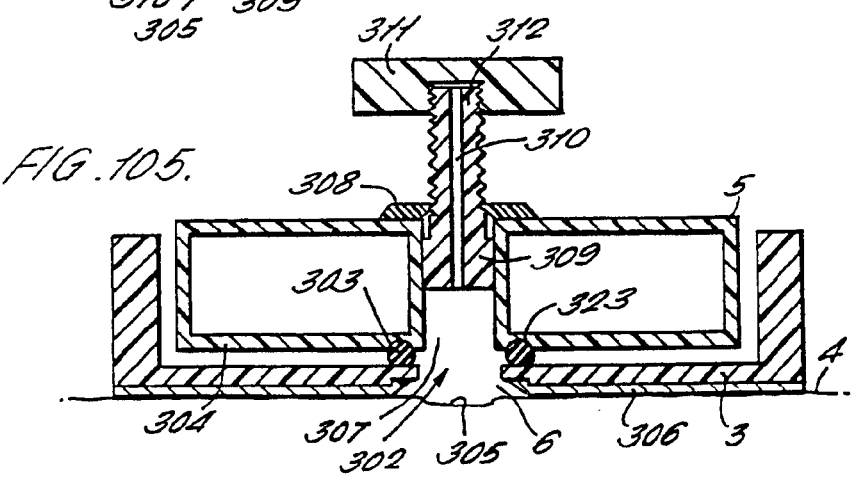
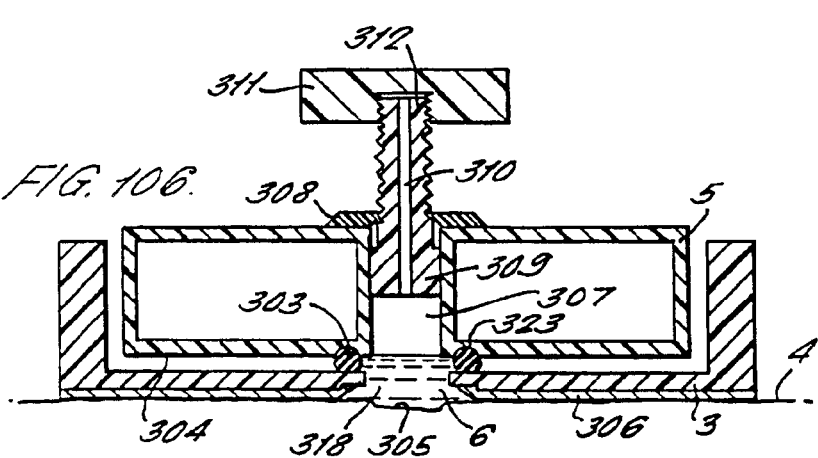

TRANSDERMAL PERFUSION OF FLUIDS

This application is a continuation of U.S. patent application Ser. No. 09/538,372, filed 29 Mar. 2000, now U.S. Pat. No. 6,436,078 which is a divisional of application Ser. No. 08/350,488 filed 6 Dec. 1994, now U.S. Pat. No. 6,048,337 which is a continuation-in-part of application Ser. No. 08/084,267 now U.S. Pat. No. 5,441,490 "Transdermal Perfusion of Fluids" filed Nov. 23, 1993 pursant to International Application PCT/EP92/00029 filed Jan. 7, 1992. The contents of said application are incorporated by reference into the present application.

This invention relates to transdermal perfusion of fluids through the skin of the human or animal body and in particular but not exclusively to apparatus for de-epithelialising the skin by the suction blister method to enable perfusion to take place directly via the dermis layer. Aspects of the invention also relate to perfusion of body fluids through the skin for external collection and sampling.

The transdermal perfusion of fluids for drug delivery has in recent years become an increasingly favoured alternative to intravenous or oral drug delivery. The technique has however found limited application because the epidermis (outer skin layer) forms an effective barrier to the perfusion of substances and in particular drugs having a large molecular size.

In its simplest form, transdermal absorption has been achieved using skin patches in which a substance in a fluid contacting the skin is absorbed by diffusion whereby the random molecular motion tends to equilibrate the concentration of the substance across the membrane provided by the skin.

Various techniques have been proposed to enhance transdermal delivery including iontophoresis and the use of chemical enhancers. (Chemical enhancement is for example described in Int. J. Pharm. 1989, 49, 199–201 and Iontophoresis in J. Pharm. Sci. 1990, 79, 490–93). Mechanical stimulation for instance by ultrasound has also been used to enhance transdermal delivery. (Use of ultrasound is for example described in Pharm. Res. 1992, 9, 559–564). There remains a need however to provide a more effective transdermal technique particularly for peptides and hormones which hitherto have not been capable of being transdermally administered.

It is also known from U.S. Pat. No. 3,486,504 to provide a resilient housing with an air release valve which can be held against an infected skin area by suction. A medicated and absorbent dressing within the housing is thereby held in contact with the skin.

It is also known in the field of skin grafting to remove portions of the epidermis to expose the dermis layer of skin by the application of suction in which a partial vacuum of about 200 mm of mercury applied for a period of two or three hours has the effect of delaminating the epidermis from the dermis to form a blister containing a clear blister fluid. (A suction blister method is for example described by Kiistala U, "The suction blister method for the in vivo separation of epidermis from dermis in human skin", Thesis, Univ of Helsinki, 1976). Such blisters have a roof which comprises the epidermis and can easily be removed for skin grafting.

According to one aspect of the present invention there is disclosed apparatus for use in transdermal administration of fluids through the skin of a human or animal body, the apparatus comprising a housing attachable to the body, the housing having a contact surface which in use is held in contact with a portion of skin by an adhesive layer, the housing defining a chamber and the contact surface defining an aperture communicating with the chamber, the apparatus further comprising suction means operable during a preparatory phase of operation of the apparatus to apply suction to the skin at a treatment site which is accessible via the aperture such that an area of the skin's epidermis at the treatment site is detached from the skin's underlying dermis, means for disrupting the detached area of epidermis such that the dermis is exposed within the chamber, and fluid supply means operable during a perfusion phase of operation of the apparatus to supply fluid to the chamber such that fluid in the chamber may be absorbed by the dermis without intervention of the epidermis.

The process of removing a portion of epidermis, also referred to as an epithelial layer, from the underlying intact dermis is referred to herein as a de-epithelialising method and the resulting area of skin from which the epidermis has been removed will be referred to as a de-epithelialised erosion or lesion. Such an erosion formed by splitting the epidermis from the dermis by suctioning followed by disruption of the detached epidermis allows a unique form of access to the body. The suctioning process causes a spit to occur reproducibly through the lamina lucida part of the basal membrane between the epidermis and the dermis. Although the thickness of the epidermis varies over different parts of the body, the epidermis over most areas is so delicate and thin as to be transparent. Irrespective of the thickness of the epidermis however, the split occurs at the basal lamina level. The dermis may vary in thickness also but this variation similarly does not affect the level at which the split occurs.

The portion of epidermis which is removed in such a method is devoid of vessels and nerves. The underlying connective tissue of the lamina densa with scattered islands of epithelial adnexae is left behind. The lamina densa is a robust fibrous layer which is open to molecular passage but structurally remains a safeguard to the underlying dermis which remains structurally completely intact.

The blood flow in the exposed dermis is strongly increased for several days following formation of such an erosion allowing increased macro molecular passage, the lymphatic system of the dermis remaining intact and the lymph vessels allowing free passage of even the largest plasma proteins.

The split is formed after exposing the skin surface to a pressure of 200 millimeters of mercury below atmospheric pressure for a period of two to two and a half hours. This period may be reduced to less than one hour by local heating.

During the latter part of the suctioning period, the split fills with clear liquid emanating from the underlying microvessels, finally forming a fluid filled generally semi-spherical blister covered externally by the detached layer of epidermis.

This detached layer of epidermis must be disrupted by being burst, broken or removed in order to provide access for drug absorption or sampling. The exposed dermis will readily absorb fluid substances brought into contact with the dermis at the erosion, the active ingredients of such substances typically being transdermally absorbed by diffusion through the dermis in response to a concentration gradient of the active ingredient existing across the thickness of the dermis, and the substances being rapidly dispersed through the body via the blood vessels of the dermis. A clear fluid exudate continues to form at the erosion by passing outwardly through the dermis. This exudate typically can be analysed to monitor levels of natural or artificial substances in the body. A variety of transdermal perfusion procedures involving the passage of substances through the exposed dermis are thereby envisaged. The term perfusion in the present context is used to encompass such diffusion either into or from the body in either a natural or enhanced manner.

One aspect of the present invention relates to an improved apparatus which can be safely and reliably operated in a simple manner such that in many instances patients themselves may be left to carry out the stages of operation required to complete the procedure.

According to a further aspect of the present invention there is disclosed apparatus for use in transdermal perfusion procedures comprising a housing, securing means operable to secure a contact surface of the housing in sealing contact with an area of skin in use, an aperture defined in the contact surface and communicating with an access port defined by the housing, a suction cup located in the access port and having a lip portion extending peripherally of the aperture, the suction cup defining an outlet port and a suction chamber communicating with both the outlet port and the aperture, the apparatus further comprising suction means operable to apply suction to the suction chamber in the outlet port and cutting means operable to sever from the lip portion a removable portion of the suction cup defining the outlet port.

An advantage of such apparatus is that a suction blister formed within the suction chamber can be safely cut at the same time or the removable portion is severed in a controlled manner by operation of the cutting means and such that a roof of the blister may be disposed of by subsequent removal of the removable portion of the suction cup. The roof of the blister is constituted by an area of epidermis of the skin detached by the formation of the suction blister from the underlying dermis so that following removal of the roof of the blister a small skin erosion is formed providing direct access to the intact dermis for a transdermal perfusion procedure which may involve placing a fluid in contact with the dermis for absorption into the body or may alternatively involve the collection and sampling of exudate emanating from the erosion.

Preferably the apparatus further comprises an actuator mounted on the housing and the cutting means comprises a blade which is movable to sever the removable portion in response to movement of the actuator relative to the housing.

The blade may thereby be safely moved in a controlled manner.

Preferably the suction means defines an expansion chamber communicating with the outlet port via a tube, the suction means being operable to expand the volume of the expansion chamber from an initial volume to an expanded volume and further comprising locking means operable to maintain the expansion chamber in its expanded volume.

Suction within the suction chamber may thereby be applied over a prolonged period by operation of the locking means to maintain the expansion chamber in its expanded condition.

Advantageously the suction means comprises a syringe.

Advantageously the apparatus further comprises an indicator responsive to displacement of air along the tube and operable to provide an indication of volumetric displacement of air from the suction chamber in response to the formation of a suction blister within the suction chamber.

An advantage of such an indicator is to allow the formation of the suction blister to be remotely monitored. This is important since the time taken for the formation of a suction blister of a given size will vary from patient to patient and will vary according to other prevailing operating conditions such as temperature. Visual inspection of the suction blister will not generally be a convenient option.

Conveniently the indicator comprises a slug of liquid contained within the tube and indicating means for indicating the extent of linear displacement of the slug of liquid through the tube.

Conveniently the indicator comprises a clamp securable at an adjustable position along the tube and wherein the indicating means is supported by the clamp.

Preferably the suction means comprises a connector which is releasably engagable with the outlet port whereby disengagement of the connector from the outlet port admits ambient air to the suction chamber.

An advantage of such a connector is to allow the suction means to be dissociated from the housing and discarded by the patient after the formation of the suction blister.

Preferably the apparatus comprises an arming device operable to prevent actuation of the cutting means until the connector has been disconnected from the outlet port.

An advantage of such an arming device is to ensure that the application of suction within the suction chamber is discontinued prior to actuation of the cutting means.

This is a safety feature which avoids the possibility of damaging the underlying dermis. Without this safety feature, there would be the possibility that suction within the suction chamber could deform the dermis into a bulbous projection extending into the suction chamber to an extent such that it could be cut by the blade during the blister cutting operation.

Conveniently the arming device comprises an arming pin insertable into the housing to a location in which it prevents relative movement of the actuator and housing, the arming device further comprising a handle connected to both the connector and the arming pin.

Preferably the housing comprises a base defining the contact surface and a rotatable portion in which the access port is defined at an eccentric location relative to the rotation axis of the rotatable portion.

The rotatable portion may then comprise a reservoir having an outlet located eccentrically relative to the rotational axis such that, after the removable portion has been removed, the outlet is locatable by rotation of the rotatable portion in registration with the aperture defined in the base.

Advantageously a continuous seal extends peripherally of the outlet and is operable between the rotatable portion and the base.

The seal thereby allows the contents of the reservoir to be sealed against loss of contents and ingress of air during an initial period in which the outlet is overlaid by a continuous surface of the base. Subsequently the seal provides sealing action peripherally of the aperture defined in the base when the outlet is in registration with the aperture, loss of fluid thereby being prevented together with the prevention of ingress of contaminants.

Advantageously the apparatus further comprises a second continuous seal peripheral to a surface portion of the rotatable portion at a location which is eccentric relative to the rotational axis such that the surface portion is movable by rotation of the rotatable portion into registration with the aperture.

The surface portion of the rotatable portion may thereby be used to form a closure to the suction chamber after use of the apparatus to deliver the contents of the reservoir to the dermis, in this final position the second continuous seal being operable to form an airtight seal between the surface portion and the base against the ingress of contaminants.

Conveniently the continuous seal and the second continuous seal are integrally formed.

Advantageously the suction cup comprises a cylindrical portion intermediate the lip and the outlet port and having a cylindrical axis substantially orthogonal to the contact surface and the cutting means is operable to sever the cylindrical portion at a predetermined location spaced from the lip portion.

Preferably the suction cup comprises an internal surface which is adhesively coated.

A suction blister will therefore tend to adhere to the internal surfaces of the suction cup thereby avoiding the collapse of the blister before cutting in the event of the blister becoming accidentally ruptured.

The rotatable portion may define a sampling port at an eccentric location relative to the rotation axis of the rotatable portion, the apparatus further comprising a sampling piston reciprocatable in the sampling port to vary the volume of a sampling chamber defined therein whereby suction may be created in the sampling chamber, the sampling port being locatable, after the removable portion has been removed, by rotation of the rotatable portion in registration with the aperture defined in the base such that the aperture communicates with the sampling chamber.

Exudate emanating from the exposed dermis may thereby be sampled via the sampling port without removal of the housing from the skin to which it is attached. On completion of sampling, the rotatable portion may then be rotated into a position in which the delivery of a drug commences or recommences, or alternatively may be rotated into a position in which the erosion is occluded.

The ability of the sampling piston to create suction in the sampling chamber may be utilised to enhance the rate at which exudate is collected from the erosion by increasing the rate of production of exudate in response to a pressure differential applied across the dermis.

Conveniently the sampling piston defines a bore to receive an outflow of fluid from the sampling chamber, the apparatus further comprising an openable closure operable to close the bore to maintain suction in the sampling chamber.

Access to the exudate fluid in the sampling chamber may thereby be gained by opening the closure as required.

Conveniently the apparatus further comprises a sampling device connected to the sampling piston and defining a sampling channel communicating in use with the bore to receive a sample of fluid from the sampling chamber.

Advantageously the sampling piston is reciprocatable in the sampling port by means of co-operable screw threaded formations of the sampling piston and the rotatable portion.

According to a further aspect of the present invention there is disclosed a syringe for creating suction to be applied to the suction blister forming apparatus, the syringe comprising a cylinder within which a piston is movable to define an expansion chamber of variable volume, the piston comprising an actuating handle projecting from the cylinder and a locking arm formed integrally therewith, the locking arm being resiliently biased for movement into a locking position in which a free end of the locking arm engages a co-operating locking formation of the cylinder when the piston is in a retracted position to create and maintain suction in the expansion chamber.

Such a syringe may be conveniently locked for a prolonged period with the piston in the retracted position to thereby maintain suction during the formation of a suction blister.

According to a further aspect of the present invention there is disclosed apparatus for use in transdermal perfusion procedures comprising a suction cup for use in applying suction to an area of skin, a tube communicating with the suction cup and connectable in use to a suction means, and an indicator responsive to displacement of air along the tube and operable to provide an indication of volumetric displacement of air from the suction cup in response to the formation of a suction blister or the ingress of body fluid within the suction cup during a period in which suction is maintained within the suction cup.

Such an indicator overcomes the problem of determining whether a suction blister has sufficiently formed before initiating the next stage of removing or disrupting the blister roof to expose the dermis. Such an indicator provides a convenient means of measuring volumetric growth of a suction blister without requiring contact with the blister and avoiding the need to incorporate any sensor or measurement device in the immediate proximity of the blister. The indicator will typically be located several centimeters clear of the suction cup.

Similarly, when used in the collection of exudate at an erosion, the indicator allows the collected volume of exudate to be readily observed.

Preferably the indicator comprises a slug of liquid located in a transparent portion of the tube and indicating means for indicating the extent of linear displacement of the slug of liquid through the tube.

Displacement of the slug of liquid may be observed visually relative to a scale clamped to the tube or may be monitored by an electro-optic sensor.

Preferably the apparatus comprises a liquid storage structure connected to the tube and defining a liquid storage chamber communicating with the transparent portion of the tube and means for displacing a quantity of liquid from the liquid storage chamber into the tube to thereby constitute the slug of liquid.

An advantage of such an arrangement is that it avoids the need for the slug of liquid to be held within the tube prior to use, thereby overcoming the potential problem of disruption of the slug of liquid by handling prior to use.

According to a further aspect of the present invention there is disclosed apparatus for use in transdermal perfusion procedures, comprising a housing, securing means operable to secure a contact surface of the housing in sealing contact with an area of skin in use, an aperture defined in the contact surface, the housing comprising a base defining the contact surface and a rotatable portion in which an access port is defined at an eccentric location relative to the rotation axis of the rotatable portion and whereby in an initial position of the rotatable portion the access port is aligned in registration with the aperture to facilitate formation of a de-epithelialised skin erosion within the aperture, the rotatable portion further comprising a plurality of openings defined at eccentric locations relative to the rotation axis of the rotatable portion whereby successive openings may be brought into registration with the aperture by rotation of the rotatable portion and a plurality of compartments within the rotatable portion which are accessible via the respective openings.

Two or more of the compartments may comprise reservoirs containing respective fluids whereby the respective fluids may be separately and sequentially communicated to the aperture via respective openings by successive rotational steps of the rotatable portion.

One or more of the compartments may contain means for sampling body fluids communicated to the compartment from the aperture via the respective opening.

Advantageously the apparatus comprises an actuating mechanism operable to facilitate rotational movement of the rotatable portion relative to the base in response to movement of an actuating member of the mechanism.

The mechanism may comprise a geared pinion mounted on the base for rotation by movement of the actuator and a circumferential rack mounted on the rotatable portion and engaged by the pinion.

According to a further aspect of the present invention there is disclosed apparatus for use in transdermal perfusion procedures, comprising a housing, securing means operable to secure a contact surface of the housing in sealing contact with an area of skin in use, an aperture defined in the contact surface and communicating with an access port defined by the housing, means for applying suction to the aperture via the access port and heating means operable to apply heat to a heated portion of the contact surface peripheral to the aperture.

When the housing is secured to an area of skin to form a suction blister, the application of heat reduces the time taken for a suction blister to form. When applied to an area of skin in which a de-epithelialised erosion exists for the purpose of sampling exudate, the application of heat enhances the rate at which exudate may be collected.

The heating means may comprise a resistive heating element and a power circuit operable to pass electrical current through the heating element.

According to a further aspect of the present invention there is disclosed apparatus for use in transdermal perfusion procedures, comprising a housing, securing means operable to secure a contact surface of the housing in sealing contact with an area of skin in use, an aperture defined in the contact surface, the surface comprising a base defining the contact surface and a moveable portion in which an access port is defined, the moveable portion being moveable between an initial position in which the access port is aligned in registration with the aperture to facilitate formation of a de-epithelialised skin erosion within the aperture and a second in position in which an opening defined by the moveable portion is located in registration with the aperture, and further comprising a pump operable to transfer liquid between the aperture and the compartment via the opening.

According to a further aspect of the present invention there is disclosed apparatus for use in transdermal perfusion procedures, comprising a housing, securing means operable to secure a contact surface of the housing in sealing contact with an area of skin in use, an aperture defined in the contact surface whereby a de-epithelialised skin erosion may be formed in use via the aperture, the housing defining an enclosure communicating with the aperture and a syringe connected to the enclosure for the delivery of liquid thereto, wherein the syringe comprises a piston and cylinder and screw-threaded actuating means for advancing the piston in metered stages by rotation of the actuator relative to the cylinder to thereby dispense metered doses of liquid.

This provides a convenient means of delivering metered quantities of liquid for transdermal absorption at a de-epithelialised skin erosion.

According to a further aspect of the present invention there is disclosed apparatus for use in transdermal perfusion procedures, comprising a housing, securing means operable to secure a contact surface of the housing in sealing contact with an area of skin in use, an aperture defined in the contact surface, the housing comprising a base defining the contact surface and a moveable portion in which an access port is defined and whereby in an initial position of the moveable portion the access port is aligned in registration with the aperture to facilitate formation of a de-epithelialised skin erosion within the aperture, the moveable portion further comprising an opening which may be brought into registration with the aperture in a second position of the moveable portion thereby providing communication between a chamber of the moveable portion and the aperture, the apparatus further comprising a transdermal skin patch accommodated within the chamber and a patch applicator operable in use to deploy the patch from the chamber through the aperture into engagement with the skin erosion.

An advantage of such apparatus is that a patch may be applied to the skin erosion without being handled by the user and without exposing the de-epithelialised skin erosion.

According to a further aspect of the present invention there is disclosed a method of administering a substance by transdermal delivery, comprising the steps of preparing first and second de-epithelialised skin erosions at separate skin sites, applying first and second enclosures respectively over the first and second erosions to define a sampling cell and a drug delivery cell respectively, extracting exudate from the sampling cell by means of a first pump to a bio-sensor, operating the bio-sensor to produce an output signal representative of a measurable property of the exudate, delivering metered quantities of a liquid containing the substance to the drug delivery cell by operation of a second pump, controlling the rate of delivery of the second pump by operation of a control unit responsive to the output of the bio-sensor.

According to a further aspect of the present invention there is disclosed a method of controlled release of a substance for transdermal absorption, comprising the steps of absorbing quantities of the substance into porous polymeric particles, mixing the particles with granules of permanent magnetic material encapsulated in a polymeric material, placing the resulting mixture in a cell defined by an enclosure, applying an alternating magnetic field within the cell, thereby inducing mechanical vibration in the mixture to release the substance from the particles.

According to a further aspect of the present invention there is disclosed a method of controlled release of a substance for transdermal absorption, comprising the steps of mixing a liquid containing the substance with a quantity of a hydrogel, placing the resulting mixture within a cell defined an enclosure and heating the contents of the cell by operation of a heating means to thereby dissociate liquid from the hydrogel so as to be released from the cell.

According to a further aspect of the present invention there is disclosed apparatus for use in transdermal perfusion procedures, comprising a housing, securing means operable to secure a contact surface of the housing in sealing contact with an area of skin in use, an aperture defined in the contact surface, the housing comprising a base defining the contact surface and a movable portion in which an access port is defined and whereby in an initial position of the movable portion the access port is aligned in registration with the aperture to facilitate formation of a de-epithelialised skin erosion within the aperture, the movable portion further comprising an opening which may be brought into registration with the aperture in a second position of the movable portion, the apparatus further comprising an implementing device operable in use to implement a transdermal procedure at the skin erosion via the opening and releasable connecting means operable between the movable portion and the implementing device.

An advantage of such apparatus is to allow a succession of different implementing devices to be connected, thereby allowing a sequence of different procedures to be performed or to allow procedures to be repeated with fresh implementing devices.

Preferably the implementing device comprises a reservoir defining a fluid receiving chamber and an outlet communicating with the opening of the movable portion when the implementing device is operatively connected therewith.

Successive implementing devices may thereby be connected in turn. In this way a succession of different drugs or drug concentrations may be administered.

Conveniently the implementing device comprises suction means connected to the opening when the implementing device is operatively connected therewith and operable to create suction to thereby draw fluid from the fluid receiving chamber into the opening.

The operation of the suction means enables the liquid contained in a reservoir to displace air from the opening and fluid into contact with the de-epithelialised skin erosion. When replacing one implementing device with a further device, operation of the suction means in the further implementing device will also serve to evacuate from the opening any residual liquid remaining from the application of the previous implementing device.

According to a further aspect of the present invention there is disclosed a method of transdermally sampling body fluid from the human or animal body comprising the steps of:

removing an epithelial layer from a portion of skin at a skin site;

securing an enclosure defining a sampling chamber to the body such that a contact surface of the enclosure is maintained in sealing contact with an area of skin peripheral to the skin site;

operating a suction means connected to the enclosure to apply suction within the sampling chamber during a period in which transdermally exuded body fluid is collected in the sampling chamber;

discontinuing the application of suction, and sampling fluid from the sampling chamber via an operable closure of the enclosure.

Such a method provides an improved, minimally invasive procedure for sampling from the body. Removal of the epithelial layer from the portion of skin exposes an area of dermis at an erosion formed at the skin site. As described above, in the absence of applied suction to the exposed dermis, exudate will be produced gradually at the erosion. The application of suction enhances the rate of production of exudate. The effect of suction is to reduce the air pressure external to the dermis thereby creating a pressure differential across the dermis resulting in convective flow of plasma through the dermis. The dermis acts as a porous capillary membrane which acts as a sieve preventing the loss of blood cells but permitting relatively large molecules such as molecules of sugar and insulin to be carried in the exuded plasma. The rate at which fluid is exuded is thereby increased above the rate associated with normal diffusion of plasma through the dermis in the absence of suction. The time taken for plasma to pass through the dermis is reduced thereby decreasing the risk of significant reactions taking place in the plasma during this transition.

An advantage of using this method is that a fresh sample of exudate may be drawn from the erosion within a relatively short time period of the order of five minutes for example, in sufficient quantity for an analysis to be carried out. Typically small volumes of fluid are required for modern analysis techniques including chemiluminescence and fluorescence for example.

The method is preferable over known techniques of invasive sampling, such as the use of a hypodermic needle, where typically unnecessarily large volumes are sampled and the resulting wound which penetrates the dermis may create difficulties such as those of thrombosis in vessels where sampling is frequently conducted.

The method of the present invention also has particular advantage in taking samples from paediatric patients and premature babies where vessels for cannulation are difficult to find and where it is undesirable to withdraw significant volumes for sampling due to risk associated with blood loss.

According to the present invention there is further disclosed apparatus for use in sampling exudate from a de-epithelialised skin erosion, the apparatus comprising an enclosure defining a sampling chamber, securing means operable to sealingly secure a contact surface of the enclosure to an area of skin peripheral to the erosion in use, an aperture being defined in the contact surface and communicating with the sampling chamber, an outlet communicating with the sampling chamber for the outflow of exudate, an openable closure for the outlet, and means for applying suction within the sampling chamber to enhance the rate at which exudate is produced.

Conveniently the means for applying suction comprises a piston reciprocatably mounted in the sampling chamber whereby the volume of the sampling chamber is variable.

Preferably the chamber is cylindrical and receives the piston as a sliding fit therein.

Advantageously the piston defines a capillary bore extending through the piston and communicating between the chamber and the outlet.

The openable closure may comprise a cap releasably attachable to the piston.

The apparatus may further comprise a sampling device releasably connectable to the piston and defining a sampling channel communicating with the bore to receive in use a sample of exudate from the chamber.

The sampling device may be a transparent cuvette defining a capillary slot constituting the sampling channel and operable to sample exudate from the outlet by capillary action.

The means for applying suction may alternatively comprise a syringe connected to an air of actuation port defined by the enclosure.

The outlet may then be formed in a tubular side wall of the enclosure, the outlet being overlaid by a resilient sleeve constituting the openable closure.

Preferred embodiments of the present invention will now be described by way of example only and with reference to the accompanying drawings of which FIG. 1 is a sectioned elevation of a first apparatus for forming a suction blister;

FIG. 2 is a sectioned elevation of a second apparatus for forming a suction blister and having an actuator pin;

FIG. 3 is a sectioned elevation of the apparatus of FIG. 2 showing the actuator pin in an advanced position in readiness to disrupt a suction blister;

FIG. 4 is a sectioned elevation of the apparatus of FIGS. 2 and 3 showing the actuator pin in a further advanced position in which the blister is disrupted to expose the dermis;

FIG. 5 is a sectioned elevation of a third apparatus for forming a suction blister and having a pull ring actuator;

FIG. 6 is a sectioned elevation of a fourth apparatus for forming a suction blister and having laterally disposed actuator pins;

FIG. 7 is a sectioned elevation of a fifth apparatus for forming a suction blister and comprising a sprung bellows shown in a compressed state;

FIG. 8 is a sectioned elevation of the apparatus of FIG. 7 showing the sprung bellows in an expanded state;

FIG. 9 is a sectioned elevation of a sixth apparatus for removing an area of epidermis by grinding;

FIG. 10 is a sectioned elevation of a seventh apparatus for use in transdermal perfusion of a drug;

FIG. 11 is a sectioned elevation of the apparatus of FIG. 10 showing removal of a de-epithelialisation component of the apparatus;

FIG. 12 is a sectioned elevation of the apparatus of FIGS. 10 and 11 in which the de-epithelialisation component is replaced by a drug delivery module;

FIG. 13 is a sectioned elevation of an alternative drug delivery module for use with the apparatus of FIGS. 10 to 12;

FIG. 14 is a sectioned elevation of an eighth apparatus for transdermal delivery of a drug including means for forming a suction blister, disrupting the blister and applying the drug directly to the exposed dermis;

FIG. 15 is a sectioned elevation of a ninth apparatus having a cannula for drug delivery by injection;

FIG. 16 is a sectioned elevation of the apparatus of FIG. 15 showing the cannula extending through the skin;

FIG. 24 is a sectioned elevation of the apparatus of FIGS. 21 to 23 showing the disruption of the blister;

FIG. 27 is a section showing detail of a drug injection port of the apparatus of FIGS. 21 to 26;

FIG. 28 is a section showing detail of a suction port valve of the apparatus of FIGS. 21 to 27;

FIG. 29 is a section showing detail of an alternative drug injection port for use with the apparatus of FIGS. 21 to 26;

FIG. 34 is a schematic sectional elevation of an alternative device showing the formation of a suction blister within a suction cup;

FIG. 35 is a schematic sectional elevation of the device of FIG. 34 after the suction cup and blister have been severed;

FIG. 36 is a sectioned elevation of the device of FIGS. 34 and 35 during a drug delivery phase of operation;

FIG. 37 is a sectional elevation of the device of FIGS. 34 to 36 shown after completion of the drug delivery phase;

FIG. 57 is a schematic plan view of a further alternative device having a micro pump for delivering metered quantities of liquid;

FIG. 58 is a schematic plan view of a further alternative device having a micro pump for sampling quantities of liquid;

FIG. 61 is a partly sectioned plan view of the syringe of FIG. 60;

FIG. 62 is a partly sectioned plan view of the device of the syringe of FIGS. 60 and 61 in a retracted configuration;

FIG. 63 is a schematic sectioned elevation of a further alternative device including a patch applicator;

FIG. 64 is a schematic underneath plan view of the device of FIG. 63;

FIG. 65 is a schematic sectioned elevation of the device of FIGS. 63 and 64 following the severing of the blister;

FIG. 66 is a schematic sectioned elevation of the device of FIGS. 63 to 65 following separation of a protective film from the patch;

FIG. 102 is a sectional elevation of the device shown in FIG. 101 with the sampling port not in use;

FIG. 104 is a sectional elevation of the device shown in FIG. 103 showing the sampling port in use;

FIG. 105 is a sectional elevation of the device of FIG. 104 after retraction of the sampling piston to a fully retracted position;

FIG. 106 is a sectional elevation of the device of FIG. 105 after advancing the sampling piston to an intermediate position;

Figure 17:
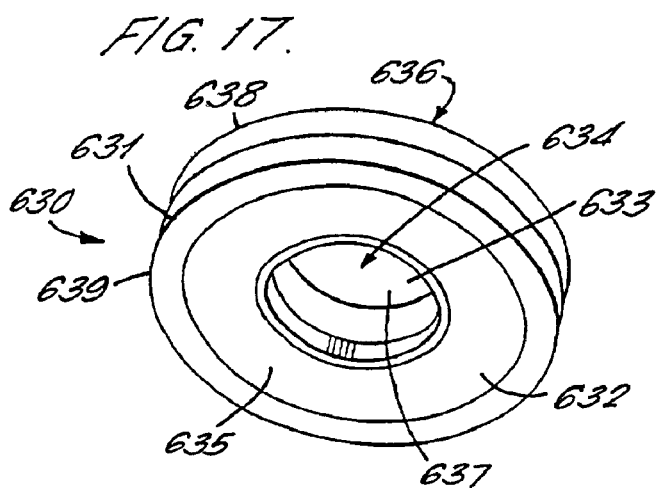
FIG. 17 is a perspective view of a tenth apparatus for transdermal delivery of a drug and showing a suction chamber in its pre-use configuration.

In FIG. 1 a first apparatus 501 comprises a housing 502 of two-part construction. The housing 502 consists of a disc 503 and an evacuated cell 504 which is similarly of disc-shape and fits onto an upper surface 505 of the disc in use.

The disc 503 is formed of a rigid transparent plastics material and has a lower surface 506 which is coated with adhesive and prior to use is protected by a peel-off paper film 507. The disc 503 is centrally recessed to define a cup-shaped chamber 508 within a cylindrical formation 509 which projects upwardly of the upper surface 505. A cannula 510 projects from the cylindrical formation 509 in a direction away from the disc 503 so as to define a duct 511 communicating with the chamber 508. The cannula 510 is shown in FIG. 1 in its pre-use configuration in which it is externally covered by a closed rubber sleeve 512.

The cell 504 is formed of a rigid transparent plastics material and encloses a space 513 which is provided at manufacture with a partial vacuum of 200 mm of mercury.

The cell 504 has a lower face 514 which is centrally recessed by a cylindrical formation 515 within which the cylindrical formation 509 of the disc 503 is a sliding fit. The cylindrical formation 515 is closed by a disruptable membrane 516 formed of rubber.

The disc 503 is of 50 mm diameter and defines a central aperture of 5 mm diameter communicating with the chamber 508.

In use the paper film 507 is peeled off and the disc 503 is presented to an area of skin of the patient. The disc 503 is pressed onto the skin such that lower surface 506 is adhesively secured against the skin and forms an airtight seal. The cell 504 is advanced onto the disc 503 such that cylindrical formation 515 fits over the cylindrical formation 509 and the cannula 510 ruptures both the rubber sleeve 512 and membrane 516 to establish communication via the duct 511 between the space 513 and the chamber 508. A partial vacuum is thereby applied within the chamber 508 to an area of skin within aperture 518. The apparatus 501 is held in this position adhesively for two to three hours during which time a suction blister is formed within the chamber 508. Formation of the blister can be observed by inspection through the transparent material forming the cell 504 and disc 503. The apparatus is then removed from the skin by first removing the cell 504 to release the partial vacuum within chamber 508 and then peeling the disc 503 away from the skin.

The exposed blister may then be broken or removed to gain access for transdermal delivery of a drug to the exposed skin dermis or the blister fluid may be sampled for subsequent analysis.

A second apparatus 520 shown in FIG. 2 comprises a housing 521 which includes a transparent disc-shaped base 522 defining a contact surface 523. The contact surface 523 has an adhesive coating which is protected prior to use by a peel-off paper film 524. The contact surface 523 is centrally recessed by a cylindrical formation 525 defining a cylindrical chamber 526, the contact surface 523 defining a circular aperture 527 of 5 mm diameter communicating with the chamber 526. The chamber is closed at its other end by a disruptable rubber membrane 528.

The housing 521 further comprises a cell 529 of transparent plastics material which is closed by membrane 528 to enclose a sealed space 530. The space 530 is evacuated at manufacture to provide a partial vacuum of 200 mm of mercury.

An actuator pin 531 projects sealingly through an outer wall 532 of cell 529. Actuator pin 531 is axially movable towards the membrane 528 so as to form a central puncture in use.

In use the film 524 is peeled off and the contact surface 523 is adhesively secured to the skin of the patient so as to form an airtight seal. The chamber 526 is then closed by an area of skin defined within the aperture 533. Actuator pin 531 is then advanced so as to rupture the membrane 528 and air moves through the ruptured membrane to equalise pressure in the space 530 and chamber 526. A partial vacuum is thereby applied to the area of skin exposed within the aperture 533. The chamber 526 and the space 530 together constitute a closed compartment in which a partial vacuum is maintained so long as the ingress of air is prevented by the airtight seal between the contact surface and the skin. The apparatus 520 is left in situ for a period of about two hours during which time the formation of a suction blister 534 is observed through the transparent housing 521 as shown in FIG. 3. In FIG. 3 the actuator pin 531 is shown in an orientation in which it is rotated through 90° relative to the position shown in FIG. 2 thereby revealing cutting edges 535 which disrupt the blister 534 as shown in FIG. 4 when the actuator pin is further advanced.

The contents of the blister 534 may be sampled and analysed or a skin patch (not shown) may be applied over the site of the broken blister to apply a liquid drug to be perfused through the exposed dermis.

A third apparatus 540 is shown in FIG. 5 and will be described using corresponding reference numerals to those of FIGS. 2, 3 and 4 where appropriate for corresponding elements.

Apparatus 540 similarly has a transparent housing 521 with a cell 529 enclosing an evacuated space 530 and suction is applied through aperture 527 in contact surface 523 by creating a partial vacuum in chamber 526 by disrupting a membrane 528. The apparatus 540 includes a pull-ring actuator 541 to which is attached a first end 542 of a wire 543 of which a second end 544 is anchored in the membrane 528. The wire 543 is enclosed within a sheath 545 which is sealed to both the outer wall 532 of the cell 529 and the membrane 528.

In use the pull-ring actuator 541 is pulled to displace the wire 543 so that the second end 544 is pulled through the membrane 528 leaving a hole through which air flows between the chamber 526 and space 530. A partial vacuum is thereby applied to the chamber 526 for the formation of a skin blister. The partial vacuum then persists in the closed compartment constituted by chamber 526 and space 530 so long as an airtight seal across the aperture is provided by adhesive contact with the skin.

A fourth apparatus 550 is shown in FIG. 5 and will be described using corresponding reference numerals to those of FIG. 2 where appropriate for corresponding elements.

Apparatus 550 comprises a transparent housing 521 having a contact surface 523 and an evacuated cell 529. A cylindrical formation 525 defines a chamber 526 which is closed by adhesion of the contact surface 523 to an area of skin and partial vacuum within the chamber 526 is then applied by disrupting side walls 551 of the cylindrical formation 525 by means of laterally extending actuator pins 552 and 553. Operation of the apparatus 550 is in other respects similar to that of apparatus 520.

In FIG. 7 a fifth apparatus 560 comprises a disc-shaped base 561 defining a central aperture 562 which communicates directly with a chamber 563 defined by a bellows 564. The bellows 564 is biassed by coil springs 565 and 566 into an extended position as shown in FIG. 8. The apparatus 560 is normally stored in its compressed state as shown in FIG. 7 and the base 561 defines a contact surface 567 which is adhesively coated and is provided pre-use with a protective film 568. The film 568 closes aperture 561 in this condition to prevent ingress of debris during storage.

The bellows 564 is clamped in its compressed condition by means of a clamp (not shown) and an actuator (not shown) is provided to release the clamp to allow the bellows to expand to its expanded configuration shown in FIG. 8.

In use the film 568 is removed and the contact surface 567 applied to the skin so that aperture 562 is closed in airtight manner by an area of skin. The actuator is operated to unclamp the bellows 564 and the bellows expand by spring action to thereby increase the volume of chamber 563 and this results in the creation of a partial vacuum which is applied to the area of skin exposed by aperture 562. The apparatus 560 is left in situ for a period of about two hours and may then be removed first by compressing the bellows to its original shape to remove the partial vacuum and then peeling off the contact surface from the skin. The blister may then be broken or removed and a transdermal skin patch applied to the exposed dermis.

A sixth apparatus 570 is shown in FIG. 9 and comprises a disc 571 which is axially mounted on a shaft 572. The disc 571 has a flat contact surface 573 from which a plurality of sharp edged protrusions 574 project towards the skin. The protrusions 574 have a height corresponding to the depth of epidermis and in use the contact surface is placed against the skin and the disc rotated by means of shaft 572 to thereby form incisions in the epidermis. The apparatus 570 is then removed and a skin patch containing a drug is then applied to the area of skin in which the incisions are formed.

A seventh apparatus 580 is shown in FIGS. 10, 11 and 12 and comprises a housing 581 consisting of an annular frame 582 which is adhesively secured to an area of skin 583 in use. A de-epithelialising apparatus 584 is releasably locatable within the annular frame 582 and in FIGS. 10 and 11 the de-epithelialising apparatus 584 is of the type described above with reference to FIGS. 2, 3 and 4 in which a suction blister is formed and ruptured by actuation of an actuator pin 585. In FIG. 10 the de-epithelialising apparatus 584 is shown in situ prior to use. In FIG. 11 the de-epithelialising apparatus is shown separated from the frame 582 after formation and rupturing of the blister (not shown). FIG. 12 shows a drug delivery module 586 located within the frame 582 following removal of the de-epithelialising apparatus 584. The drug delivery module 586 comprises a disc-shaped casing 587 having a central drug compartment 588 which includes a semi-permeable membrane 589 through which the drug exudes at a predetermined rate. (Detail of the ruptured blister is omitted from FIG. 12).

The casing 587 is configured to be a close fit within the frame 582 and to locate the membrane 589 over the location of the area of skin which is de-epithelialised by the apparatus 584.

The diameter of the membrane 589 is greater than the diameter of the de-epithelialised skin patch to take account of any errors in positioning.

The apparatus of FIGS. 10 to 12 may alternatively utilise the apparatus of FIG. 9 in achieving de-epithelialising of the skin, the apparatus 570 being located within the frame 582 and removed prior to insertion of drug delivery module 586.

An alternative drug delivery module 590 is shown in FIG. 13 and comprises a reservoir 591 containing a volume of drug, the reservoir being held by an annular support 592 in proximity with skin surface 593. The support 592 defines a narrow bore connecting tube 594 communicating between the reservoir 591 and a recess 595 which is defined by the support and overlays the de-epithelialised skin area. Liquid drug is progressively fed by capillary action through the connecting tube 594 into the recess and hence is perfused through the exposed dermis.

The flow of liquid through the connecting tube may be aided by the application of positive pressure to the reservoir 591.

In FIG. 14 an eighth apparatus 600 for the transdermal delivery of a drug comprises a transparent housing 601 with a disc-shaped base 602. A contact surface 603 is adhesively coated so as to adhere to a skin surface and the base defines a central aperture 604 communicating with a chamber 605 formed by a cylindrical formation 606.

The cylindrical formation 606 is closed at one end by a frangible membrane 607 which initially separates the chamber 605 from an evacuated space 608 provided by a cell 609 of the housing 601.

The frangible membrane 607 is disruptable by means of an actuator pin 610 of the type described above with reference to FIGS. 2, 3 and 4 so that actuation of the pin 610 ruptures the membrane to introduce partial vacuum into the chamber 605 during a blister forming period. Further actuation of the pin 610 advances the pin to a position in which it will disrupt the blister to expose the dermis within the chamber 605.

Apparatus 600 also comprises an integrally formed drug reservoir 611 which is normally sealed by a frangible plug 612. A drug release actuator 613 is provided for breaking the plug 612 and allowing the drug to flow into the chamber 605.

In use the apparatus 600 is placed on the skin such that adhesion between the contact surface 603 and skin provides an airtight seal across the aperture 604. The actuator pin is then advanced to disrupt the membrane 607 so that a partial vacuum is produced in the chamber 605 to form a blister. The cell and chamber together constitute a closed compartment sealed by the area of skin and in which partial vacuum persists during a blister forming period. The blister is then ruptured by further actuation of actuator pin 610 and the drug release actuator 613 is then operated to allow drug into the chamber 605. De-epithelialised dermis exposed by rupturing the blister is then exposed to the drug and transdermal perfusion then proceeds.

In FIG. 15 a ninth apparatus 620 includes an apparatus for transdermal drug delivery such as that described with reference to FIG. 14 (details of such transdermal apparatus are not shown in FIG. 15) and additionally includes an injection device 621 which is operable to inject via a cannula 622 an initial dose of drug prior to de-epithelialisation and transdermal delivery by means of the transdermal apparatus using an adjacent patch of skin. Such immediate administration of a dose is useful in administering pain relief for example or control of premature muscle contractions of the uterus during pre-term labour.

The injection device 621 comprises an additional suction cup 623 defining a suction chamber 624 to which suction is applied to immediately draw skin into the chamber as shown in FIG. 16. The cannula 622 is located within the chamber in a position such that skin drawn into the chamber by suction is penetrated. Drug is then injected through the cannula from a reservoir 625 on release of a valve 626. Drug within the reservoir 625 is pressurised by means of an expanding device 627 placed in contact with the reservoir 625 which is formed of a deformable material so as to be collapsible.

A tenth apparatus 630 shown in FIG. 17 comprises a housing 631 having an annular contact surface 632 defining an aperture 633. The housing 631 is centrally recessed to define a chamber 634 communicating with the aperture.

The housing 631 incorporates an annular drug reservoir 635 peripherally disposed relative to the aperture 633 and includes an evacuated cell 636 which is isolated from the chamber 634 prior to use by a disruptable membrane 637.

The housing 631 has an actuator cap 638 which is movable relative to a base portion 639 which includes the contact surface 632.

Apparatus 630 is arranged to provide for the formation and disruption of a suction blister and for subsequent drug delivery to the exposed dermis by successive actuation of the actuator cap 638.

The housing 631 is initially secured to a patch of skin such that the aperture 633 is closed in a sealed manner by an area of skin through which drug is to be transdermally delivered. The housing 631 is secured by means of a peripheral support frame (not shown).

Figure 18:
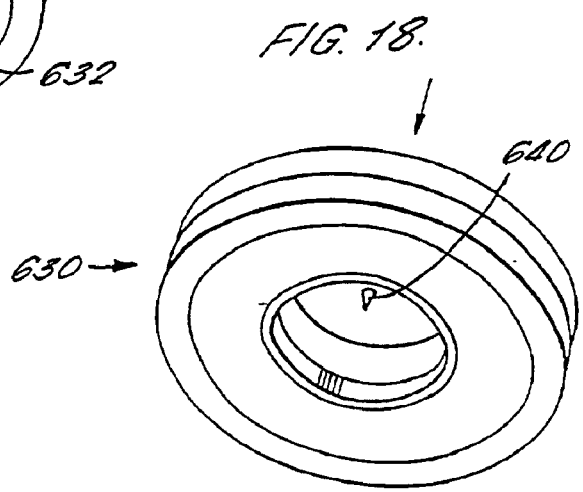
FIG. 18 is a perspective view of the apparatus of FIG. 17 showing the introduction via a cannula of partial vacuum within the suction chamber.

As shown in FIG. 18 the actuator cap 638 is pressed towards the base portion 639 so as to advance a cannula 640 so as to penetrate the membrane 637 and place the chamber 634 in communication with the evacuated cell 636. A partial vacuum is thereby created within the chamber 634 and the partial vacuum persists during a blister forming period by virtue of the contact surface 632 being sealed against the skin.

Figure 19:
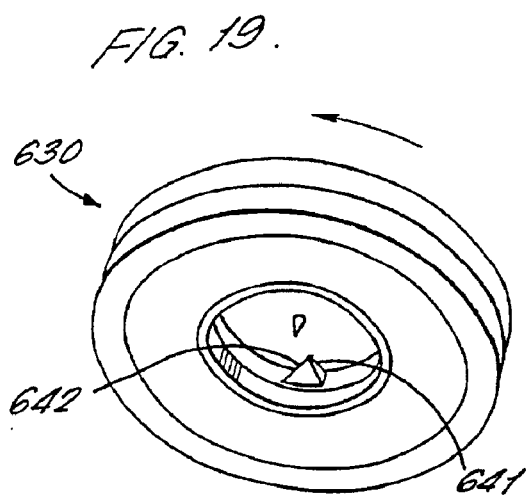
FIG. 19 is a perspective view of the apparatus of FIGS. 17 and 18 showing actuation of a blister disrupting fin.

After a period of two hours the actuator cap 638 is rotated through 45° as shown in FIG. 19 in response to which motion air is admitted to the chamber 634 through a release valve (not shown) so as to restore atmospheric pressure and a blister disrupting fin 641 moves into the chamber 634 and breaks or removes the roof of the blister formed within the chamber. The fin 641 includes an absorbent layer 642 which absorbs blister fluid released by this motion.

Figure 20:
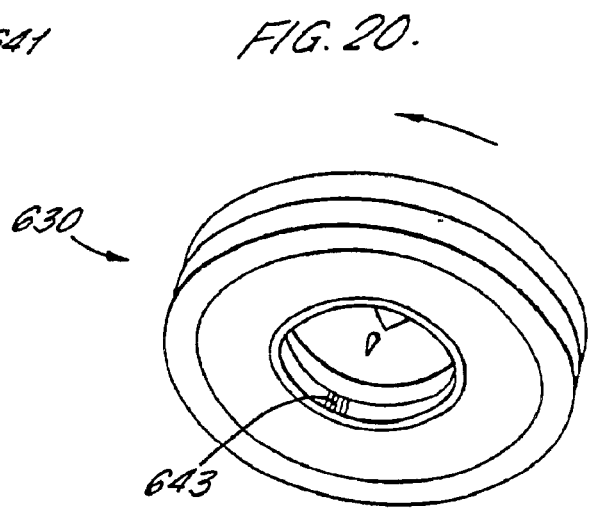
FIG. 20 is a perspective view of the apparatus of FIGS. 17 to 19 showing the opening of a valve admitting drug to the chamber.

The actuator cap 638 is again further advanced as shown in FIG. 20 through a rotational movement of 45° and this further motion opens a valve to release a liquid drug from the reservoir 635 through an outlet 143 into the chamber 634.

Transdermal perfusion of the drug through the exposed dermis of the skin then proceeds.

Figure 21:
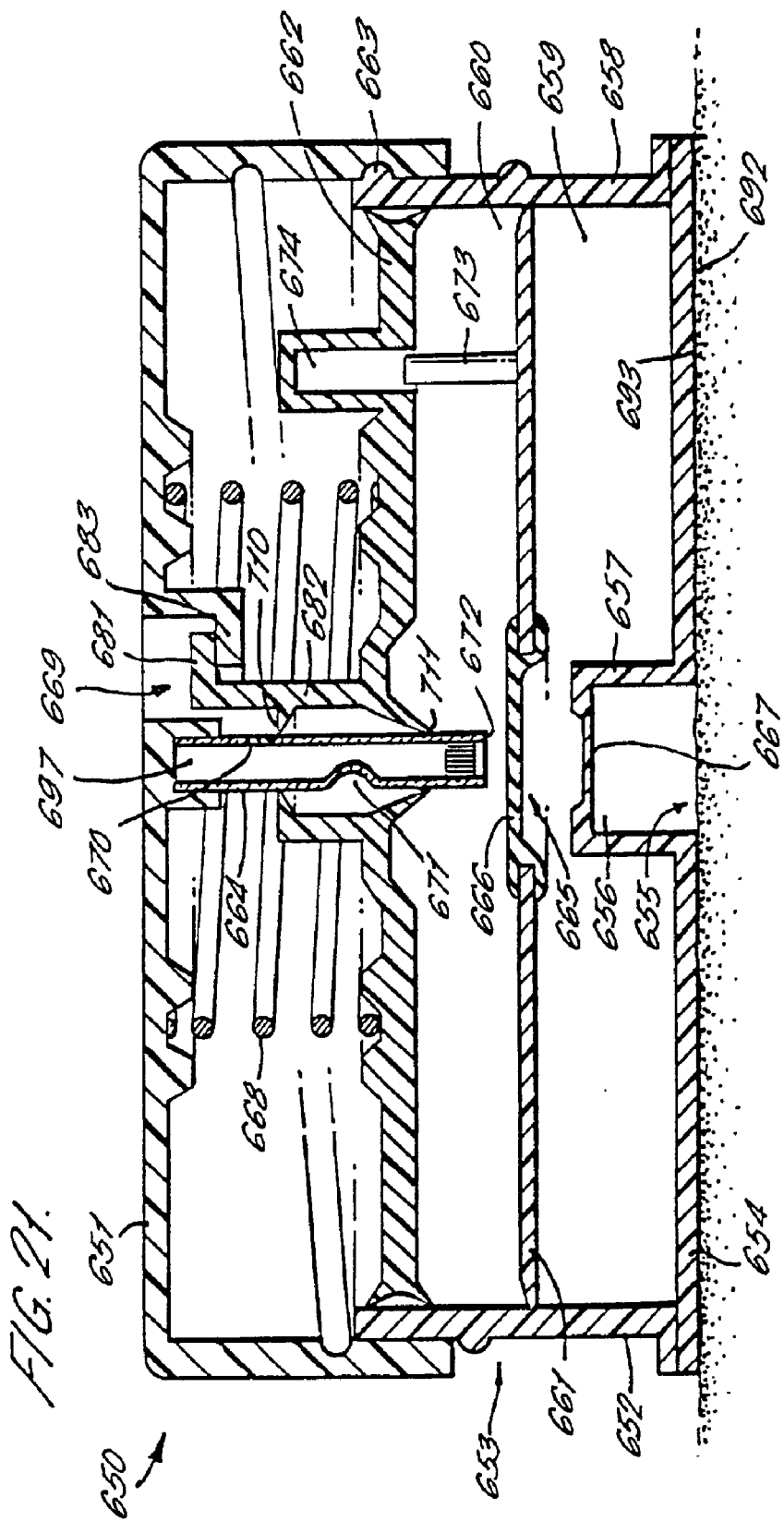
FIG. 21 is a sectioned elevation of an eleventh apparatus for transdermal drug delivery in its pre-use configuration.

An eleventh apparatus 650 shown in FIG. 21 also includes an actuator cap 651 which provides successive operations of blister formation, blister disruption and drug release by successive stages of movement of the cap relative to a base portion 652 of a housing 653. The housing 653 includes a disc portion 654 having a flat disc-shaped contact surface 692 defining a central aperture 655 of 5 mm diameter. The aperture 655 communicates with a chamber 656 defined by a cylindrical formation 657 projecting upwardly of the disc portion.

The housing 653 includes a cell 658 bounded on one side by the disc portion 654 and defining a closed space 659. The housing 653 also includes a drug reservoir 660 which is separated from the space 659 by a partition 661 extending parallel to the disc portion 654.

The volume of the drug reservoir 660 is variable by movement of a piston 662 which is movable towards the partition 661 to reduce the volume of the reservoir for the purpose of expelling liquid drug.

The housing 653 is cylindrical in shape and the actuator cap 651 is similarly cylindrical and overlays the housing, the housing and cap having cooperating screw threads 663 whereby rotation of the cap relative to the housing advances the cap towards the disc portion 654.

A hollow needle 664 is mounted axially within the cap 651 such that rotation of the cap produces axial movement of the needle relative to the housing.

In FIG. 21 the apparatus 650 is shown in its initial rest position in which the needle 664 projects sealingly through the piston 662.

The partition 661 includes a central orifice 665 which is normally sealed by a rubber plug 666. The rubber plug 666 is in axial alignment with the needle 664 and with a membrane seal 667 forming part of the cylindrical formation 657 and normally separating the chamber 656 from the space 659 within cell 658.

The piston 662 is biassed in a direction towards the partition 661 by means of a coil spring 668 and the piston is restrained against axial movement by means of a catch 669 which is releasable by rotation of the cap 651 in a manner described below.

The hollow needle 664 has a side hole 670 which in the rest position shown in FIG. 29 is located above the piston 662 so as to be outside of the drug reservoir 660. The piston is provided with upper and lower sliding seals 710,711 respectively which "bracket" the side hole 670 and prevent entry of air.

The needle 664 also has an indentation 671 located intermediate the side hole 670 and the needle tip 672.

Rotation of the piston 662 relative to the base portion 652 is prevented by means of a locating pin 673 which is received in a cooperating recess 674 of the piston.

The cell 658 is evacuated to have a partial vacuum of 200 mm of mercury.

The apparatus is prepared for use by removing a protective film to expose an adhesive coated disc portion 654, the cell 658 being evacuated and the drug reservoir 660 being initially empty.

In use, the housing 653 is attached to the skin of the user such that the disc portion 654 is adhesively sealed to an annular area of skin 693 peripheral to a treatment site 696. Central aperture 655 is thereby sealed against ingress of air which thereby closes the chamber 656. Suction is applied at the treatment site 696 by actuation of the cap 651 so as to advance the needle 664 through both the rubber plug 666 and the membrane seal 667. The membrane seal 667 is formed of a frangible material which fractures and provides for the passage of air between the space 659 and the chamber 656 thereby reducing the pressure within the chamber. The rubber plug 666 maintains sealing engagement with the needle 664 so that no air enters the space 659 from the reservoir 660. Air cannot enter the chamber 656 through the needle 664 since the side hole 670 remains sealed by the seals 610,611.

A partial vacuum is maintained within the closed compartment constituted by the space 659 and the chamber 656 during a blister forming period, the ingress of air being prevented by an adhesive seal between the disc portion 654 and the annular portion of skin 693.

Figure 22:
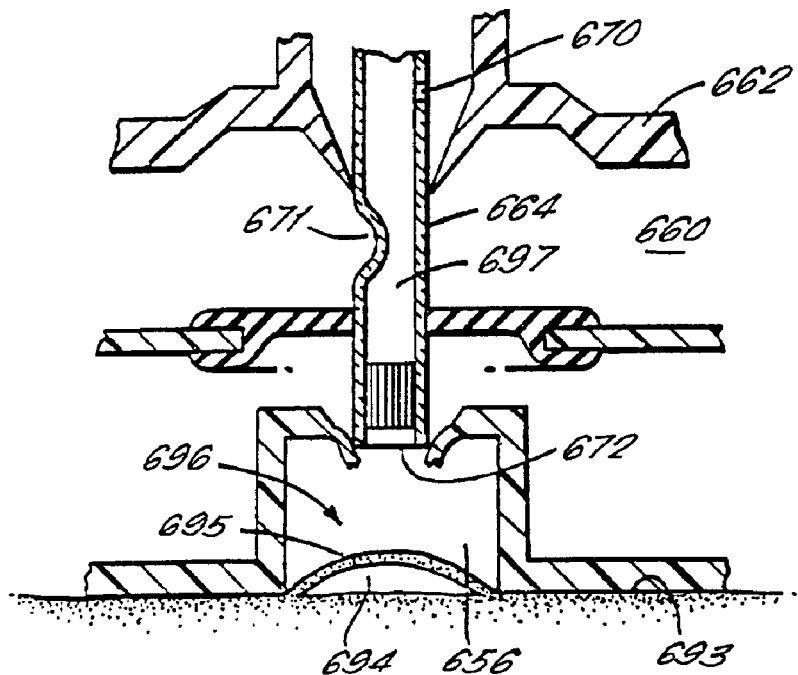
FIG. 22 is a sectioned elevation of the apparatus of FIG. 21 showing the actuation of suction means to apply partial vacuum to the skin.

The formation of a blister is illustrated in FIG. 22 which shows the position of the needle during the blister forming period. The blister consists of a raised portion of epidermis 695 which is 'delaminated' from the dermis 694 to which it is normally attached.

Figure 23:
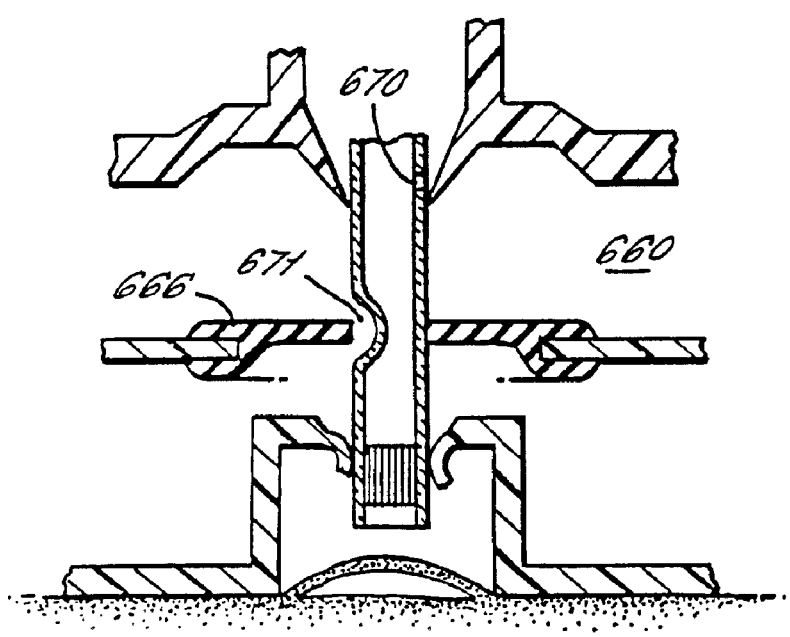
FIG. 23 is a sectioned elevation of the apparatus of FIGS. 21 and 22 showing the release of partial vacuum following formation of a skin blister.

Once a blister has been formed after a period of two hours a further rotational movement of the cap 651 is required to further advance the needle 664 to the venting position shown in FIG. 23 in which the indentation 671 comes into registration with the rubber plug 666 thereby allowing air from the reservoir 660 to enter the space 659 to restore atmospheric pressure.

At this stage a quantity of drug is inserted into the reservoir 660 through a drug insertion port 675 of the type shown in FIG. 28. Although not shown in FIG. 21 the insertion port 675 is located so as to provide a means of injecting liquid drug through the housing into the reservoir 660.

The drug insertion port 675 comprises a duct 676 communicating with the reservoir 660 and closed by a self-healing rubber bung 677 through which a syringe needle is insertable.

After filling the reservoir 660 with a liquid drug a further movement of the actuator cap 651 rotates the cap to a position in which the side hole 670 is located within the reservoir 660 and at the same time the catch 669 operates to release the piston 662. Under the action of the spring 668 the piston 662 pressurises liquid within the reservoir 660 which flows into the needle 664 through the hole 670 and emerges from the needle tip 672 into the chamber 656. By this further advancement of the needle the blister 678 is ruptured so that drug within the chamber 656 comes into contact with the exposed dermis 679 so that transdermal delivery of the drug is commenced.

As shown in FIG. 24 the needle 664 includes a microporous filter 680 adjacent the needle tip 672 by means of which the flow of liquid into the chamber 650 is restricted. This slows the rate of release of drug into the chamber 656 and ensures a gradual release of drug at a predetermined rate.

The housing 653 is held in situ for a period during which transdermal delivery proceeds and this period may extend to four days by which time the self-healing of the epidermis will begin to provide a barrier preventing direct access to the dermis.

Figure 25:
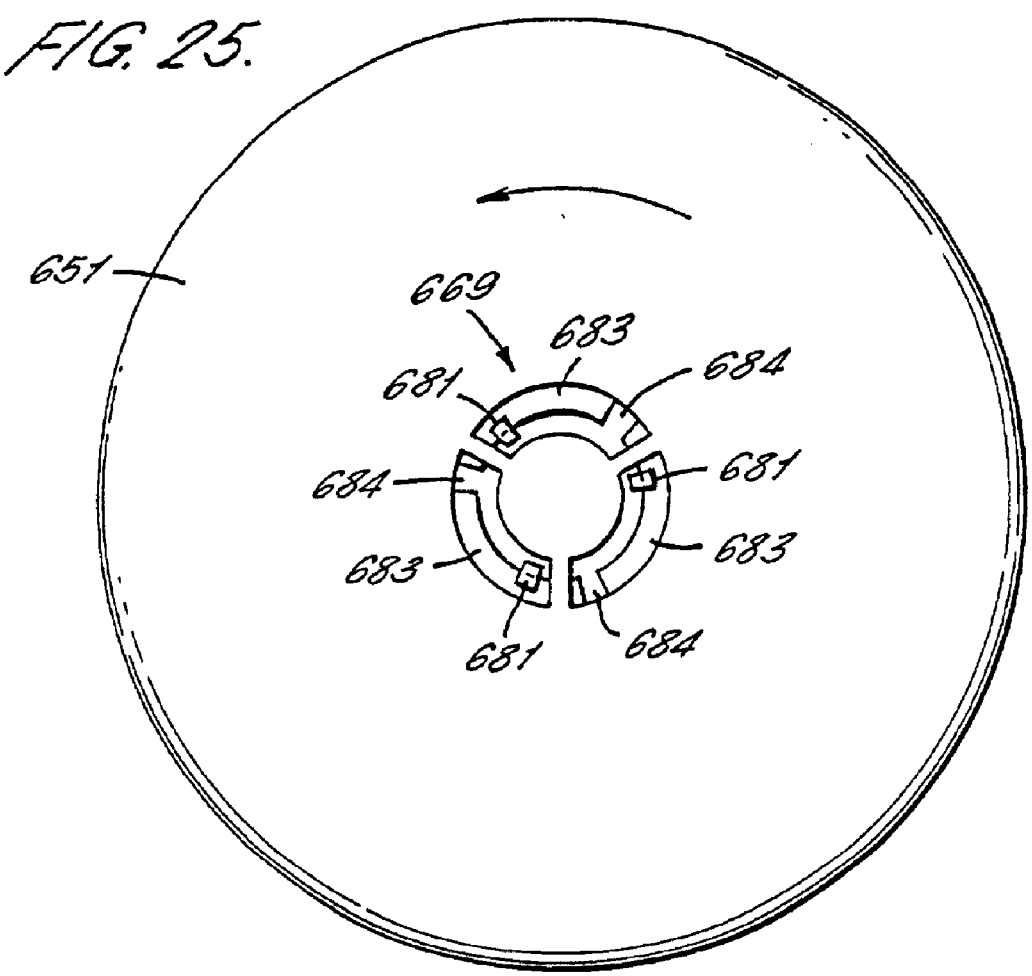
FIG. 25 is a plan view of the apparatus of FIGS. 21 to 24.

The construction of the catch 669 is illustrated in FIG. 25 which shows three circumferentially spaced feet 681 which are connected to the piston 662 by legs 682 such that the feet normally engage a supporting annular track 683 attached to the cap 651. The track 683 is provided with cut-outs 684 into which the feet 681 fall to release the catch 669 when the cap is rotated to its final position.

During rotation of the cap 651 relative to the base portion 652 the cap is advanced axially by screw action. In order to prevent the piston 662 advancing until released by the catch 669 the track 683 is ramped to provide a compensating axial movement of the piston relative to the cap so that the piston remains stationary relative to the base portion 652.

Figure 26:
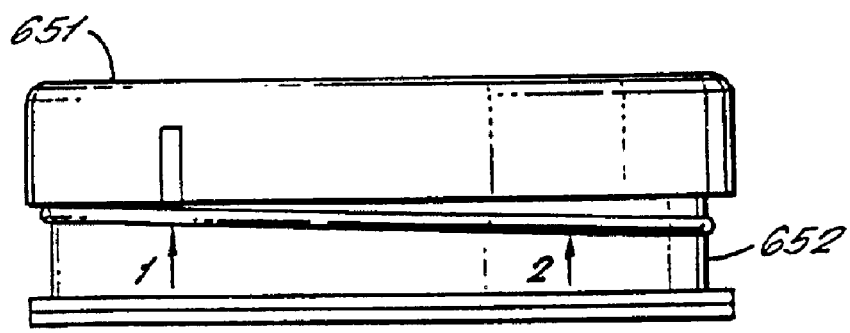
FIG. 26 is a side elevation of the apparatus of FIGS. 21 to 25.

Rotation of the cap 151 relative to the base portion 652 is stepped by use of suitable snap fitting detents and corresponding recesses (not shown) on the cap and base portion respectively. As shown in FIG. 26, suitable markings are provided on the cap 651 and base portion 652 to indicate the sequential steps of rotation.

The drug insertion port 675 may be replaced by a drug filling port 685 of the type shown in FIG. 29 in which a duct 686 is normally closed by a hinged snap fitting closure 687. Drug is therefore introduced into the reservoir 660 by opening the closure 687, pouring the drug in and replacing the closure.

The space 659 may be provided with a partial vacuum at manufacture or alternatively the partial vacuum within the space 659 may be produced immediately before use by withdrawing air through a suction port 688 of the type shown in FIG. 28. Suction port 688 comprises a duct 689 communicating with the space 659 via a non-return valve 690, the duct 689 being defined by a Luer connector 691 into which the hub of a syringe can be sealingly inserted. Suction created by reverse actuation of the syringe will thereby withdraw air through the non-return valve 690 from the space 659 to create a partial vacuum. The syringe is withdrawn from the connector 691 and the cell 658 is then sealed automatically by action of the valve 690 before attachment of the housing 653 to the skin.

The housing 653 may be attached to the skin of an arm or leg in the manner shown in FIG. 29 where an adhesive strip 700 extends around the limb 701. Alternatively as shown in FIG. 30 an annular adhesive film 702 may attach the housing 653 to a localised area of skin thereby contributing to the airtight seal formed between the disc portion 654 and the skin but without any further means of holding the housing in situ.

Figure 30:
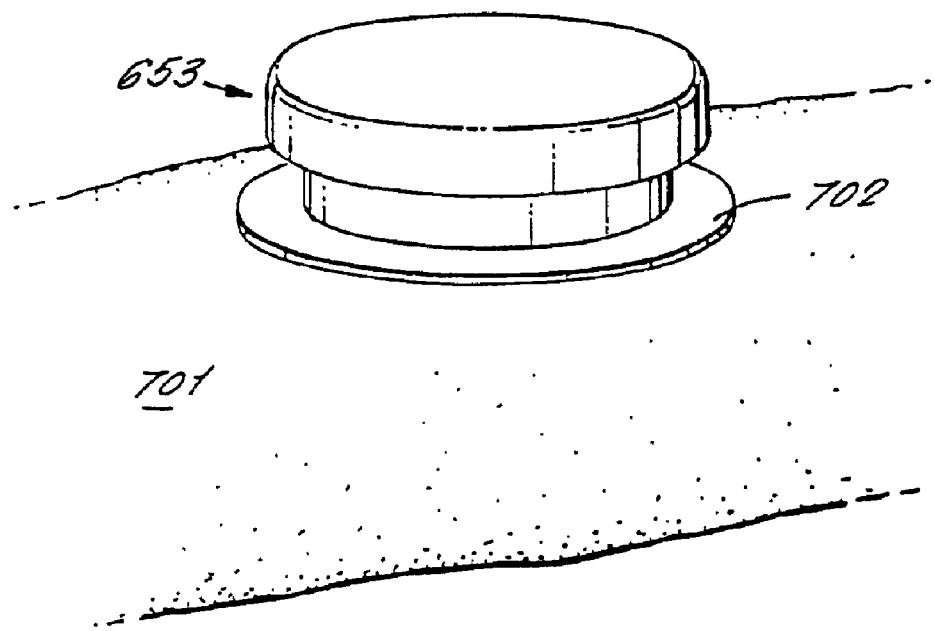
FIG. 30 is a perspective view of the apparatus of FIGS. 21 to 28 showing attachment to an arm of a patient.
Figure 31:
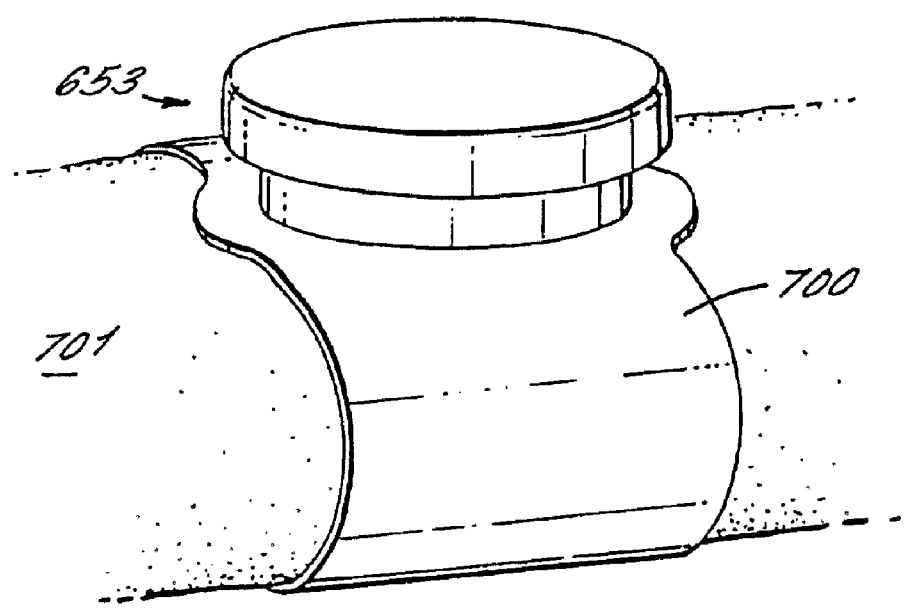
FIG. 31 is a perspective view of the apparatus of FIGS. 21 to 28 showing an alternative means of attachment to an arm of a patient.
Figure 32:
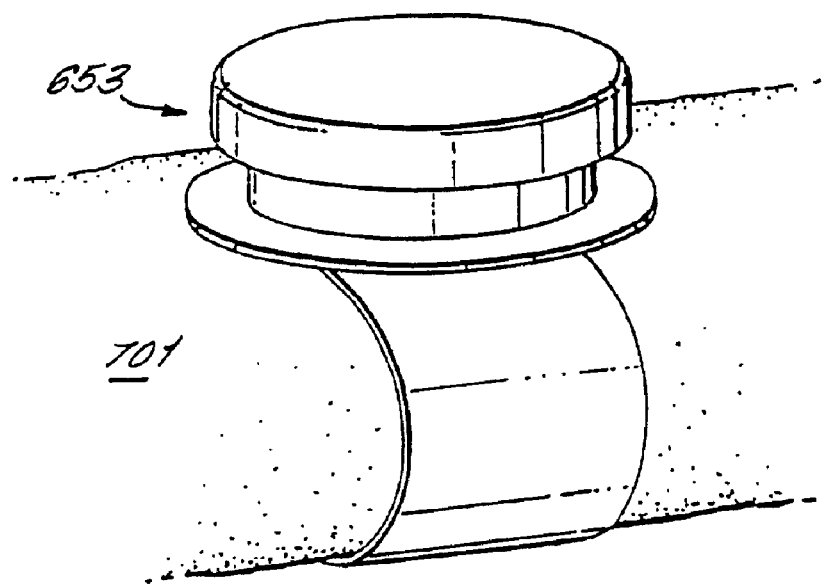
FIG. 32 is a perspective view of the apparatus of FIGS. 21 to 28 showing a further alternative means of attachment to the arm of a patient.
Figure 33:
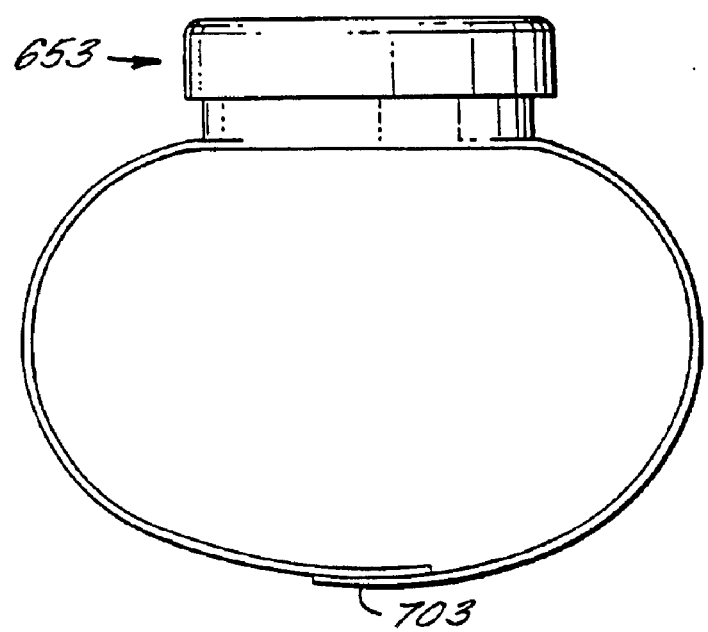
FIG. 33 is an elevation of the apparatus of FIG. 32.

As shown in FIG. 32 the arrangement of FIG. 30 can be supplemented by the addition of a strap fastened using a hook-loop fastener 703 as illustrated in FIG. 33.

In the above embodiments the adhesive used in contact with the skin may be of a hydrocolloidal type composed of pectin and gelatine or may alternatively be composed of acrylic or silicon. In each case the apparatus may be supplied with the adhesive covered in a protective sheet which also seals the aperture formed in the contact surface and the entire assembly can be sterilised in readiness for use.

The fifth apparatus 560 of FIGS. 7 and 8 may be provided with alternative means of expanding the chamber 563. For example a screw type arrangement or piston arrangement may be used to expand the enclosed chamber.

The contact surface may be sealed to the skin other than by the use of adhesive if required. For example the contact surface may be provided with projecting ribs which sealingly engage the skin surface and in such an arrangement the apparatus should be held firmly in place for example by straps.

Apparatus in accordance with the present invention may be provided with more than one evacuated cell to allow the partial vacuum to be re-established for example for the purpose of removing a self-healed epidermal barrier or to remove by suction any blister fluid within the chamber.

It may be desirable to provide apparatus in which the contact surface is interchangeable to provide apertures of different size.

The size of the de-epithelialised area of skin may also be stretched by applying stretching means to the surrounding skin.

In the examples referred to above the aperture size of 5 mm may be varied typically in the range 1 mm to 10 mm.

The drug may be applied in a form producing slow release, for instance by reversible binding in absorbent biodegradable starch particles, polymer(s), in non-biodegradable polysaccharide spheres, or in microcapsules consisting for instance partly of lipids or polymers of different types which may break or disintegrate slowly in biological fluids.

The drug may be applied in so-called pro-drug form, allowing it to pass through the tissue into the blood with minimal break-down (this being an important aspect in peptide delivery).

The re-epithelialisation of the drug delivery site can be delayed for instance by applying a steroid drug in addition to the therapeutic agent. Other means, for instance addition of antibodies to epithelial cells, may be used for the same purpose. The apparatus could be pre-loaded with such an agent, it could be added to the drug solution or taken by other routes.

The apparatus of FIGS. 1 to 6, 14 to 20 may be provided with a suction valve of the type described with reference to FIG. 28.

The apparatus of FIGS. 17 to 20 and of FIGS. 21 to 26 may be modified to include an expansion means of the type described with reference to FIG. 7. The apparatus may also optionally include a valve for interrupting the delivery of drug in use.

In the above embodiments reference is made to the delivery of drugs in liquid form. The apparatus may also be used to deliver gels and creams with suitable modification where appropriate.

FIG. 34 shows a further device 1 for use in the transdermal delivery of a liquid drug in contact with a de-epithelialised area of skin and for initially de-epithelialising the skin by formation and subsequent disruption of a suction blister.

The device 1 comprises a housing 2 consisting of a base 3 secured in contact with a patient's skin 4 and having a rotatable portion 5. The base 3 is disc shaped and the rotatable portion 5 generally cylindrical and coupled to the base so as to be rotatable relative to the base about its cylindrical axis in continuous sliding contact with the base.

A circular aperture 6 is defined in the base 3 at a location eccentric relative to the cylindrical axis of the rotatable portion 5. In the rest position of the device shown in FIG. 34, a cylindrical access port 7 defined in the rotatable portion 5 is aligned in communication with the aperture 6 such that a circular area of skin 8 is accessible through the device 1.

A suction cup 9 is located in the access port 7 and has a flared lip 10 of greater diameter than the port 7 such that the suction cup is captively retained. The base 3 is recessed peripherally of the aperture 6 to accommodate the lip 10. The internal surfaces of the cup 9 are coated with acrylic adhesive so that, once a suction blister is formed in the cup, the surface of the blister will adhere to the cup, thereby maintaining the blister in an elevated position. This will tend to prevent collapse of the blister in the event of accidental rupture.

The rotatable portion 5 also accommodates a reservoir 11 containing a liquid drug, the reservoir 11 being isolated from the access port 7 in the position shown in FIG. 34.

The suction cup 9 has a female connector 13 which is engagable with a male connector 14 of a suction tube 15 via which suction can be applied in use to a suction chamber 16 defined within the suction cup 9. In FIG. 34, the device is shown in its rest position following the application of suction within the chamber 16 for a period sufficient to result in the formation of a suction blister 17, following which the male and female connectors 13 and 14 have been disconnected from one another to admit air at ambient pressure to the chamber 16.

The device 1 also includes a blade 18 which extends radially with respect to the cylindrical axis of the rotatable portion 5 and which is movable by rotation about the cylindrical axis in a plane defined by the interface between the base 3 and the rotatable portion 5.

In FIG. 35 the operation of the blade 18 is illustrated in that it has been moved arcuately so as to cut through the suction cup 9 at a location which is intermediate the roof of the suction blister 17 and the aperture 6. By this cutting action, the suction cup 9 is severed into a captive portion 19 extending through the base 3 and a removable portion 20 extending through the rotatable portion 5 and to which the roof 21 of suction blister 17 remains adhered.

By withdrawing the removable portion 20 from the access port 7, the roof 21 may thereby be disposed of. Since the removable portion 20 is severed at the interface between the base 3 and the rotatable portion 5, the severing action of the blade 18 thereby allows the rotatable portion 5 to be subsequently movable by rotation relative to the base 3 whereas previously the presence of the suction cup extending through the aperture 6 and access port 7 prevented such relative rotational movement about the cylindrical axis.

The reservoir 11 has an outlet port 22 which in the rest position of the rotatable portion 5 as shown in FIGS. 34 and 35 is closed by an upper surface 23 of the base 3, a continuous O-ring seal 24 being interposed between the surface 23 and the rotatable portion 5 to prevent peripheral leakage from the outlet port 22. Following the severing of the suction cup 9, the rotatable portion 5 is rotated into a second position shown in FIG. 36 in which the outlet port 22 is brought into registration with the aperture 6, the location of the outlet port 22 being spaced radially from the cylindrical axis of the rotatable portion 5 about which it is rotated.

The O-ring seal 24 is maintained in a fixed position relative to the rotatable portion 5 so that in this second position it forms a peripheral barrier between the rotatable portion 5 and the upper surface 23 of the base 3. The drug 12 within the reservoir 11 then enters the chamber 16 and comes into contact with the area of skin 8 which has been de-epithelialised following removal of the suction blister 17. The device 1 is retained in this second position during a drug delivery phase of operation in which the drug is absorbed into the patient.

On completion of this phase, the rotatable portion 5 is again rotated and moved into a third position shown in FIG. 37. In this third position, the outlet port 22 of the reservoir 11 is again closed by the upper surface 23, assisted by the sealing action of the O-ring seal 24. A second O-ring seal 25 is brought into peripheral sealing engagement between the upper surface 23 and the rotatable portion 5 at a location peripheral to the aperture 6 thereby providing an air tight seal to the chamber 16.

The rotatable portion 5 may subsequently be returned to the second position should further drug delivery be required or the device 1 may be removed from the patient on completion of the procedure.

The above FIGS. 34 to 37 are schematic in nature and serve to illustrate the function of the above mentioned elements. The detailed construction of these elements will now be described in the context of a specific embodiment of the invention.

Figure 38:
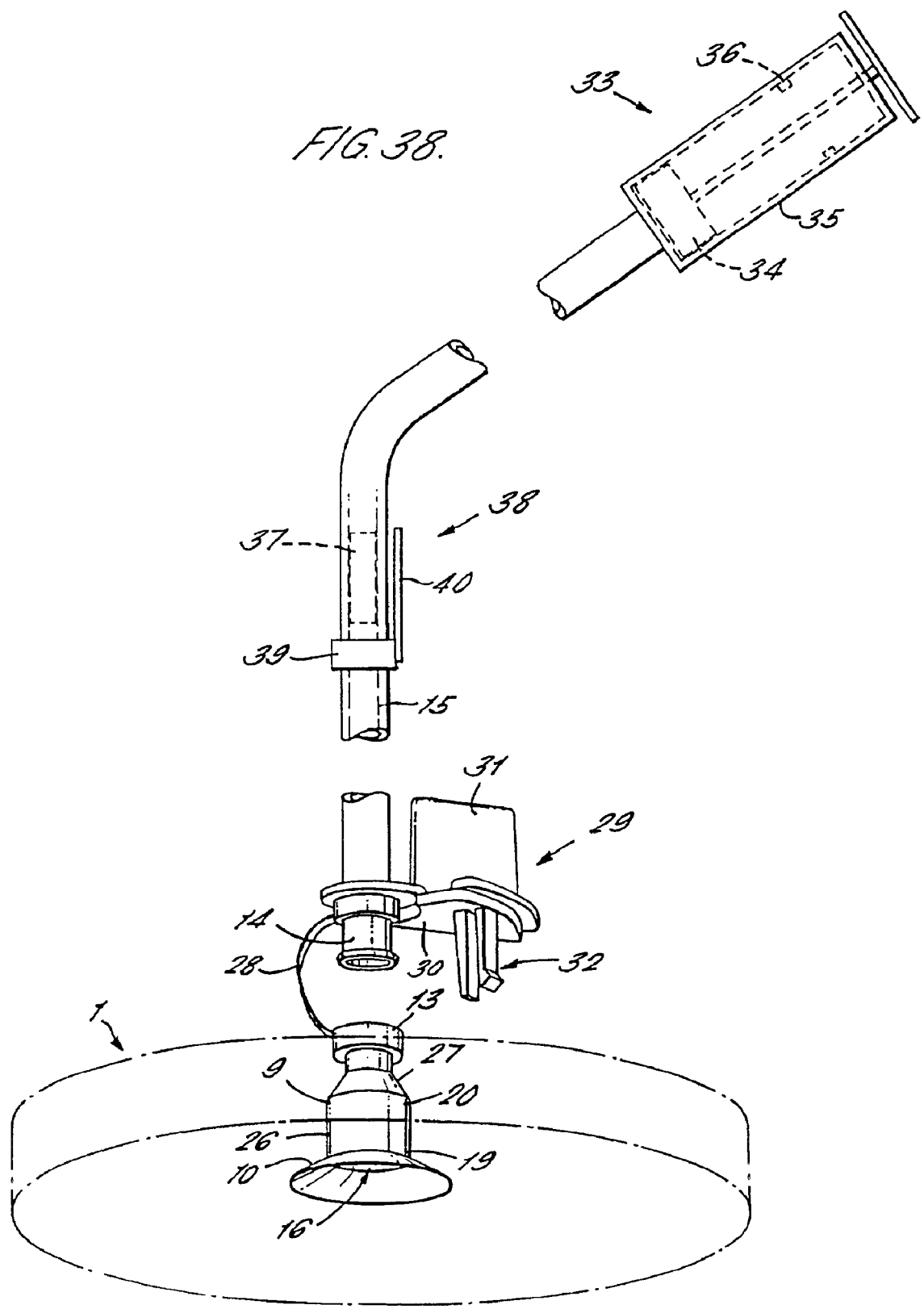
FIG. 38 is a perspective view of the suction cup and arming device of the device of FIGS. 34 to 37.

In FIG. 38 the suction cup 9 is shown to comprise a cylindrical portion 26 defining the chamber 16 and which in use is severed radially by action of the blade 18 into captive and removable portions 19 and 20. The internal surfaces of the suction cup 9 are coated with an acrylic adhesive incorporated with random oriented polyester fibres.

The removable portion 20 terminates in the female connector 13 to which it is connected by a frustoconical tapered portion 27. The male connector 14 is connected by a flexible web 28 to the female connector 13 such that when disconnected from one another they are retained in loose association. An arming device 29 is connected to the male connector 14 and consists of a plate 30 through which the suction tube 15 passes, the plate being formed integrally with an outwardly projecting handle 31 and an oppositely projecting bifurcated arming pin 32. The arming device 29 is shaped such that it must be inserted within the rotatable portion 5 in order for the male and female connectors 14 and 13 to be engaged, the presence of the inserted arming pin 32 being arranged to prevent movement of the blade 18 from its initial position as shown in FIG. 34. This arrangement thereby ensures that the blade 18 cannot be moved until the arming device 29 has been disengaged from the rotatable portion 5 and this disengagement also necessitates disengagement of the male and female connectors 14 and 13 so that suction can no longer be maintained in the chamber 16. This is a safety feature of the device 1 which is intended to avoid cutting the suction blister 17 while there is any suction within the chamber 16 which could displace the underlying dermis into a position in which it extends into the chamber sufficiently to be damaged by the blade.

The suction tube 15 is connected to a syringe 33 comprising a piston 34 slidable within a cylinder 35 and spring biassed into the position shown in FIG. 38 in which the syringe volume is a minimum. The syringe is provided with a locking mechanism 36 enabling the piston 34 to be held in a withdrawn position corresponding to maximum syringe volume so that suction can be applied to the chamber 16 by engaging the male and female connectors 14 and 13 and then withdrawing the piston and locking the piston in place by means of the locking mechanism.

The suction tube 15 is formed of a transparent and flexible plastics material and contains a slug of liquid 37 forming part of an indicator 38.

The indicator 38 comprises a clamping ring 39 which is a tight fit on the external surface of the suction tube 15 but can be adjusted in position along the length of the tube so as to bring into registration with the slug of liquid 37 a linear scale 40. When suction is initially applied to the chamber 16 by action of the syringe 33, the position of the slug of liquid 37 will move due to displacement of air along the tube 15 to a new position and the operator using the device 1 at this time adjusts the position of the clamping ring 39 such that the end of the slug of liquid 37 is aligned with a zero marking on the scale 40. Suction is maintained with the chamber 16 during a blister forming period in which the suction blister 17 will progressively form and grow in size until it extends into the cylindrical portion 26. In doing so the blister 17 will displace air within the tube 15 and consequently the slug of liquid 37 will be linearly displaced relative to the scale 40. The scale 40 is calibrated such that the operator is able to determine the extent of displacement of the slug of liquid 37 corresponding to the blister 17 being fully formed to a predetermined level at which a predetermined volumetric displacement within the chamber 16 is achieved.

By visual inspection of the indicator 38 it is therefore possible for the operator to determine when the blister forming phase of operation is completed.

At this stage the operator will grip the handle 31 and pull the arming device 29 so as to withdraw the arming pin 32 and at the same time to disconnect the male connector 14 from the female connecter 17. Suction within the chamber 16 will then be lost.

Figure 39:
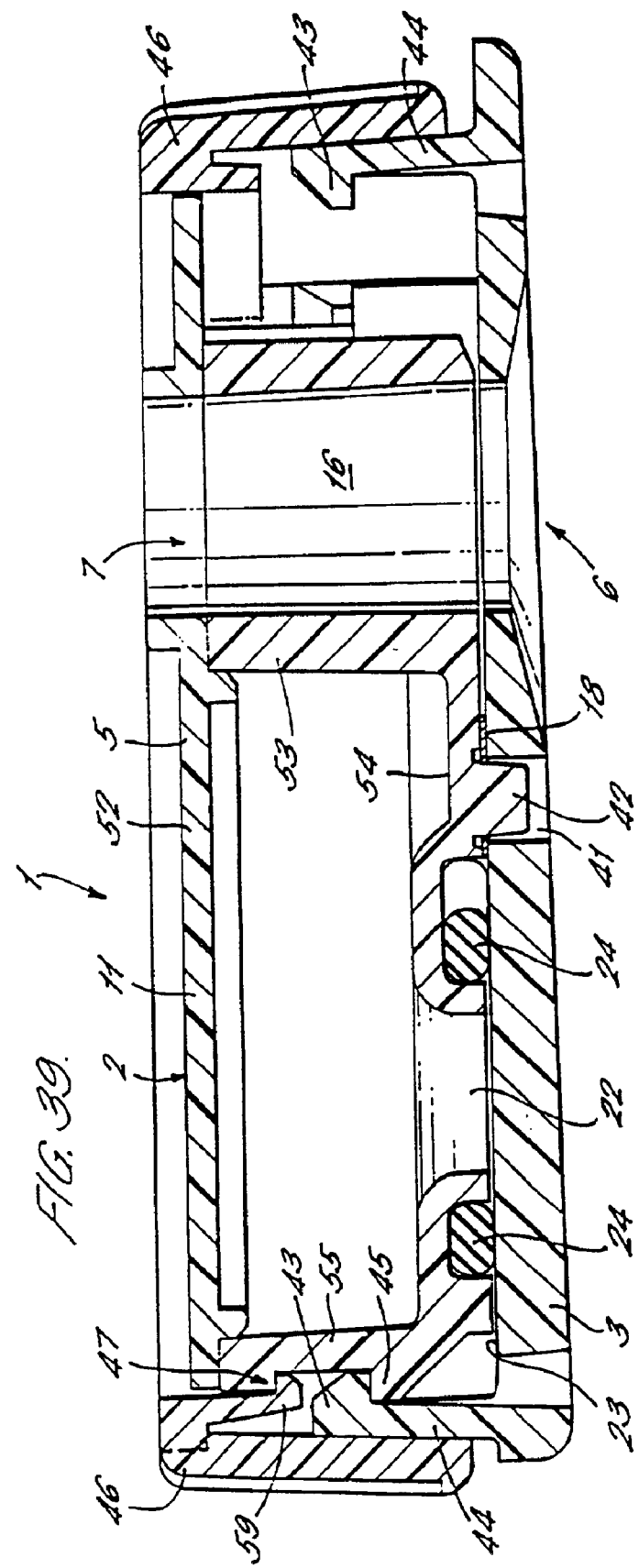
FIG. 39 is a sectional elevation of the device of FIGS. 34 to 38 with the suction cup removed.

FIG. 39 shows the device 1 in greater detail with the suction cup omitted for clarity. The base 3 has a central socket 41 in which an axially projecting pin formed integrally with the rotatable portion 5 is journaled thereby enabling the rotatable portion to be rotatable about its cylindrical axis relative to the base 3. The rotatable portion 5 is retained in axial abuttment with the base 3 by retaining flanges 43 which project radially inwardly from circumferentially spaced axial projections 44 formed integrally with the base 3.

The rotatable portion 5 is provided with a part annular rim 45 which projects radially outwardly so as to engage the projection 44.

An actuating ring 46 is mounted on the rotatable portion 5 and is captively retained by cooperating flange formations 44. The actuating ring 46 is capable of limited angular displacement relative to the rotatable portion 5 for the purpose of moving the blade 18 relative to the rotatable portion 5 and base 3 when the latter are locked together by the presence of the suction cup.

Figure 40:
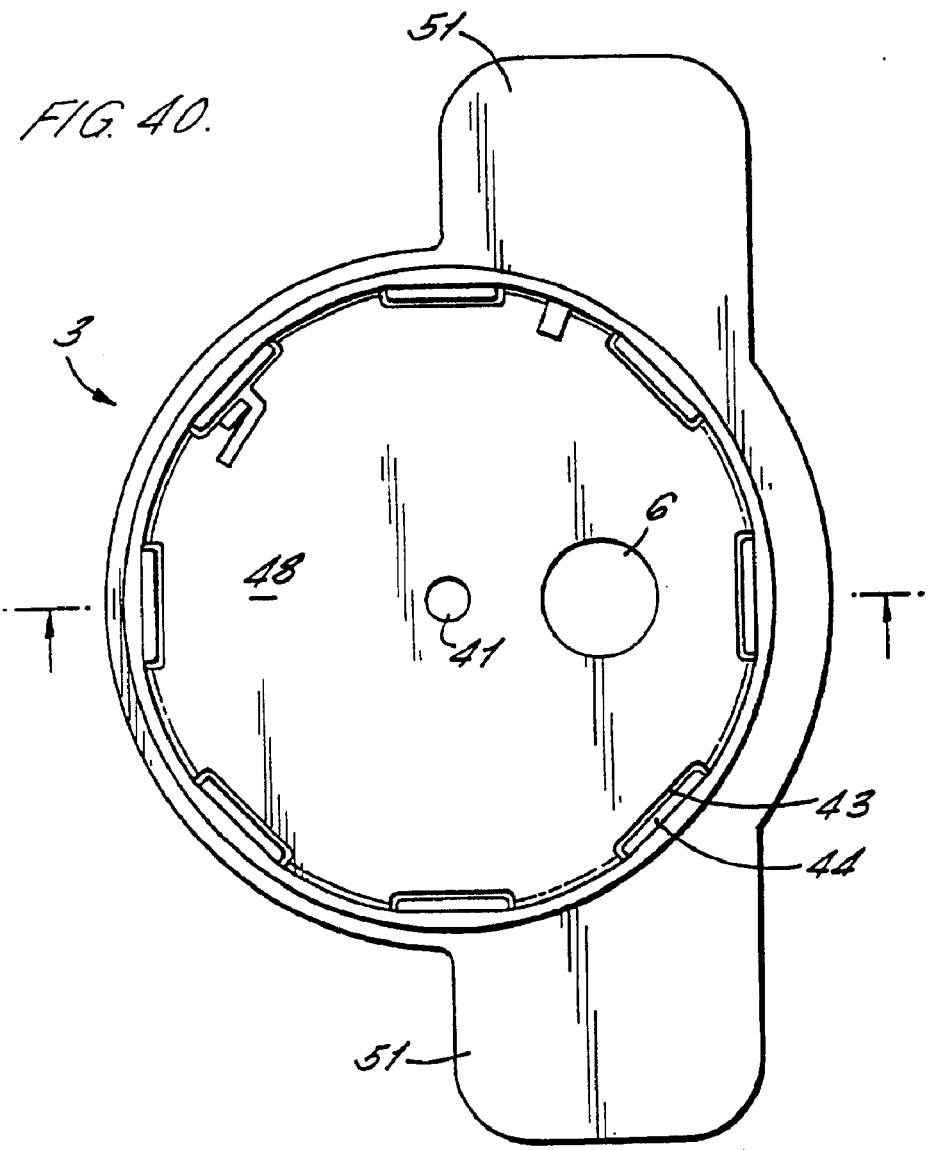
FIG. 40 is a plan view of a base of the device of FIGS. 34 to 39.
Figure 41:
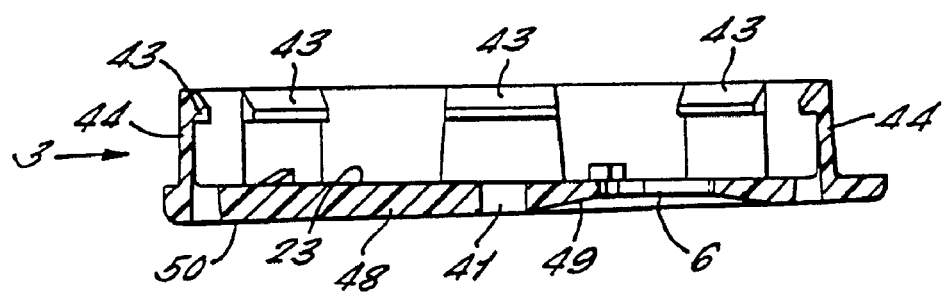
FIG. 41 is a sectional elevation of the base of FIG. 40.

The shape of the base 3 is shown more clearly in FIGS. 40 and 41. The base 3 comprises a disc 48 in which the socket 41 is centrally formed and the aperture 6 is eccentrically located. A tapered seat 49 surrounds the aperture 6 and is shaped to conform to the lip 10 of the suction cup so that when the suction cup is inserted in the aperture 6 the lip 10 remains flush with the underside 50 of the disc 48. The disc 48 is provided with laterally projecting wings 51 to assist in stably securing the disc to the patient's skin. The underside 50 comprises an adhesive layer enabling the disc 48 to be secured to the skin in a secure and air tight manner so that in use with the suction cup evacuated the patient's skin forms a sealed closure to the chamber 16.

Figure 42:
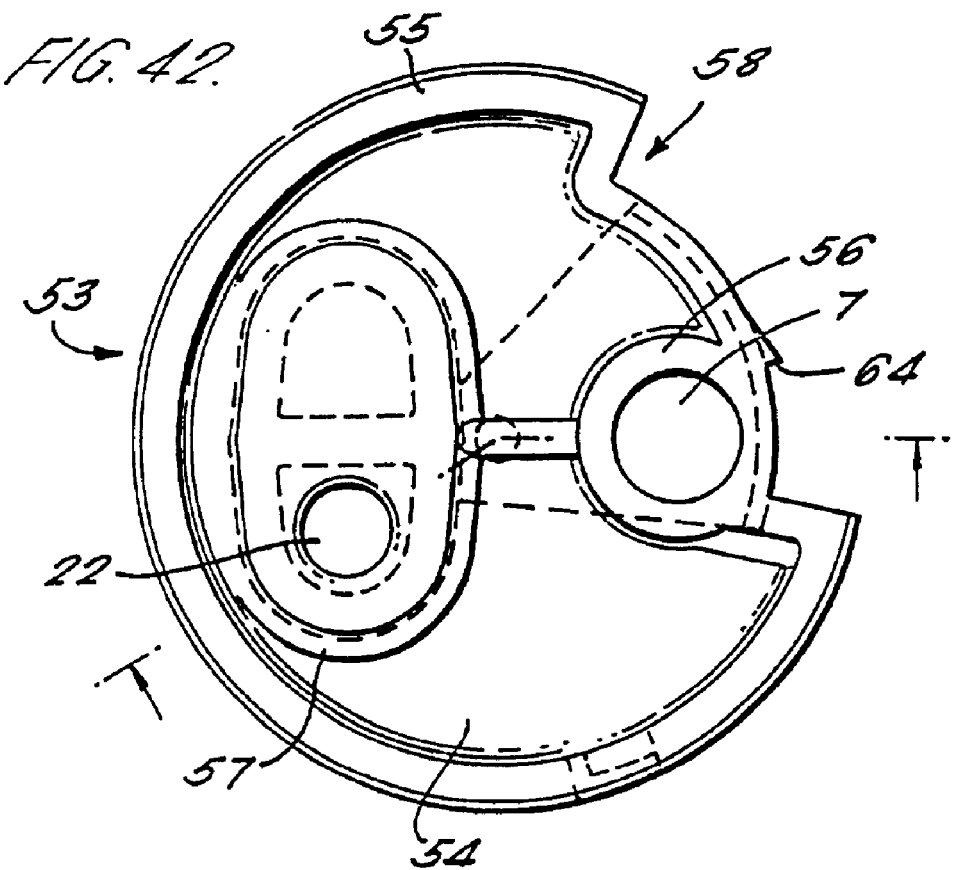
FIG. 42 is a plan view of a rotatable portion of the device of FIGS. 34 to 39.
Figure 43:
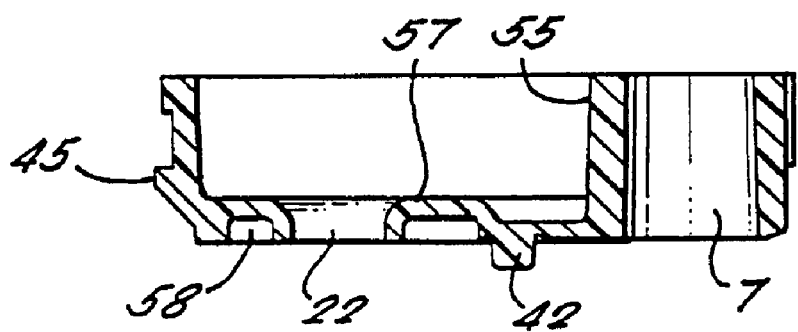
FIG. 43 is a sectional elevation of the rotatable portion of FIG. 42.

FIG. 42 shows the rotatable portion 5 in plan view omitting a top cover plate 52 shown in FIG. 39 which in the completed device is heat welded to a main body 53 of the rotatable portion 5 so as to close the reservoir 11. The main body 53 consists of a planar bottom 54 with an upstanding peripheral wall 55 which is part circular to define the rim 45 and includes a cylindrical wall portion 56 defining the access port 7.

The bottom 54 includes a raised figure of eight profile 57 which accommodates a recess 58 on the underside of the bottom 54 which receives integrally formed seals 24 and 25.

Figure 44:
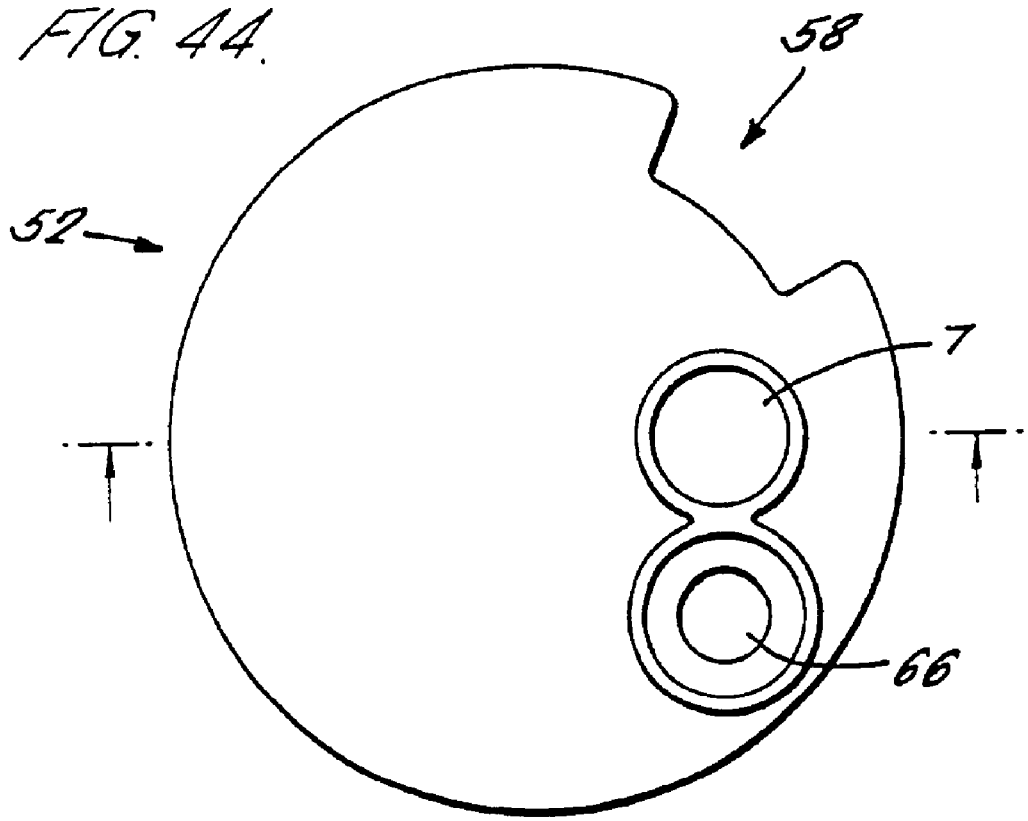
FIG. 44 is a plan view of a cover plate for the rotatable portion of FIGS. 42 and 43.
Figure 45:
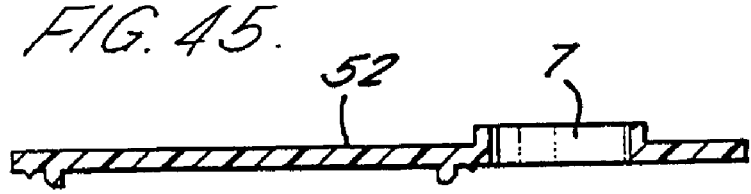
FIG. 45 is a sectional elevation of the cover plate of FIG. 44.

FIG. 44 shows the shape of the cover plate 52 which is that of a disc with a cut out 58 provided to allow insertion of the arming pin 32.

Figure 46:
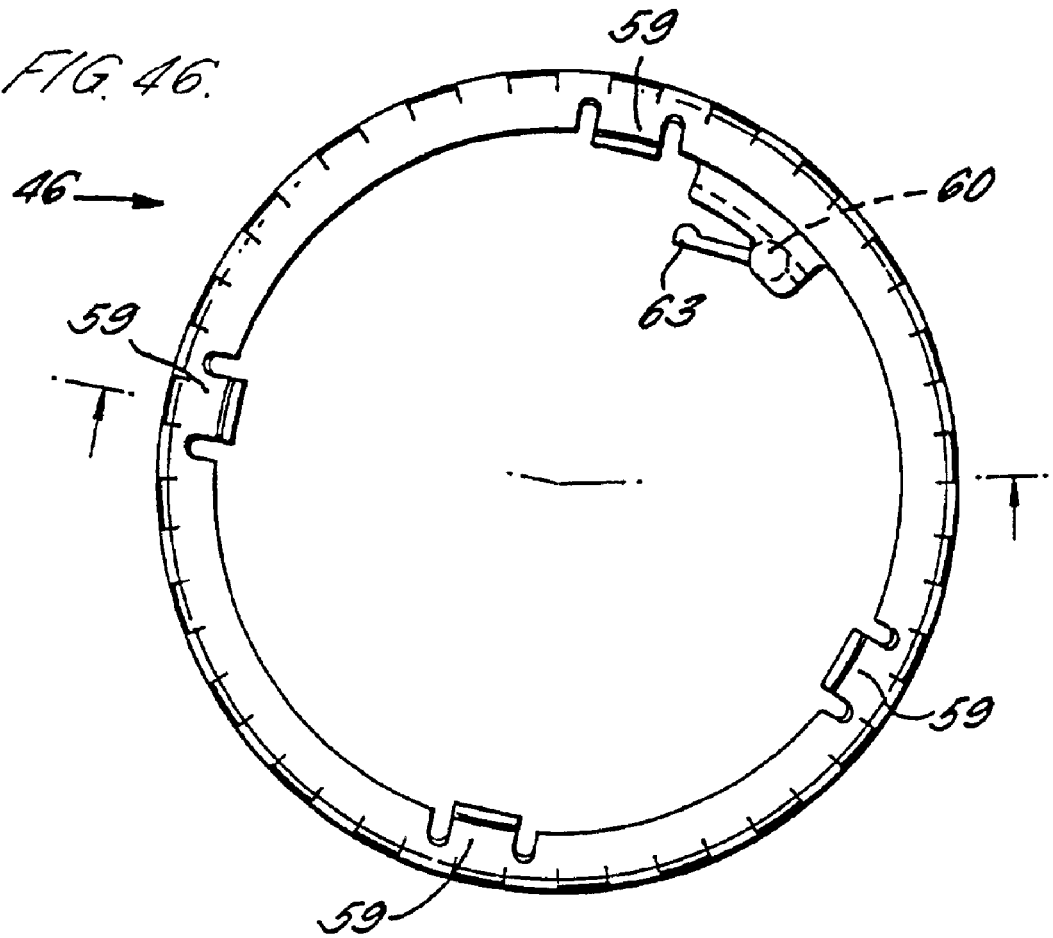
FIG. 46 is a plan view of an actuating ring of the device of FIGS. 34 to 39.
Figure 47:
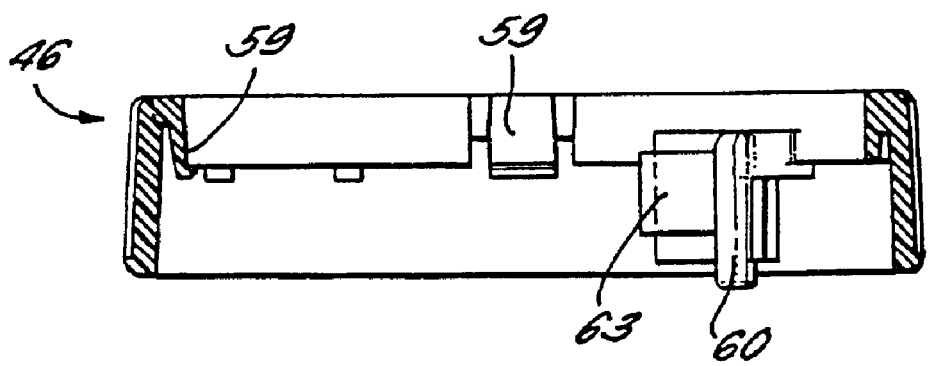
FIG. 47 is a sectional elevation of the actuating ring of FIG. 46.

FIGS. 46 and 47 show the actuating ring 46 which has four circumferentially spaced snap fit retaining flanges 59 forming part of the flange formations 47 and thereby securing the actuating ring to the rotatable portion 5.

Figure 48:
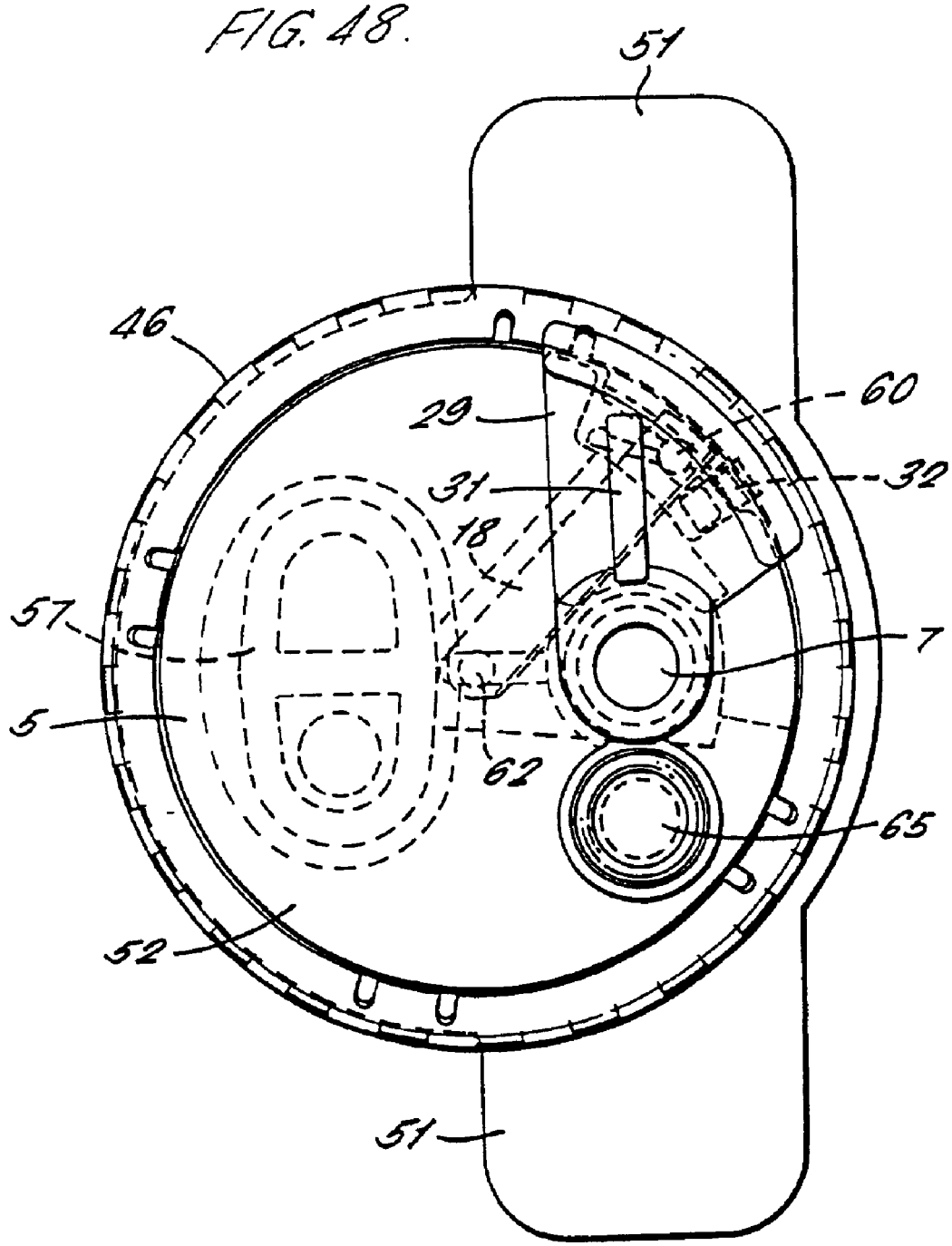
FIG. 48 is a plan view of the device of FIGS. 34 to 39 with the suction cup omitted and showing the device in a rest position prior to removal of the arming device.

As shown in FIG. 47 the actuating ring 46 includes a drive pin 60 which locates in a locating hole 61 at the outer radial extremity of the blade 18 as shown in FIG. 48. Rotation of the actuating ring relative to the rotatable portion 5 will thereby cause the blade 18 to rotate about an inner radial pivot 63 which is coaxial with the cylindrical axis of the rotatable portion 5.

A resilient detent 63 is also provided adjacent the drive pin 30 and projects radially inwardly in the manner of a ratchet so as to cooperate with a ramped stop 64 formed on the rotatable portion 5 as shown in FIG. 42. The detent 63 and stop 64 prevent reverse rotation of the actuating ring 46 relative to the rotatable portion 5 after completion of an initial stage of rotation between an initial position of the actuating ring (FIGS. 39, 48 & 49) and an actuated position (FIG. 50).

FIG. 48 shows the base 3 assembled with the rotatable portion 5 and the actuating ring 46 but with the suction cup not being shown.

The device 1 in FIG. 48 is shown with the blade 18 in its initial position and with the arming device 29 in place so that relative movement between the actuating ring 46 and the rotatable portion 5 is prevented by the presence of the arming pin 32.

Also shown in FIG. 48 is a plug 65 which closes a filling port 66 provided in the cover plate 52 to facilitate filling of the reservoir 11.

Figure 49:
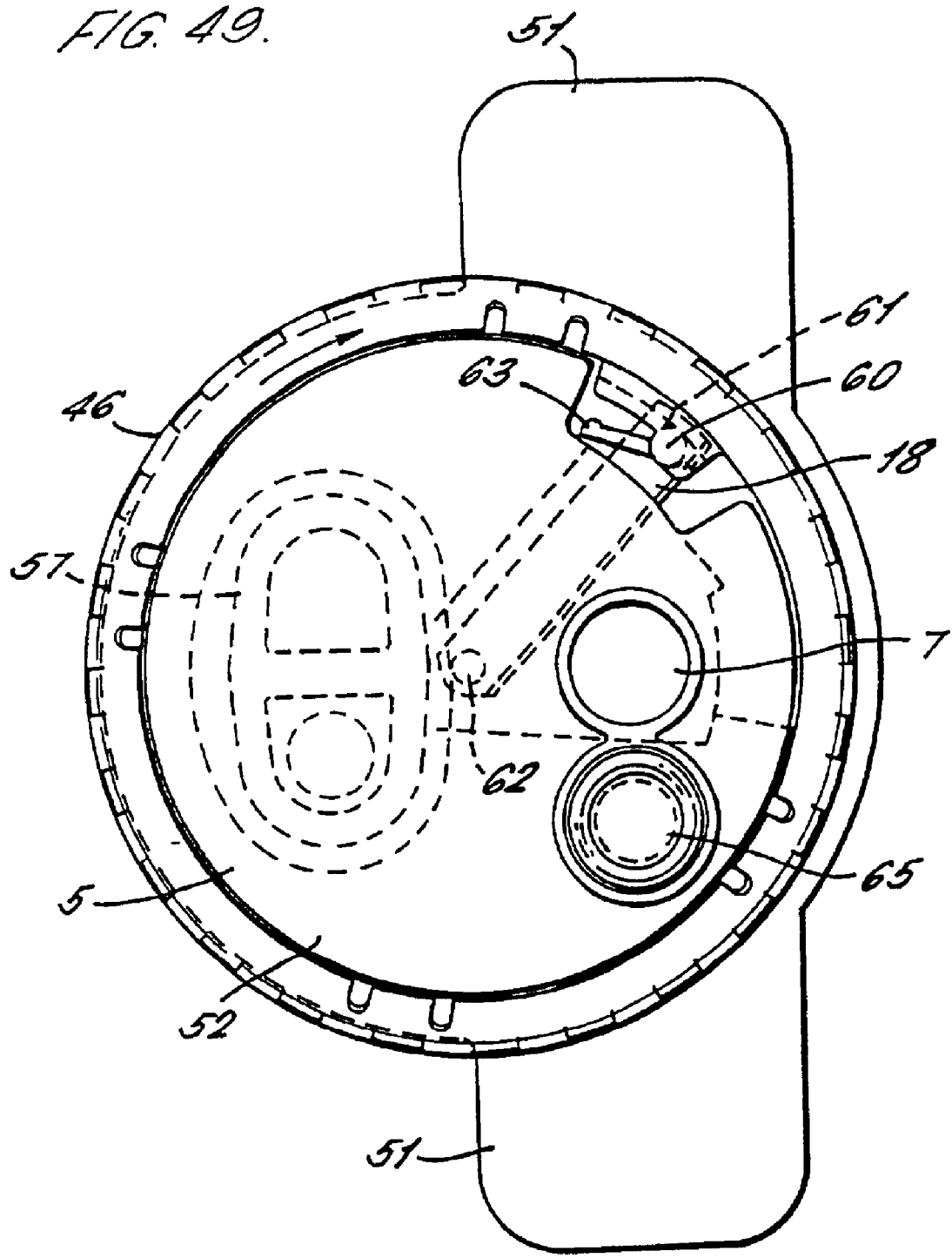
FIG. 49 is a plan view of the arrangement of FIG. 48 with the arming device removed.
Figure 50:
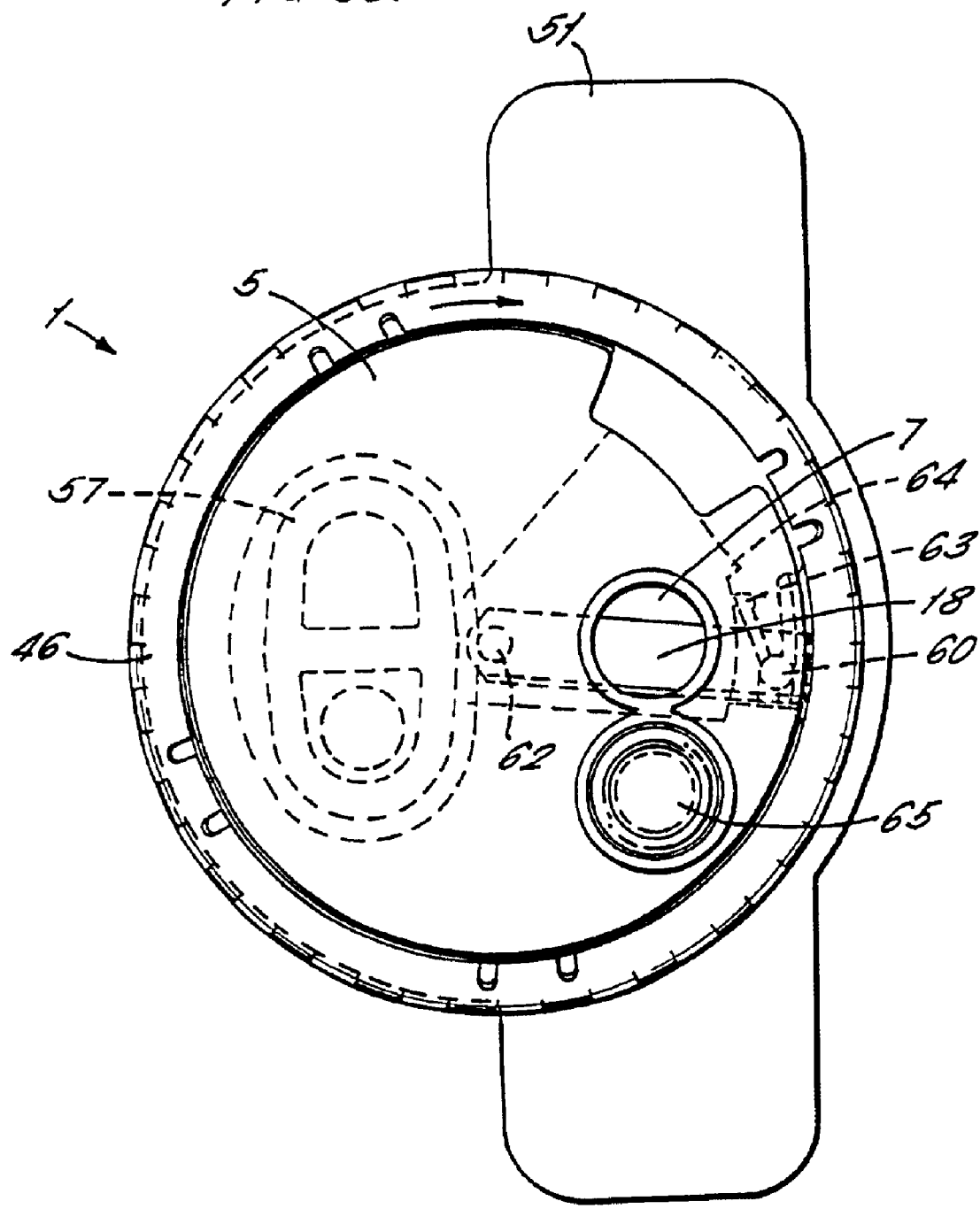
FIG. 50 is a plan view of the arrangement of FIG. 48 after rotation of the actuating ring to a position in which the blade is moved through the access port in which the suction cup is locatable.

FIG. 49 shows the device 1 after removal of the arming device 29, the pin 60 and detent 63 being thereby exposed in plan view.

FIG. 50 shows the device 1 after subsequent rotation of the actuating ring 46 relative to the rotatable portion 5 from the initial position to the actuated position corresponding to the actuated position by the blade indicated schematically in FIG. 35. In this actuated position, the blade 18 is seen to have traversed the access port 7 and will therefore have severed the suction cup 9 and suction blister 17 (not shown in FIG. 50). In this actuated position the detent 63 can also be seen to have moved beyond the stop 64 and will subsequently prevent rotation of the actuating ring 46 relative to the rotatable portion 5.

Figure 51:
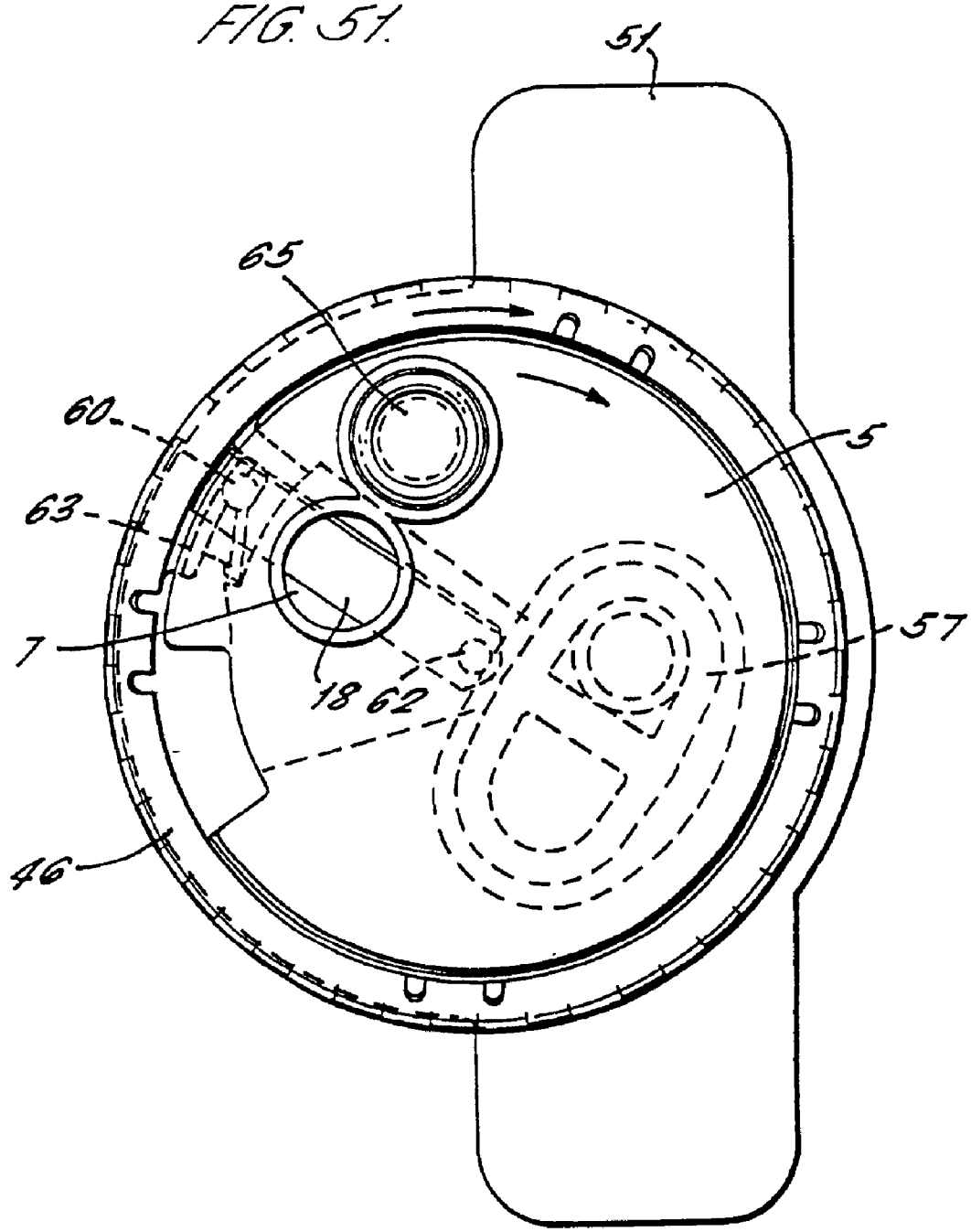
FIG. 51 is a plan view of the arrangement of FIG. 48 showing a further position in which the rotatable portion has been rotated to bring an outlet port of the reservoir into registration with the access port.

FIG. 51 illustrates further clockwise rotation of the actuating ring 46 in unison with the rotatable portion 5 relative to the base 3 into the second position of the rotatable portion represented in FIG. 36. In this second position the outlet port 22 of the reservoir 11 is brought into registration with the aperture 6 and the contents of the reservoir 11 enter the chamber 16. Absorption of the liquid drug 12 then occurs during a transdermal delivery phase of operation of the device.

Figure 52:
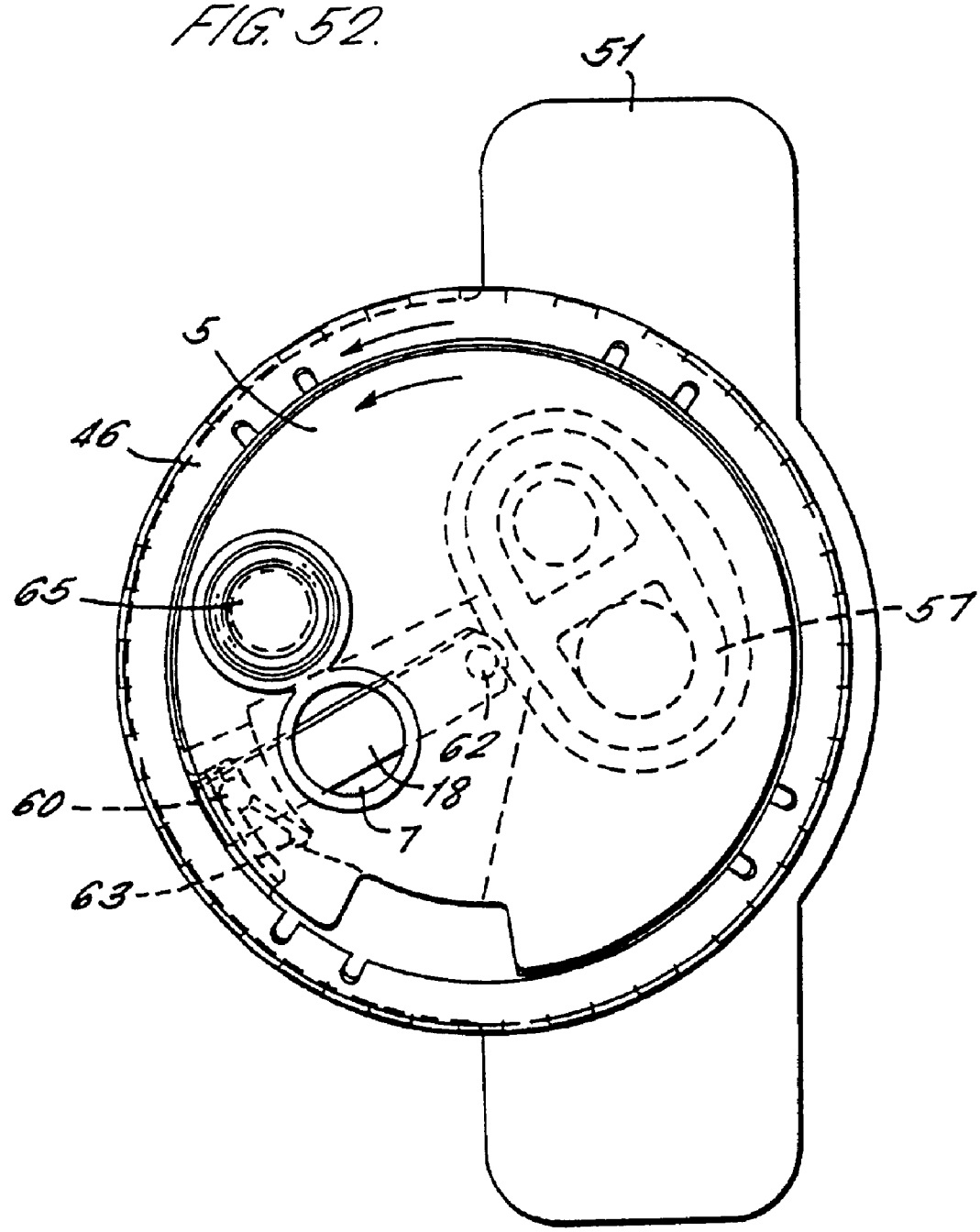
FIG. 52 is a plan view of the arrangement of FIG. 48 following further movement of the rotatable portion to a position in which the access port is sealed.

FIG. 52 shows the final stage of operation in which reverse (anti-clockwise) rotation of the actuating ring 46 in unison with the rotatable portion 5 relative to the base 3 moves the rotatable portion into the third position represented in FIG. 37. In this position the outlet port 22 of the reservoir 11 is closed and the ingress of air is prevented by the second O-ring seal 25 cooperating between the upper surface 23 of the base 3 and the bottom 54 of the rotatable portion 5.

Figure 53:
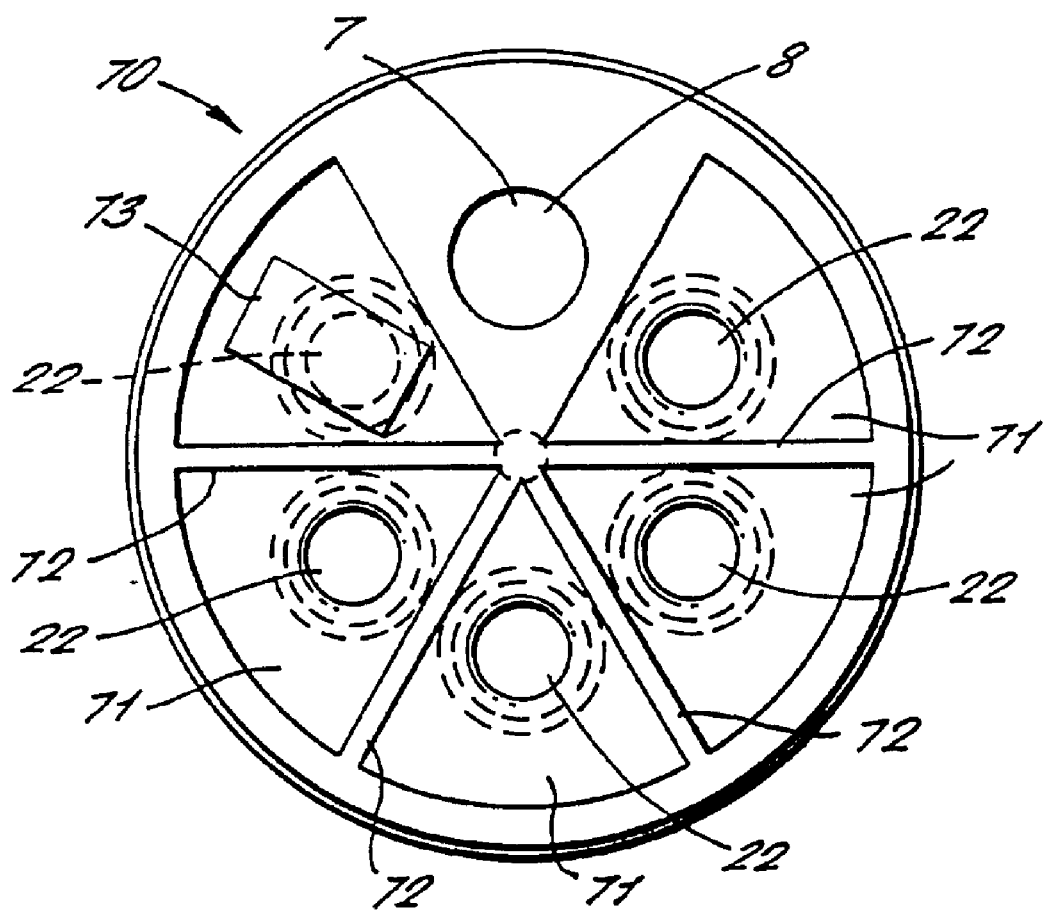
FIG. 53 is a plan view of the interior of a modified rotatable portion.

The device 1 may be modified to include more than one outlet port 22 as illustrated schematically in FIG. 53 which shows in plan view the interior of a modified rotatable portion 70. The modified rotatable portion 70 may be incorporated in a device similar to that shown in FIG. 34 and will therefore be described using corresponding reference numerals where appropriate for corresponding elements.

The rotatable portion 70 includes an access port 7 through which a suction cup is inserted in the manner illustrated in FIG. 34, subsequent operation of the device being such as to form a blister and sever the suction blister using a blade 18 as shown in FIG. 50 to provide an exposed area of de-epithelialised skin 8 accessible through the access port.

The modified rotatable portion 70 however provides a number of alternative outlet ports 22 as shown in FIG. 53 which are circumferentially distributed around a circle passing through the access port 7 such that by rotation of the rotatable portion 70 any one of the outlet ports 22 can be brought into registration with the area of skin 8 from which a blister roof has been removed.

The modified rotatable portion 70 comprises a series of compartments 71 which are divided from one another by radial partitions 72. The compartments 71 may therefore constitute reservoirs 11 whose operation corresponds to that of reservoir 11 described with reference to FIG. 34 above for containing respective quantities of liquid which is to be brought into contact with the area of skin 8. The respective liquids may be drugs of different type, quantities of the same drug having different strength, or drugs contained in different preparation (such as gel, solid or liquid form for example).

Operation of a device 1 incorporating a modified rotatable portion 70 therefore facilitates sequential administration of different stages of treatment according to which of the outlet ports 22 is brought into registration with the area of skin 8.

Alternatively, one or more of the compartments 71 may be utilised for a purpose other than containing liquid and may for example contain a bio sensor 73 for sampling body fluids exuding from the area of skin 8 following de-epithelialisation. In FIG. 53, the use of such a bio sensor 73 for the purpose of sampling and analysing exudate is illustrated schematically in one of the compartments 71.

The device 1 of FIGS. 34 to 53 relies upon manual actuation of an actuating ring 46 in order to achieve relative movement between the rotatable portion 5,70 and the stationary base 3. In order to assist the user in overcoming frictional forces between the relatively rotatable components, the device 1 may be modified as shown in FIG. 54 to include an actuating mechanism 74 operable to achieve a mechanical advantage between movement of an actuating member 75 and the rotatable portion 5.

Figure 54:
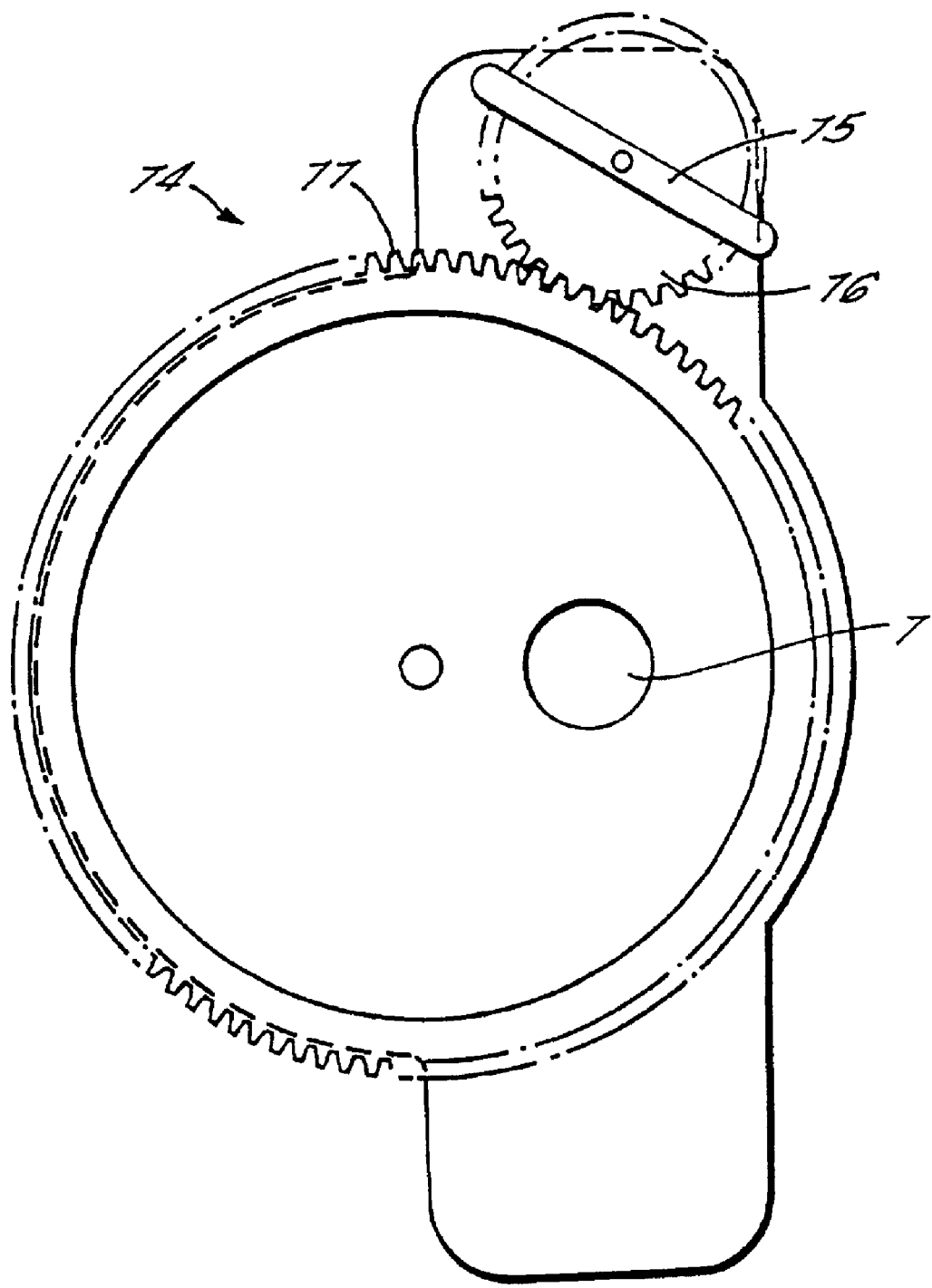
FIG. 54 is a plan view of an alternative device having a rotatable key for rotating the rotatable portion.

In the embodiment of FIG. 54, the actuating member 75 consists of a rotatable key which is connected for rotation with a geared pinion 76 which engages a circumferential rack 77 formed peripherally of the rotatable portion 5.

The user may thereby more readily rotate the rotatable portion relative to the base 3 by winding the actuating member 75, the gear ratio in this example being 3:1.

Figure 55:
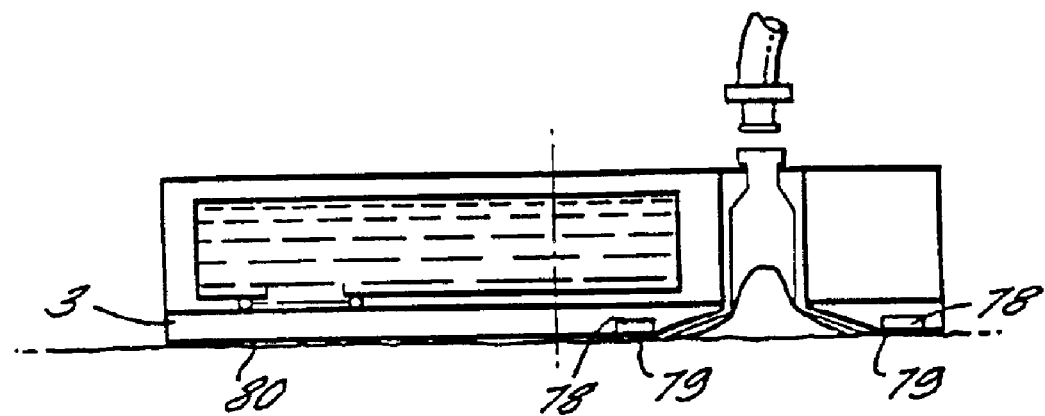
FIG. 55 is a schematic sectioned elevation of an alternative device having a skin heating element.

The device 1 as described in any of the alternative embodiments may optionally include a heating means comprising a heating element 78 as shown in FIG. 55. The heating element 78 comprises an annular resistive sheet connected to the base 3 so as to define an annular heated surface 79 which is flush with an underneath side 80 of the base 3 and therefore is held in contact with the skin 4 in use.

In the example of FIG. 55 the heated surface 79 has an external diameter of 10 millimeters and an internal diameter of 8 millimeters. The heating element 78 is connected to a power circuit (not shown) operable to pass electric current through the heating element sufficient to maintain the element at a controlled temperature of 41° C.

The power circuit may be operable to sense the temperature of the heating element 78, typically by measuring its resistance, and may control actively the current passing through the heating element in order to maintain the required temperature. Alternatively the heating element 78 may be formed of a material selected to have a coefficient of resistance which achieves self regulation at the required temperature when supplied from a constant voltage power supply.

The heating element 78 extends peripherally of the chamber 16 so as to warm the skin 4 during exposure to suction in the blister forming stage of operation of the device 1. The application of such warming decreases the time required for formation of the blister so that the use of the device is rendered more convenient and less subject to variation from patient to patient.

The controlled temperature is preferably maintained in the range 36° C. to 43° C.

The heating means may alternatively be energised by other means such as exothermic chemical reaction, the reaction being effected in a localised manner by known means and arranged to deliver heat to an annular heated surface corresponding to surface 79 in FIG. 55.

Figure 56:
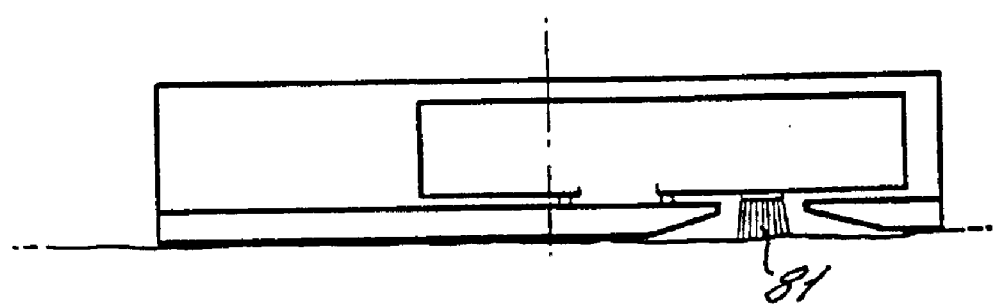
FIG. 56 is a schematic sectioned elevation of a further alternative device having a brush for removing debris from the exposed dermis.

A further optional feature which may be incorporated in any of the embodiments of the device disclosed herein is shown in FIG. 56 and comprises a brush 81. The brush 81 is connected to the rotatable portion 5 at a location such that during rotation of the rotatable portion the brush passes across the aperture 6 and extends into contact with the de-epithelialised area of skin 8. The brush 81 is formed of resilient bristles and is arranged so as to normally lie flat between the opposed surfaces of the rotatable portion 5 and the base 3, the brush resiling to extend automatically into the aperture 6 when suitably aligned.

The use of such a brush 81 may be advantageous in that residual portions of epidermis following rupture of the blister 17 can be removed from the exposed dermis and any exudate can be displaced in order to facilitate delivery of liquid within reservoir 11 when the rotatable portion 5 is further rotated to bring an outlet port 22 into registration with the aperture 6.

In a further alternative embodiment illustrated in FIG. 57, a further modified rotatable portion 82 has an outlet port 22 which is supplied with a controlled flow of liquid from a reservoir 83 via a capillary tube 84. A micro pump 85 with associated electronic control circuitry is operable to impel liquid from the reservoir to the outlet port 22 via the tube 84 and may be programmed to deliver metered quantities of liquid at predetermined time intervals or alternatively to supply a bolus quantity on demand.

The liquid supplied from the reservoir 83 may be a drug or any other liquid which it is desirable to introduce onto the exposed de-epithelialised area of skin 8 when the outlet port is positioned in registration with an aperture 6 of a device 1 as described in previous figures.

A similar arrangement is shown in FIG. 58 where micro pump 85 is connected via capillary tube 84 to the outlet port 22. The pump in this embodiment however operates in a reverse direction to deliver liquid from the outlet port 22 to a receptor 86 which may simply be a receptacle for capturing a sampled quantity of liquid or may alternatively comprise a sensor operable to carry out analysis on the sampled liquid. The outlet port 22 may in this arrangement be regarded as a sampling port and, optionally, suction may be applied to a sampling chamber communicating with the sampling port in a manner described below in order to enhance the rate at which liquid may be collected. The micropump may itself be used to provide such suction.

Figure 59:
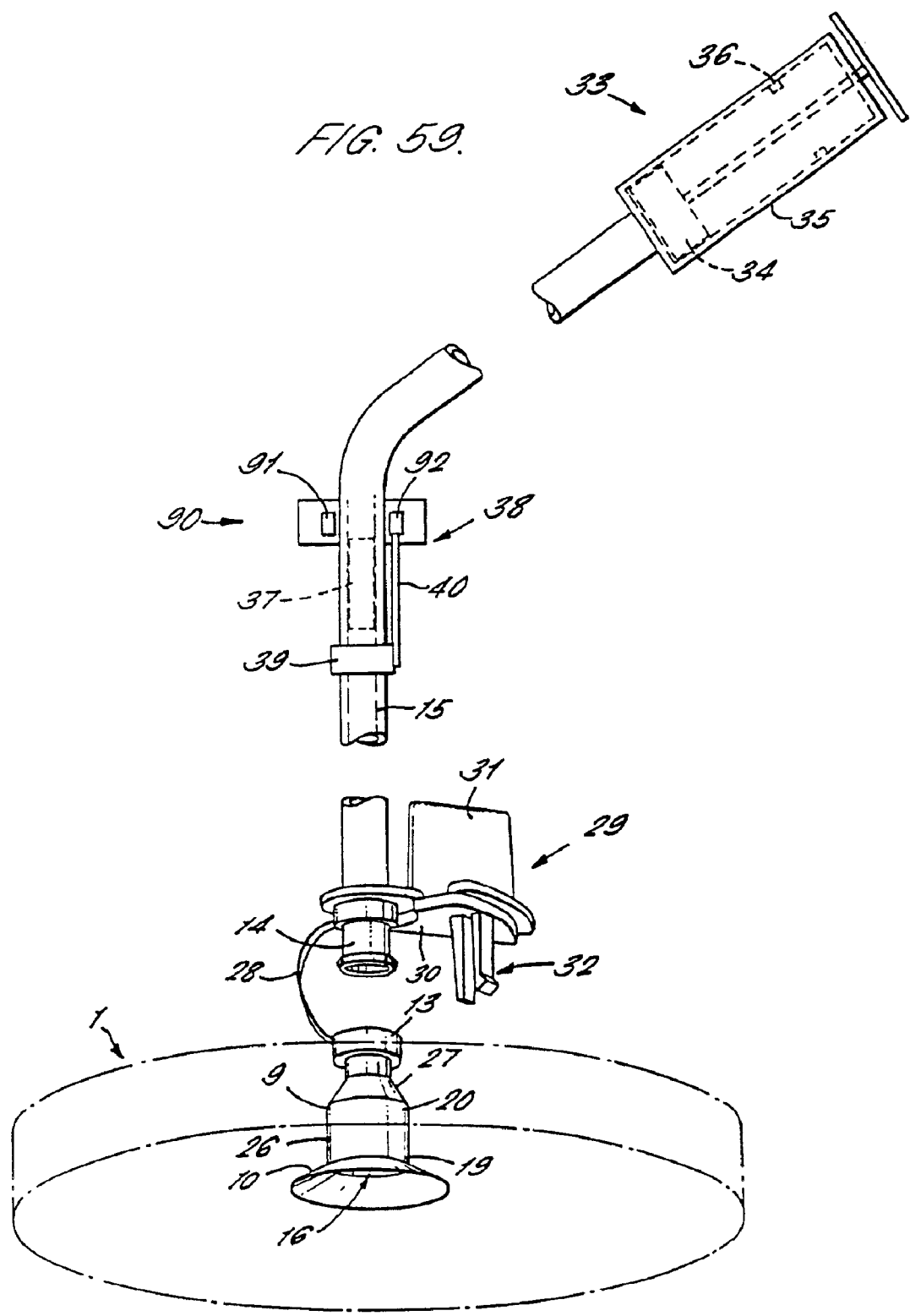
FIG. 59 is an exploded perspective view of a device having an alternative indicator for sensing blister development.

A further embodiment is illustrated in FIG. 59 which corresponds broadly to the arrangement shown in FIG. 38 but includes a modification to the indicator 38 which provides for automatic sensing of movement of the slug of liquid 37. In this embodiment an electro optic sensor 90 is supported by the clamping ring 39 upon the suction tube 15 and comprises a light source 91 arranged to direct light through the tube so as to be received by a light sensor 92. The clamp 39 may thereby be positioned at a location such that the slug of liquid is in registration with a suitable datum point on the indicator 38 at the commencement of a blister forming period in which suction is applied, the electro optic sensor being positioned at a predetermined linear displacement along the tube 15 so that movement of the slug 37 by a predetermined distance will interrupt the transmission of light to the light sensor 92. An electronic circuit associated with the sensor 90 may then be utilised to trigger an alarm so as to indicate to the user that formation of the blister has progressed to the required stage. Movement of the slug of liquid 37 by this predetermined amount thereby represents a predetermined volumetric displacement by the blister within the suction cup 9.

Figure 60:
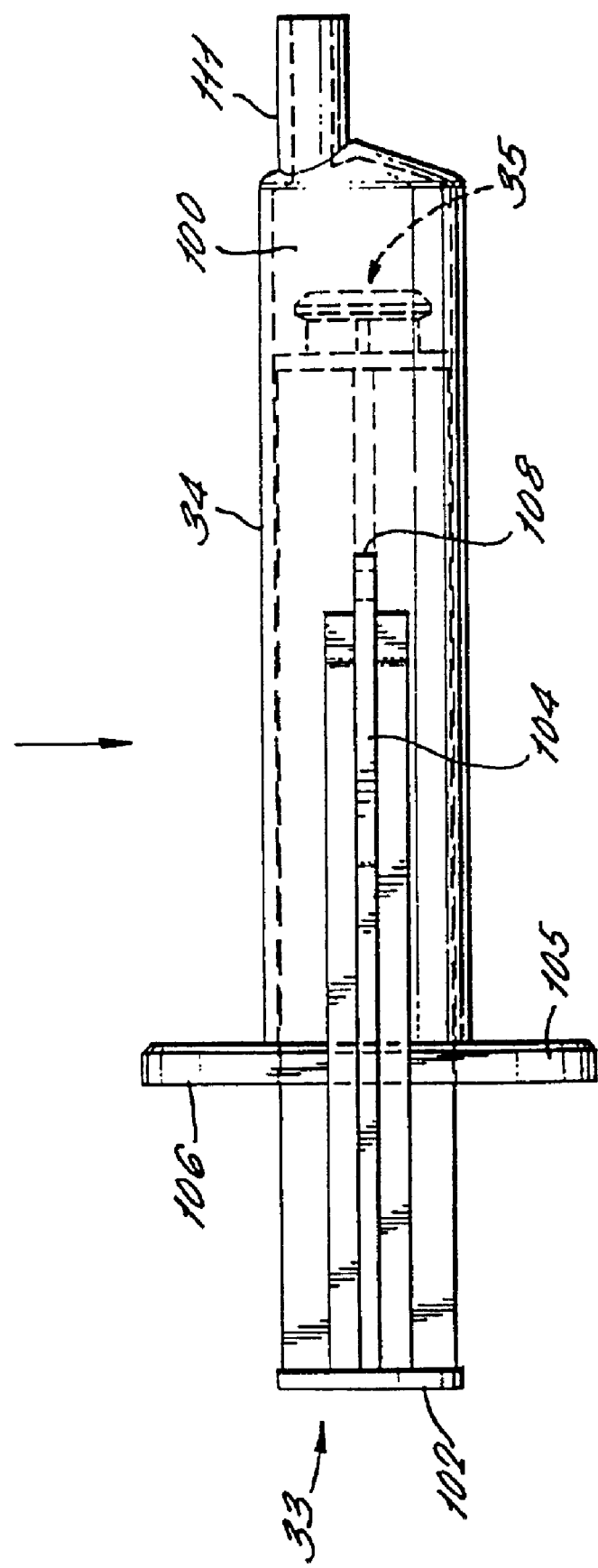
FIG. 60 is a partly section elevation of a syringe for use in the device of FIG. 59.

FIGS. 60, 61 and 62 illustrate a preferred embodiment of the syringe 33 described above with reference to FIG. 38. The syringe 33 comprises a piston 34 which is axially slidable within a cylinder 35 in order to increase the volume of a chamber 100 defined within the cylinder, thereby creating suction on demand.

The piston 34 is supported by an axially extending piston rod 101 of cruciform cross section which is integrally moulded with a transversely extending handle 102 and locking arms 103 and 104 which project from the handle so as to extend externally along the cylinder 35. The locking arms 103 and 104 are formed so as to be resiliently biased towards one another thereby tending to close around the cylinder 35.

The cylinder is provided with transversely projecting flanges 105,106 which are offset by 90 degrees about the axis of the cylinder with respect to both the radially extending handle 102 and the locking arms 103,104.

The locking arms 103 and 104 have respective free end portions 107 and 108 defining grooves 109 which indent the free end portions in an axial direction. The longitudinal extent of the locking arms 103 and 104 is less than that of the piston rod 101. In use, a user grips the handle 102 and pulls the handle away from flanges 105,106 so as to retract the piston 34 along the cylinder 35. When the displacement of the handle 102 is sufficient for the free end portions 107 and 108 to be pulled clear of the cylinder 35, the free end portions 107 and 108 spring radially inwardly towards one another. Suction created within the cylinder by retraction of the handle 102 will result in the piston 34 and handle 102 being biased against this direction of retraction so that by releasing the handle the piston will begin to travel in the return direction, this motion being arrested by engagement between the free end portions 107 and 108 and a lip 110 defining the end of the cylinder 35 such that the lip then extends into the slots 105 as shown in FIG. 62.

Suction within the chamber 100 is thereby communicated to the suction cup of the device 1 by means of the suction tube 15 which is connected to a nose portion 111 of the syringe formed integrally with the cylinder 35.

Since the locking arms 103 and 104 are resiliently biased into the locking position, the syringe 33 is in effect self locking and operates simply by manually retracting the handle 102. Although it would be possible for the user to release the suction by first withdrawing the handle 102 and splaying apart the locking arms 103 and 104, this would require some co-ordinated manipulation of the handle 102, flanges 105,106 and the locking arms 103,104 so it is most unlikely that any accidental release of the suction in this manner could occur. The syringe 33 thereby provides a means operable to apply suction to the suction chamber 16 of the device 1 which is simple to use, self locking and inherently resistant to accidental de-activation.

A further alternative embodiment of the present invention will now be described with reference to FIGS. 63 to 69 using corresponding reference numerals of previous Figures where appropriate for corresponding elements.

The device 1 is modified in FIG. 63 to include a patch applicator 120 which is operable to apply a patch 121 to the area of skin 8 following de-epithelialisation while the device 1 remains in situ.

The patch 121 consists of a disc shaped central element 122 which is to be reactively engagable with the de-epithelialised area of skin 8. Attached peripherally to the central element 122 is a relatively rigid support ring 123 having on its underside 124 an adhesive layer 125.

A protective film 126 overlays the underside 124 of the support ring 123 and the central element 122 thereby maintaining the efficacy of the adhesive layer 125 prior to use and sealing the central element 122.

The support ring 123 is held in position by means of pins 134 which are mounted on the rotatable portion 5 and which pierce the support ring 123. An actuator 127 is arranged so as to contact the support ring with the pins 134 extending slidably through the actuator such that by movement of the actuator the support ring can be disengaged from the pins. The patch 121 is received in a patch chamber 128 defined by the rotatable portion 5 which in the initial position of the rotatable portion communicates with a co-operating recess 129 formed in the upper surface of the base 3.

The actuator 127 projects upwardly and clear of the rotatable portion 5 so as to be externally accessible to the user and is spring loaded into a raised position in which the patch 121 is suspended clear of the base 3.

In this initial position, the interface between the protective film 126 and the adhesive layer 125 is in alignment with the locus of movement of the blade 18 between the base 3 and rotatable portion 5.

The actuator 127 is reciprocatable in a direction towards and away from the base 3 so as to be operable to displace support ring 123 and with it the patch 121 in a direction at right angles to the plane of the base 3.

The device of FIG. 63 has a base 3 which defines an aperture 6 which is of enlarged diameter sufficient to accommodate passage of the patch 121 and receives a suction cup 9 having a lip 10 whose underside is coated with adhesive layer 130. An annular plug 135 of resilient foam material is inserted between the suction cup 9 and the walls of the access port 7 so as to retain the suction cup in coaxial relationship with the access port and retain the suction cup relative to the base 3 and rotatable portion 5 prior to use. The lip 10 comprises an outer annular region 131 extending radially and at right angles to the cylindrical axis of the suction chamber 16 and further comprises an inner annular region 132 which is frustoconical in shape. It should be noted that the degree of conicity of the inner annular region in FIG. 63 is exaggerated for clarity and that the axial extent to which the inner annular region projects is typically a fraction of 1 millimeter.

As shown in the underneath plan view of FIG. 64, the base 3 is attachable to the skin 4 of a user by means of an adhesive tape 133. A circular opening 250 is provided in the tape 133 to coincide with the aperture 6 within which the skin site is to be accessed. An annular region 251 surrounding the opening 250 is provided with an acrylic adhesive coating so as to be impervious to body fluids and the remaining area of the tape receives a hydrocoloidal adhesive coating.

The suction cup 9 and the base 3 are thereby independently securable to the skin 4 by means of the adhesive layer 130 and the adhesive tape 133 respectively.

In use, the suction cup 9 is used to form a suction blister 17 as described above with reference to the device of FIG. 34. During the application of the device to the skin, the skin area 8 will adhere to the adhesive layer 130 and during the blister forming period the skin area 8 will tend to remain raised within the inner annular region 132 of the lip 10 by suction.

The device is then actuated by rotation of the actuating ring 46 as shown in FIG. 34 to move blade 18 through the suction cup 9 thereby severing both the cup and the blister 17 and exposing a de-epithelialised area of skin 8 within the aperture 6.

Figure 67:
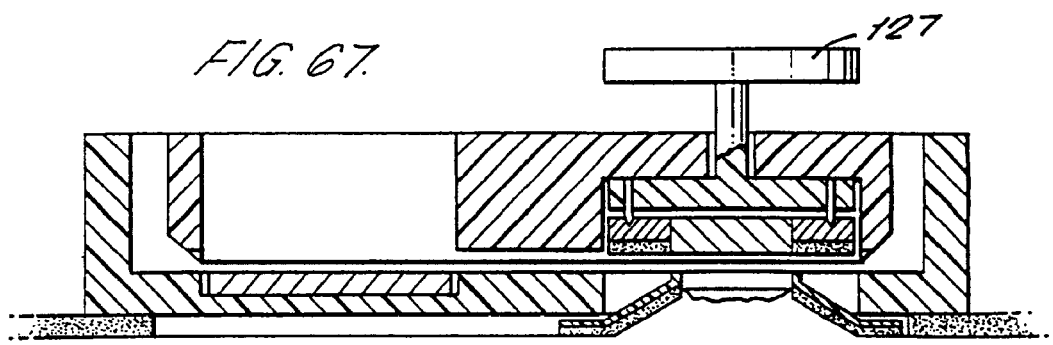
FIG. 67 is a schematic sectioned elevation of the device of FIGS. 63 to 66 after rotation of the actuating ring to place the patch in registration with the aperture.

The actuating ring 46 is further rotated to drive the blade 18 through the patch chamber 128 so as to separate the protective film 126 from the adhesive layer 125 as shown in FIG. 66. A thickened blade 18 of wedge shaped cross section may therefore be advantageously used in this embodiment in order to facilitate separation. The discarded protective film 126 is then allowed to fall into the recess 129 where it remains. The actuating ring 46 is further rotated to engage and rotate the rotatable portion 5 of the device and to move the patch chamber 128 into registration with the aperture 6 as shown in FIG. 67.

The actuator 127 is then depressed so as to displace the patch 121 axially within the patch chamber 128 towards and into contact with the area of skin 8, the diameter of the central element 122 being dimensioned so as to be slightly greater then the de-epithelialised area 8 of skin exposed when the blister is disrupted.

Figure 68:
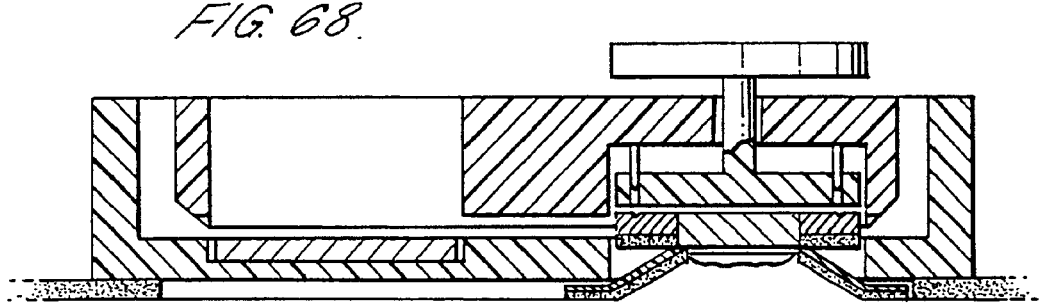
FIG. 68 is a schematic sectioned elevation of the device of FIGS. 63 to 67 after application of the patch.
Figure 69:
FIG. 69 is a schematic sectioned elevation of the patch of FIGS. 63 to 68 following removal of the device.

In depressing the actuator 127 as shown in FIG. 68, the support ring 123 is dissociated from the attachment pins 134 which remain stationary relative to the rotatable portion 5. The actuator 127 when subsequently retracted no longer carries with it the support ring 123 and the patch 121 remains in situ in contact with the area of skin 8. The adhesive tape 133 is then dissociated from the skin 4 and the base 3 dissociated from the skin so that the device can be lifted clear. The patch 121 remains in situ as shown in FIG. 69 with the central element 122 remaining in intimate contact with the de-epithelialised area of skin 8.

Figure 70:
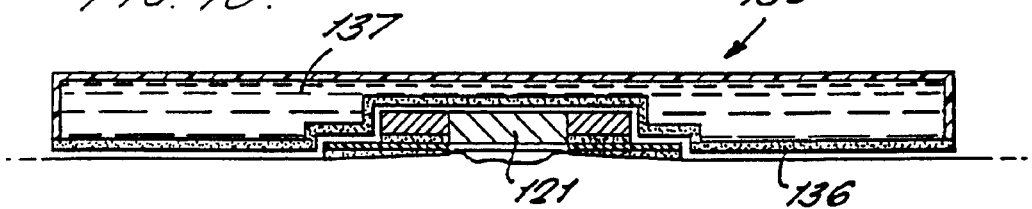
FIG. 70 is a schematic sectioned elevation of a conventional skin patch applied over the patch of FIG. 69.

The patch 121 may be a self contained means for administering a supply of drug and may for example comprise a porous pad impregnated with a liquid so that an active ingredient in the liquid is able to diffuse out of the pad and into the patient's bloodstream via the de-epithelialised area of dermis. Alternatively, the patch 121 may comprise a permeable membrane through which a liquid drug can be diffused from a conventional skin patch 135 which as shown in FIG. 70 is applied over the patch 121 so as to adhere to the skin by means of a peripherally extending adhesive layer 136.

When used in this arrangement the skin patch 121 may be regarded as an intervening patch which initially serves as a protective covering following exposure of the dermis and subsequently remains in an intervening position during a subsequent procedure. The conventional skin patch 135 although conventional in structure may contain drugs not normally associated with transdermal delivery but which can be successfully absorbed through a de-epithelialised dermis.

In the conventional skin patch 135 the adhesive layer 136 allows an active ingredient of a preparation 137 to diffuse through the adhesive layer over its entire extent but absorption will in general be taken up primarily at the de-epithelialised site.

Figure 71:
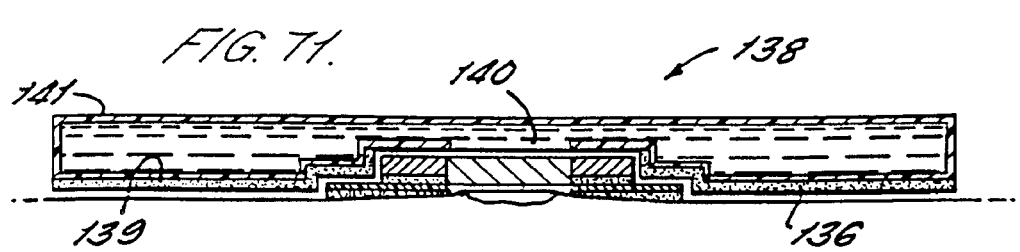
FIG. 71 shows a schematic sectioned elevation of a modified skin patch overlaying the patch of FIG. 69.

An alternative arrangement shown schematically in FIG. 71 uses a modified skin patch 138 in which an impermeable barrier 139 is adhered to the skin surrounding the de-epithelialised site by adhesive layer 136, the barrier layer 139 having a central aperture 140 in registration with the intervening patch 121 through which the active ingredient of the preparation may diffuse.

The impermeable barrier layer 139 forms part of an enclosure 141 within which the preparation is packaged.

The above use of patch 121 enables the newly formed de-epithelialised site to be covered prior to removal of the device 1 thereby avoiding exposure of the dermis to atmosphere. This techniques also ensures that the patch 121 is automatically positioned accurately in alignment with the de-epithelialised site and in a manner which can be effected by a relatively unskilled user.

The device 1 as described above and as modified in accordance with any of the alternative embodiments disclosed herein may therefore be used to form a de-epithelialised site which is subsequently overlaid by an implementing device used for implementing a required procedure such as transdermal delivery or sampling for diagnostic purposes. Examples of implementing devices already described include the reservoir 11 of FIG. 34, the patch 121 of FIG. 69 and the modified skin patch 138 of FIG. 71. Further examples of implementing devices will now be described using corresponding reference numerals throughout for corresponding elements where appropriate, it being understood that such implementing devices could be provided integrally within the device as shown in FIG. 34 or applied independently to a de-epithelialised site and including the possibility of use in conjunction with the intervening patch 121. A further option is to provide releasable connecting means operable between the device and each implementing device so that a number of implementing devices are interchangeable while the device is in use.

Figure 72:
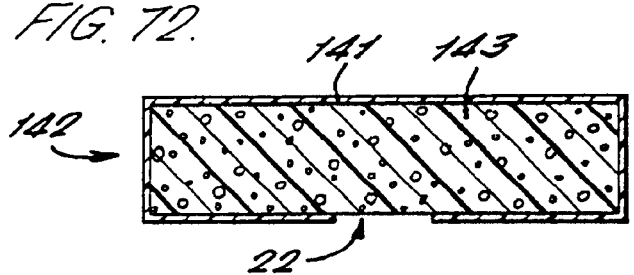
FIG. 72 is a schematic sectioned elevation of an implementing device which in use overlays a de-epithelialised site and which comprises a porous slab.

A further implementing device 142 is shown schematically in FIG. 72 and simply consists of an enclosure 141 defining an outlet port 22 and containing a porous slab 143 in which a drug is contained in aqueous solution. The porosity of the slab is selected to have a rate limiting effect on the diffusion of drug out of the slab and into the dermis.

The slab 143 may alternatively be a compressed mass of microspheres containing a drug. The microspheres may comprise biologically stable cross linked dextran or ceramics or may comprise bioerodible starch or other similar material. The slab may also be bounded by a bactericidal structure such as a mesh of fibrous silver bound material.

Figure 73:
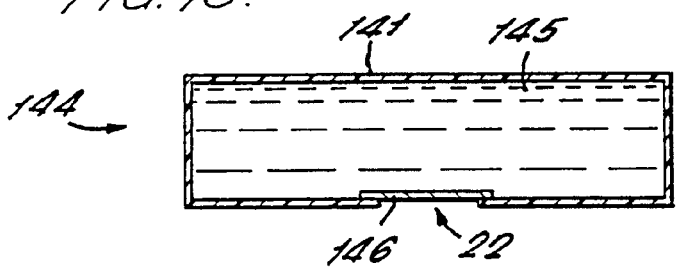
FIG. 73 is a schematic sectioned elevation of an alternative implementing device comprising a cell with a membrane extending across an outlet port.

A further alternative implementing device 144 shown schematically in FIG. 73 comprises an enclosure 141 defining a cell 145 and having a membrane 146 extending across the outlet port 22. The membrane 146 may be formed of a polymeric material having a rate limiting effect on diffusion of a preparation contained within the cell into the dermis. The membrane 146 may be bound with silver chloride as a bactericide. The diffused preparation may also include a vasodilating agent in order to increase blood flow locally in the exposed dermis and/or an anticoagulant to prevent formation of fibrin which could otherwise obstruct pores in the membrane.

The membrane 146 may alternatively be a fibrous network of bound silver. The membrane 146 may be constructed as a fine mesh filter have a pore size of 0.2 to 2 microns for example in order to prevent the passage of bacteria into the cell 145.

Figure 74:
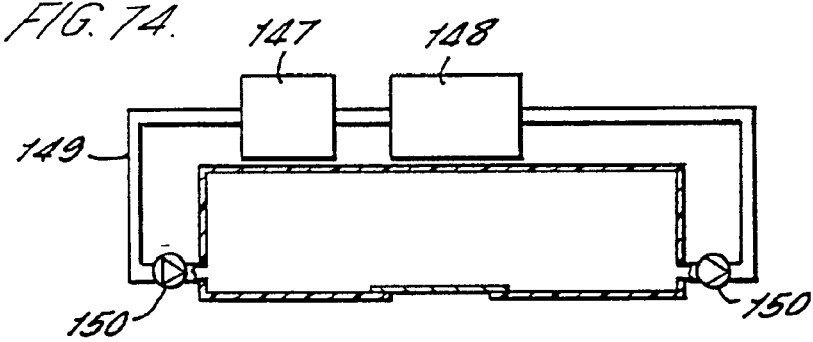
FIG. 74 is a schematic sectioned elevation of a further implementing device having a circulating pump and filter.

Since such implementing devices are likely to be in use for a number of days in registration with the de-epithelialised site, it will generally be desirable to provide some means of preventing bacterial contamination of the preparation contained within cell 145. Where the cell 145 contains a flowable material such as a liquid or gel, the material may be circulated through a filter 147 as illustrated schematically in FIG. 74 where the filter is connected in series with a pump 148 by capillary tube 149. Both ends of the tube 149 are connected to the cell 145 such that by operation of the pump the preparation within the cell is circulated and filtered. Non-return valves 150 are also incorporated in the circuit. The pump may be a simple displacement pump which in its simplest form can be a resilient tube with non-return valves positioned upstream and downstream of the tube so that repeated manual flattening of the tube will result in pumping action. Alternatively the pump may be an electronically operated micro pump such as a piezo electric membrane pump or peristaltic pump.

Figure 75:
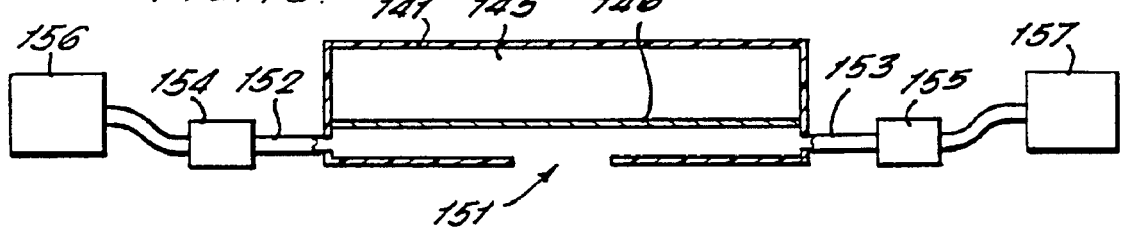
FIG. 75 is a schematic sectioned elevation of a further alternative implementing device providing a through flow of liquid.

It may also be advantageous to provide for a flow of fluid through a space 151 between the membrane 146 and the dermis. As shown schematically in FIG. 75, inlet and outlet tubes 152 and 153 respectively are connected to the enclosure 141 for the inflow and outflow of fluid. In the example of FIG. 75, the tubes 152 and 153 are connected to releasable connectors 154 and 155 of a standard luer connector type thereby enabling a supply 156 of cleansing fluid to be connected to the inlet tube and a syringe or other suction device 157 to be connected to the outlet tube. Cleansing fluid may thereby be periodically drawn through the space 151.

This cleansing operation may be required to remove excess exudate or to remove the products of enzymic reaction or other reactions between the exudate and the drug diffusing through the membrane 146.

The apparatus of FIG. 75 may also be used for taking samples of exudate, or samples of substances extracted from the exudate using a filtering membrane for example, the contents of this syringe 157 being available for subsequent analysis.

The apparatus of FIG. 75 may also be modified by removal of the membrane 146 and without including any drug within the cell 145 in circumstances where the de-epithelialised site is to be used only for sampling exudate and not for the transdermal delivery of any drug. In such an arrangement, the volume of the cell 145 is preferably reduced to a minimum and may for example be provided by a groove formed in a block of material.

Figure 76:
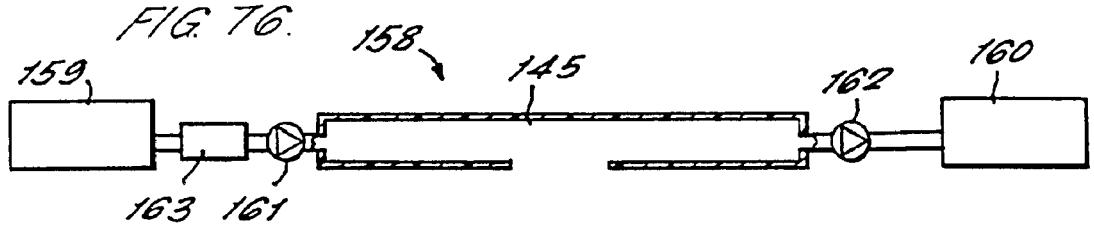
FIG. 76 is a schematic sectioned elevation of a further implementing device in which a through flow of liquid is directed to a collecting chamber.

An alternative implementing device 158 is shown schematically in FIG. 76 in which the enclosure 141 receives a through flow of fluid from a reservoir 159 to a collecting chamber 160. Check valves 161 and 162 are provided upstream and downstream of the cell 145 respectively and a displacement pump 163 is operable to deliver metered quantities of fluid from the reservoir.

In this arrangement the volume of the cell 145 is minimised and may be constituted by a capillary tube opening into a small space localised above the de-epithelialised dermis. The reservoir 159 and collecting chamber 160 may be relatively small containers associated in structure with the enclosure 141 or preferably may be larger containers connected remotely from the enclosure 141 by respective tubes. The pump 163 may conveniently be a peristaltic pump.

The pump 163 may be operated continuously or in intermittent bursts in order to provide a flow of fluid over a prolonged period, the fluid typically comprising a drug with an active ingredient which is transdermally absorbed. A particular advantage of this technique is that the products of any reaction between exudate from the dermis and the fluid are transported away to the collecting chamber 160, as for example in the case of peptides where enzymic reaction from exudate is likely to occur.

A further advantage is that the drug concentration in the flowing fluid is less susceptible to depletion due to diffusion through the dermis so that the rate of diffusion can be accurately controlled.

Figure 77:
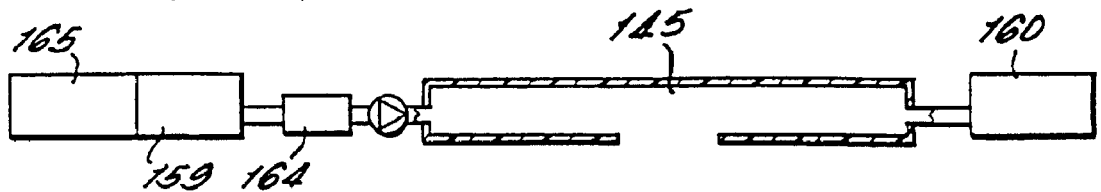
FIG. 77 is a sectioned elevation of a further alternative implementing device in which a pressurised supply of fluid is released through a flow restrictor to provide a through flow of liquid.

An alternative implementing device 159 shown schematically in FIG. 77 derives a continuous through flow of fluid from reservoir 159 via a flow restrictor 164, the reservoir 159 being provided with a pressurising means such that the contents of the reservoir are continuously pressurised and gradually are released through the flow restrictor so as to pass through the cell 145 and into the collecting chamber 160. The pressurising means 165 may simply be a spring loaded actuating acting on a flexible bag type reservoir or may incorporate pressurised gas or a resilient bag to constantly maintain the contents of the reservoir under pressure.

Figure 78:
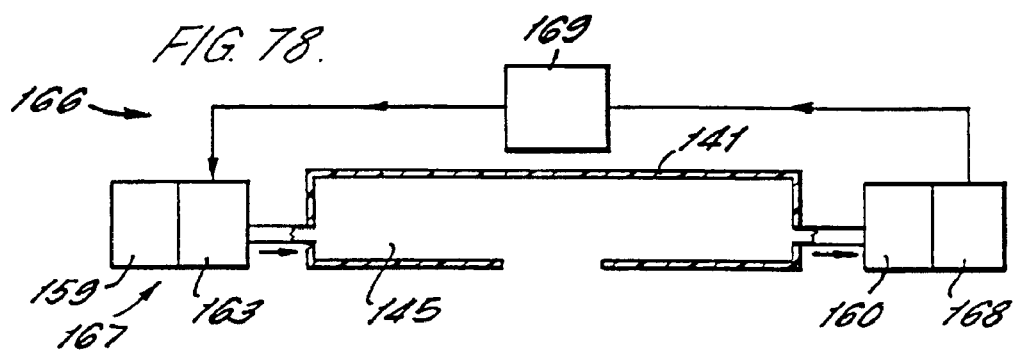
FIG. 78 is a schematic sectioned elevation of a further alternative implementing device incorporating a bio sensor.

A further alternative implementing device 166 is shown schematically in FIG. 78. A continuous or intermittent flow of fluid is passed through cell 145 from a source 167 to a collecting chamber 160 which incorporates a bio sensor 168. An electronic output signal from the bio sensor 167 is fed to a control unit 169 which controls the actuation of the source 167 in its delivery of fluid, the source 167 being provided with both a reservoir 159 and a pump 163 for this purpose.

The bio sensor 168 may be any one of a number of available bio sensors depending on the nature of the parameter which is to be controlled. The bio sensor may for example be an optical sensor responsive to light absorbed in passage through exudate extracted from the cell 145, such a sensor being operable for example to measure glucose levels to give an indication of the glucose level in the patient's bloodstream, particularly where the administered drug is insulin.

Figure 79:
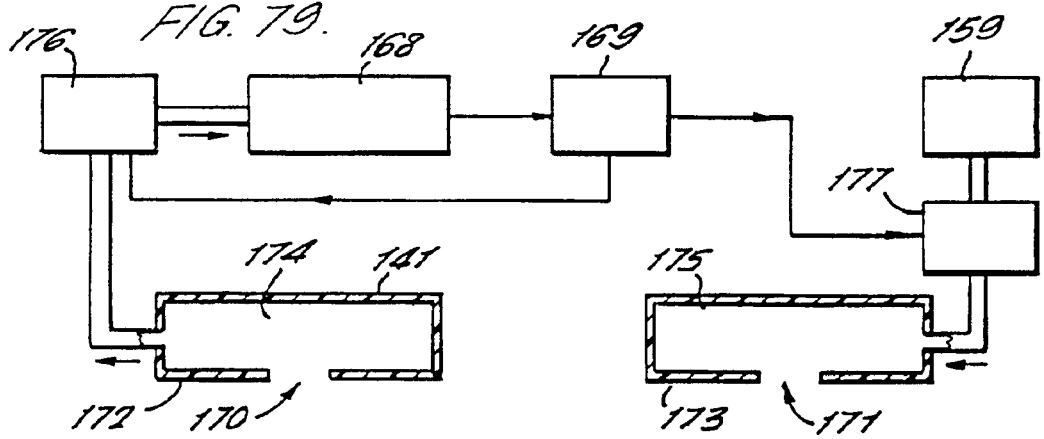
FIG. 79 is a schematic sectioned elevation of an arrangement in which two separate implementing devices are utilised for sampling and drug delivery.

It may be desirable to provide two separate de-epithelialised sites 170 and 171 as shown schematically in FIG. 79 used for sampling and drug delivery respectively. In this configuration, respective enclosures 172 and 173 provide sampling and drug delivery cells 174 and 175 respectively arranged in registration with the skin sites.

Exudate collected in cell 174 is delivered by a pump 176 to a bio sensor 168 which provides a measurement signal for control unit 169. The control unit 169 actuates a further pump 177 to deliver metered quantities of drug to the cell 175 from a reservoir 159.

The pump 177 may for example be a micro pump of the type normally used in bubble jet ink printers and relying upon the pulsed application of heat to expel discrete quantities of liquid within capillaries by the formation of vapour bubbles. Such a micro pump, in this case typically referred to as a thermal droplet generator, an array of nozzles is provided, each having an associated liquid channel of nano-liter volume with a heating element associated with each channel, the nozzle outlet dimensions being of the order of 40 microns diameter.

Activation of the nozzles can then be programmed using a suitable pulse generator and the system calibrated in terms of the number of pulses required to deliver a metered volume of drug.

Such an arrangement may for example be used to administer a quantity of drug and to monitor the level of a measurable parameter in the exudate in order to generate a feed back signal controlling the rate of delivery of the drug in order to stabilise the measured parameter at a required level. A control unit may also be programmed to activate the pump 176 to sample the exudate at intervals which may be regular or dependent upon the sensed value.

Figure 80:
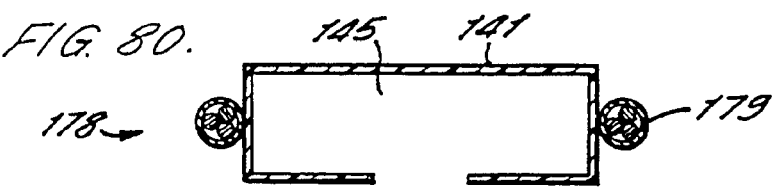
FIG. 80 is a schematic sectioned elevation of a further alternative implementing device provided with an electric heating element for heating the contents of the cell.

It may also be desirable to utilise various means for enhancing or controlling the rate of delivery of a drug. In FIG. 80 for example a further alternative implementing device 178 is shown schematically to comprise an enclosure 141 provided with an electric heating element 179 which when actuated will heat the contents of cell 145 to a controlled temperature. The temperature of the heating element 179 can be monitored simply by monitoring its electrical resistance or by means of a separate temperature sensing element. In the example of FIG. 80, the cell 145 contains a quantity of drug mixed with a hydro gel which has a temperature dependent diffusivity. By controlling the electrical current passing through the heating element 179 from an associated control circuit it is thereby possible to increase or decrease the rate at which drug is delivered to the de-epithelialised skin site.

Figure 81:
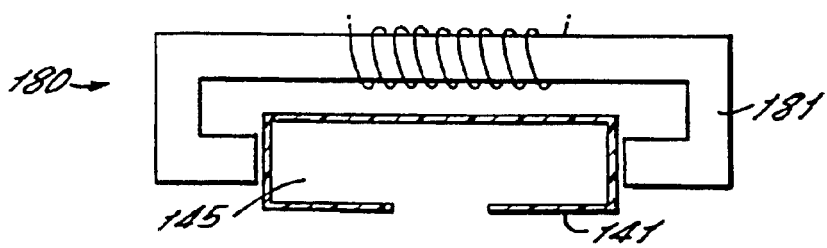
FIG. 81 is a schematic sectioned elevation of a further alternative implementing device in which an alternating magnetic field is applied to the contents of the cell.

A further alternative implementing device 180 is shown schematically in FIG. 81 in which the enclosure 141 is exposed to an alternating magnetic field provided by a magnetic circuit 181 so as to apply an alternating magnetic field to the contents of cell 145. The contents of cell 145 are selected to be a mixture of permanent magnetic particles encapsulated in a polymeric material and porous polymeric particles in which a quantity of drug is absorbed. The rate at which drug diffuses out of the polymeric particles is dependent upon the degree of vibrational excitation induced by the magnetic field acting on the magnetic particles thereby allowing the rate of drug release to be controlled.

Figure 82:
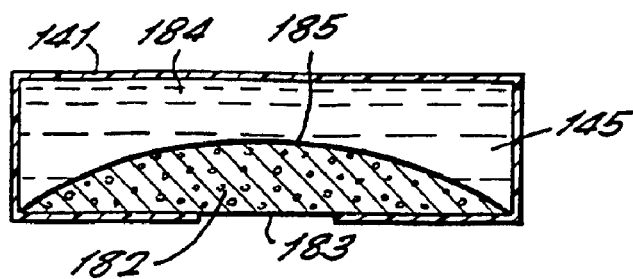
FIG. 82 is a schematic sectioned elevation of a further alternative implementing device in which drug is released in a controlled manner by rehydration of a hydrogel polymer.

The release of a drug in a progressive and controlled manner may also be effected by incorporating the drug into a non-hydrated hydrogel polymer and introducing a quantity of water into contact with an outer surface of a bead of the gel, progressive hydration then occurring as a gradual process accompanied by a complimentary release of drug. As shown schematically in the example of FIG. 82, a bead of gel 182 is placed within cell 145 such that a surface of the gel 183 is presented to the de-epithelialised skin site. A quantity of water 184 is introduced into the remaining volume of the cell 145 and is assimilated into the bead through an outer surface 185 of the bead. As the water is assimilated into the bead, the volume of the bead increases and the liquid drug is expelled through the surface 183 so as to delivered to the dermis.

Figure 83:
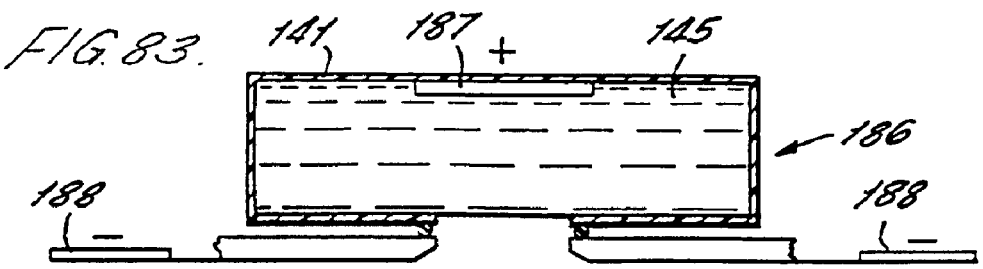
FIG. 83 is a schematic sectioned elevation of an alternative implementing device incorporating electrodes for iontophoresis delivery.
Figure 84:
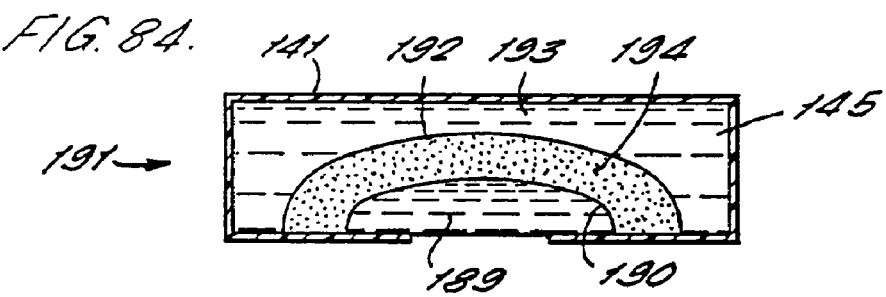
FIG. 84 is a schematic sectioned elevation of a further alternative implementing device incorporating an osmotic system for drug delivery.

The technique of iontophoresis may also be utilised as shown schematically in FIG. 83 where an alternative implementing device 186 incorporates a first electrode 187 within cell 145 and a second annular electrode 188 which is placed peripherally of the enclosure 141 and in contact with the skin peripheral to the de-epithelialised site. By applying a voltage of appropriate polarity between the first and second electrodes 187 and 188, ionised drug molecules can be urged in the direction of absorption through the dermis in order to enhance or control the rate of absorption. This apparatus may also be utilised in the reverse technique of enhancing the rate of production of certain exudates for sampling.

It may also be advantageous to pressurise a volume of liquid drug 189 in contact with the de-epithelialised dermis in order to enhance the rate of drug absorption. Such pressure may for example be derived as shown in FIG. 51 by dividing the contents of cell 145 using an impermeable membrane 190 to isolate the drug 189 from an osmotic system 191. The osmotic system 191 comprises a semi-permeable membrane 192 which separates a volume of water 193 from a volume of a saturated salt 194. Migration of water through the semi-permeable membrane results in an increased volume of the salt thereby exerting a pressure on the impermeable membrane 190 and pressurising the volume of drug 189.

Figure 85:
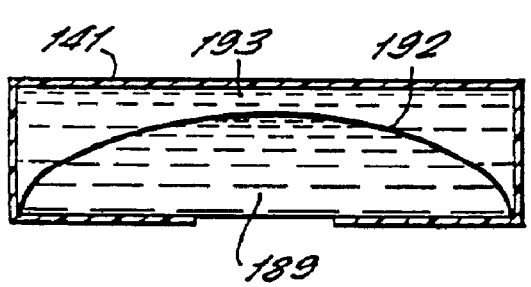
FIG. 85 is a schematic sectioned elevation of a further alternative device having a semi-permeable membrane.

An alternative arrangement as shown in FIG. 85 in which a liquid drug is separated from a quantity of water 193 by a semi-permeable membrane 192. In this arrangement water diffuses into the liquid drug through the rate controlling membrane and an associated increase in pressure in the liquid enhances the rate of drug absorption through the de-epithelialised dermis.

Figure 86:
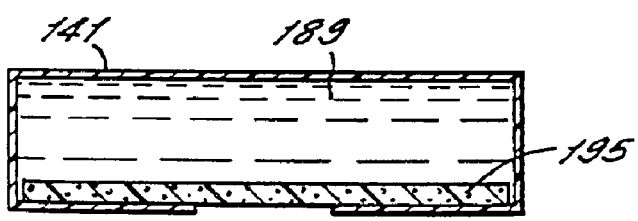
FIG. 86 is a schematic sectioned elevation of a further alternative implementing device incorporating a charged polymer membrane.

A further alternative is shown in FIG. 86 which simply incorporates a charged polymer membrane 195 intermediate the dermis and a liquid drug of a type in which the active ingredient comprises charged ions (for example a peptide or protein).

The inherent electric field provided in such a membrane interacts with the charged ions in a predetermined manner which can be selected to enhance diffusivity through the membrane for the purpose of absorption.

Figure 87:
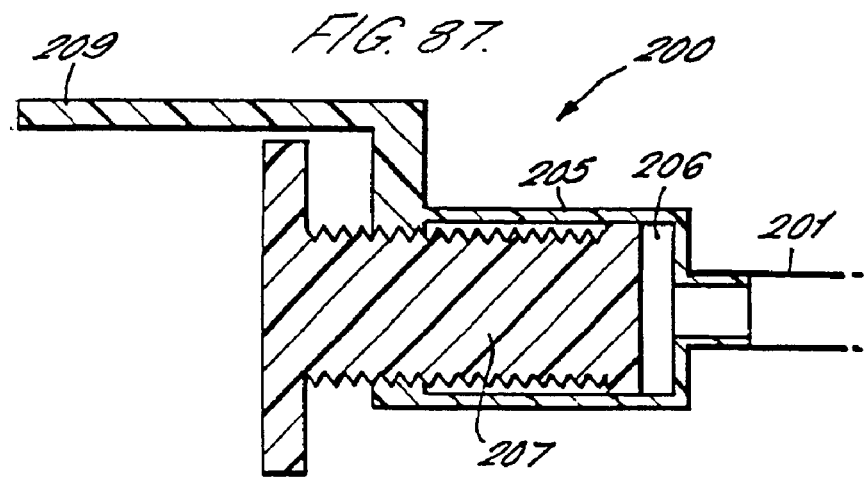
FIG. 87 is a sectioned elevation of a dosing device for incrementally delivering liquid doses.
Figure 88:
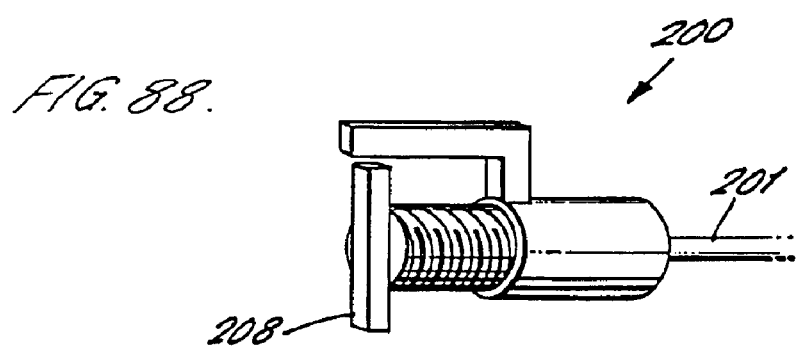
FIG. 88 is a perspective view of the dosing device of FIG. 87.
Figure 89:
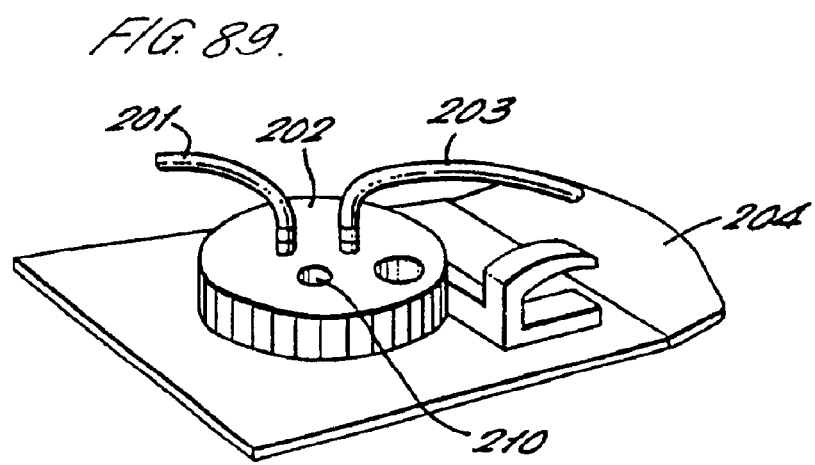
FIG. 89 is a perspective view of a device receiving liquid from the device of FIGS. 87 and 88.

FIGS. 87 to 89 illustrate the manner in which a metered dose of liquid can be delivered to a de-epithelialised site using a metered dose dispenser 200 connected via a tube 201 to an enclosure 202 overlaying the de-epithelialised site.

The enclosure 202 is provided with an outlet tube 203 connected to a flexible bag type collecting chamber 204.

The metered dose dispenser 200 consists of a cylinder 205 defining a reservoir chamber 206 which is screw threaded to receive a threaded piston 207 which is manually rotatable by means of a handle 208. A reference arm 209 projects from the cylinder 205 parallel to the axis of the piston 207 so as to provide a reference against which the position of the handle 208 is alignable, the dimensions of the chamber 206 and the screw pitch of the piston being selected such that metered units of volume are displaced from the reservoir chamber 206 at each complete rotation of the handle.

The volume of the reservoir chamber 206 will typically be in the range 0.3 to 0.5 milliliters.

A typical application of the metered dose dispenser 200 would be for the delivery of a drug for pain relief, the drug being self administered by a patient at timed intervals or whenever required. The concentration of drug within the enclosure 202 will tend to deplete with time as a result of absorption into the body via the de-epithelialised site and is replaced by actuation of the dispenser 200 with a fresh volume of drug, the spent drug solution together with excess exudate from the site being displaced so as to be deposited in the collecting chamber 204 via the outlet tube 203.

The enclosure 202 may also be provided with a valved inlet port 210 allowing a flushing solution to be injected into the enclosure 202 from a syringe or other suitable source in order to periodically flush and cleanse the enclosure, excess flushing fluid and exudate being deposited in the collecting chamber 204.

Apparatus described above with reference to the various embodiments of the invention may comprise components which have siliconised surfaces to minimise bacterial adhesion, particularly for those surfaces expected to come into contact with body fluids.

Figure 90:
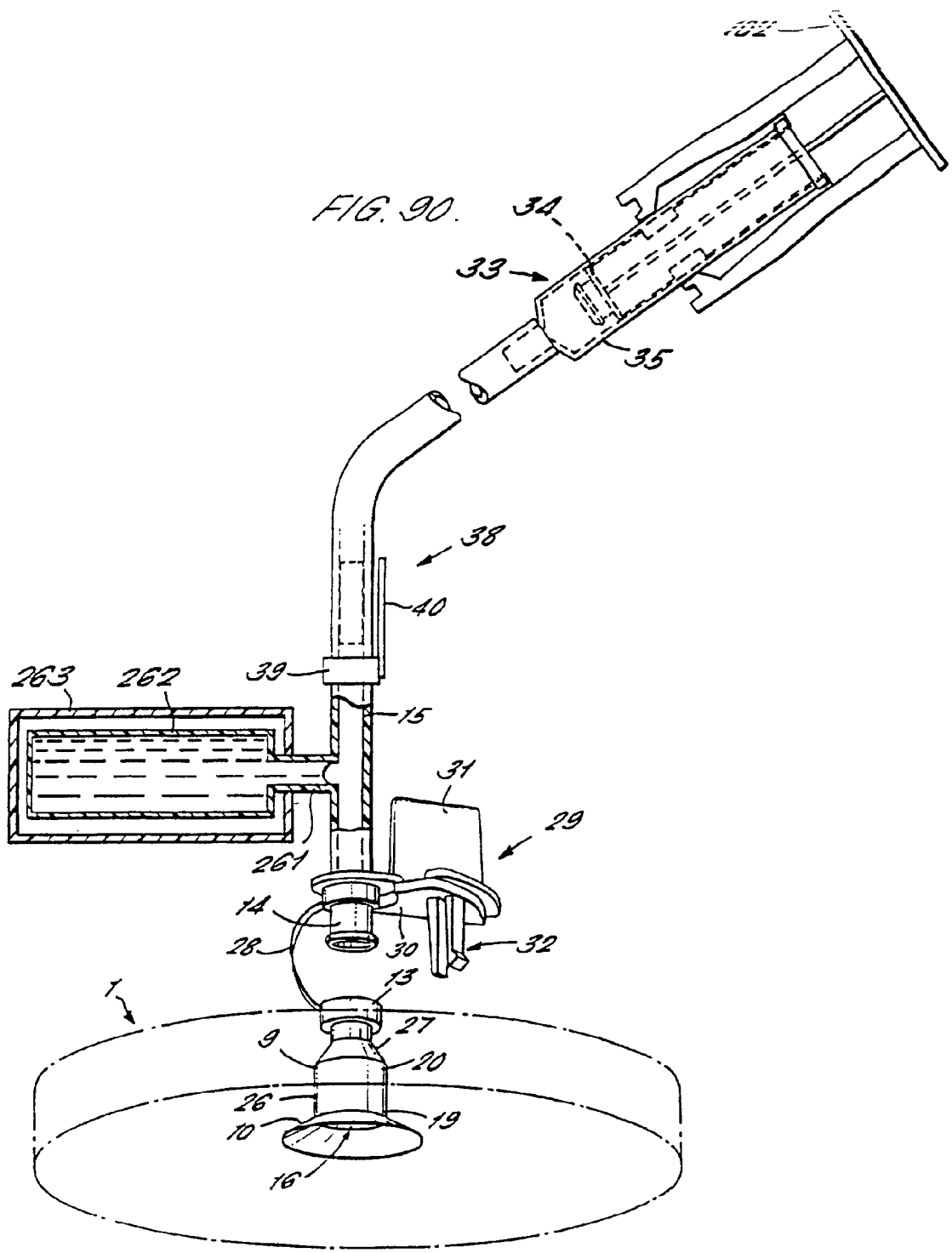
FIG. 90 is a schematic perspective view of the suction cup, arming device and syringe, further including a modified indicator having a liquid storage structure.

FIG. 90 shows a modification to the indicator 38 shown in FIG. 38, the modified indicator now being described using corresponding references to previous Figures where appropriate for corresponding elements.

In FIG. 90, the suction tube 15 is provided with a connecting side arm portion 260 communicating with a liquid storage chamber 261 provided by a liquid storage structure 262.

The liquid storage structure 262 is cylindrically formed from a deformable material having a shape memory such that it retains its cylindrical shape when internal and external pressures are equalised.

A suitable material for forming the structure is latex.

The apparatus shown in FIG. 38 would normally be supplied in the configuration shown in which liquid is contained within the liquid storage chamber 261 without extending into the suction tube 15. This arrangement is advantageous over the configuration shown in FIGS. 38 and 59 where the slug of liquid could potentially become disrupted prior to use by impact and might for example be divided into two or more sections.

Figure 91:
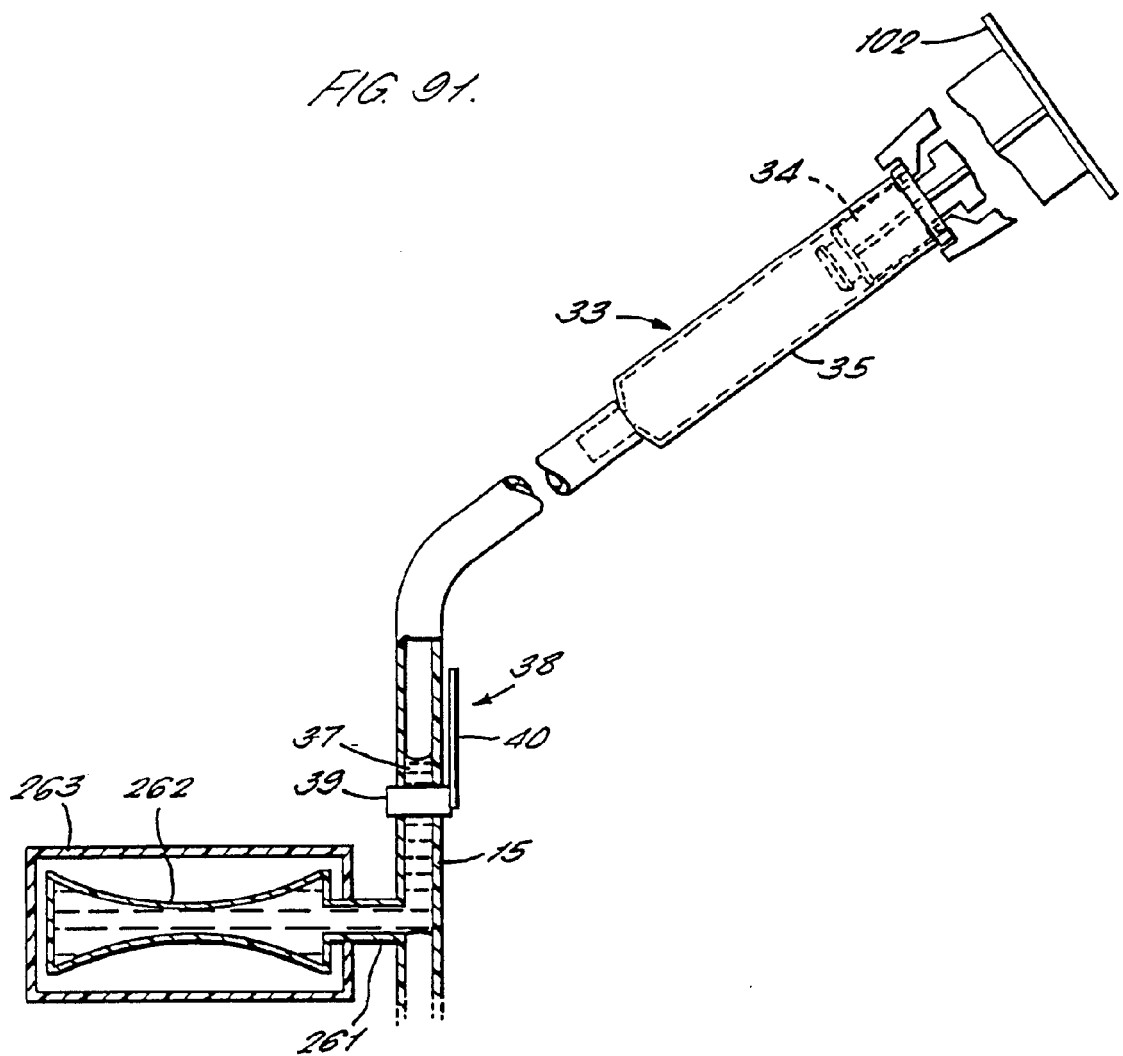
FIG. 91 is a schematic view of the modified indicator of FIG. 90 showing a slug of liquid being introduced into the tube.

As shown in FIG. 91, the application of suction within the tube 15 by retracting the piston 34 draws liquid from the liquid storage chamber 261 into the tube, liquid being displaced from the chamber by a partial collapse of the structure 262 in response to the internal pressure being reduced by the effect of suction.

With the tube 15 operatively connected to the suction cup 9 for a prolonged period, a suction blister will eventually form and the formation of the blister will displace a volume of air from within the suction cup, this displacement being transmitted through the tube so as to displace a slug of liquid 37 relative to its initial position, this displacement being detectable by operation of the indicator 38. It will be apparent that the alternative indicator shown in FIG. 59 could equally well be operable in conjunction with such a side arm 260 and structure 262.

Figure 92:
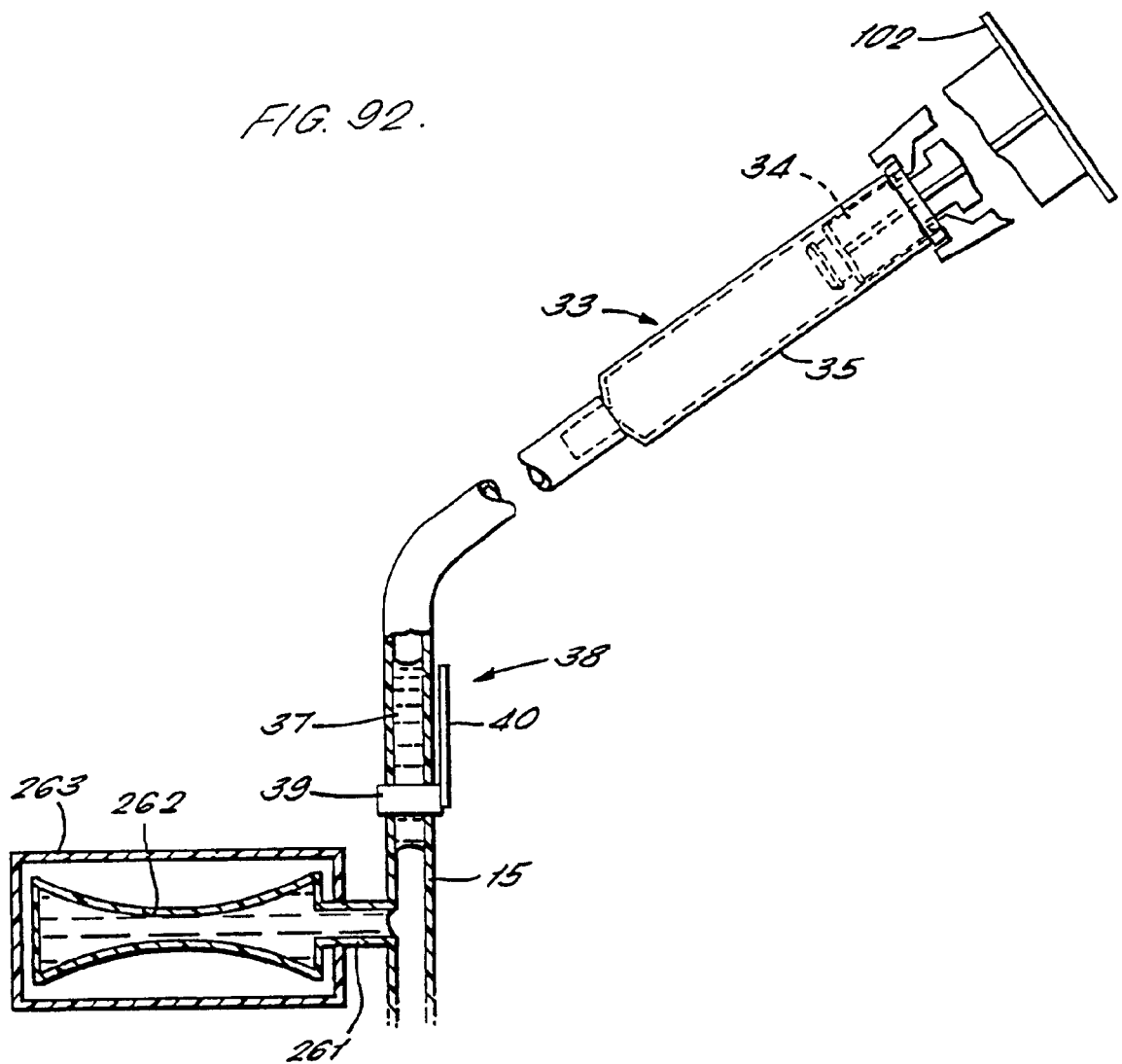
FIG. 92 is a schematic view of the indicator of FIGS. 90 and 91 showing displacement of the slug of liquid following formation of a suction blister.

In FIG. 92, the displaced slug of liquid 37 has moved through a displacement indicative of a suction blister having fully formed thereby indicating to the user that the blister forming period is completed and that it is therefore time to commence the next stage of operation of the apparatus.

The liquid storage structure 262 is located within a rigid enclosure 263 which prevents the structure being inadvertently compressed by handling while at the same time admitting ambient air pressure to the external surfaces of the structure.

Figure 93:
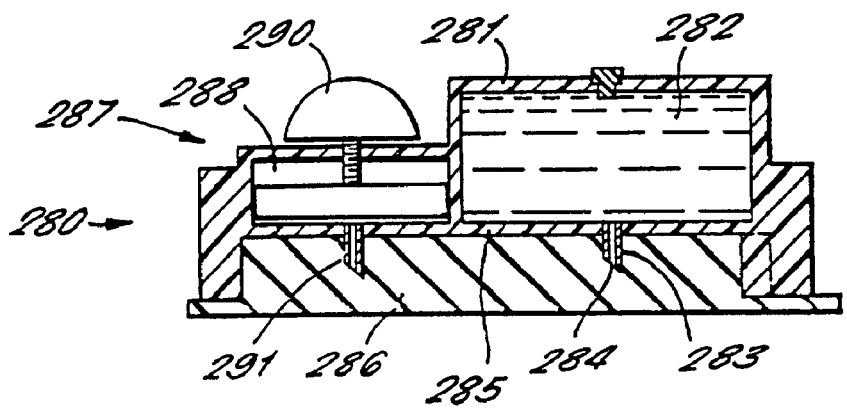
FIG. 93 is a schematic sectioned elevation of an implementing device having releasable connecting means.

FIGS. 93 to 98 illustrate the manner in which implementing devices may be interchangeably connected to a device in accordance with the present invention. In FIG. 93, an implementing device 280 comprises a reservoir 281 defining a fluid receiving chamber 282 and having a cannula 283 which defines an outlet 284 communicating with the chamber.

The implementing device 280 is in the form of a disc 285 upon which the reservoir 281 is mounted with the cannula 283 projecting through the disk. FIG. 93 shows the device 280 in its storage condition in which a closure 286 overlays the disc 285 and is partially penetrated by the cannula 283 thereby closing the outlet 284.

A suction device 287 is also mounted on the disc 285 and comprises a suction chamber 288 in which a piston 289 is retractable to create suction by rotation of a screw-threaded actuator 290.

A second cannula 291 communicating with the suction chamber also projects through the disc 285 into the closure 286.

Figure 94:
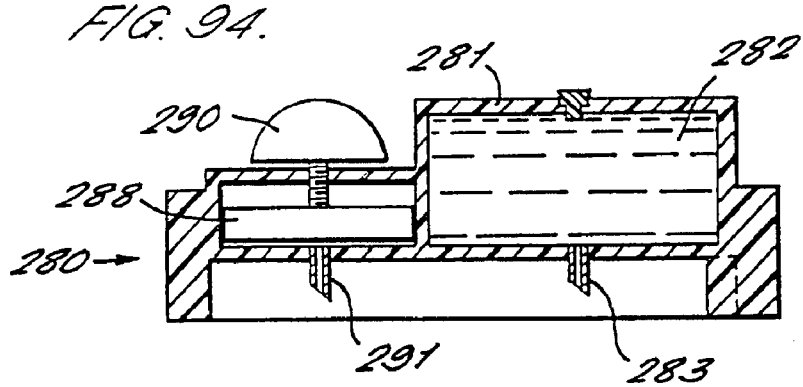
FIG. 94 is a sectioned elevation of the implementing device of FIG. 93 after removal of a closure.
Figure 95:
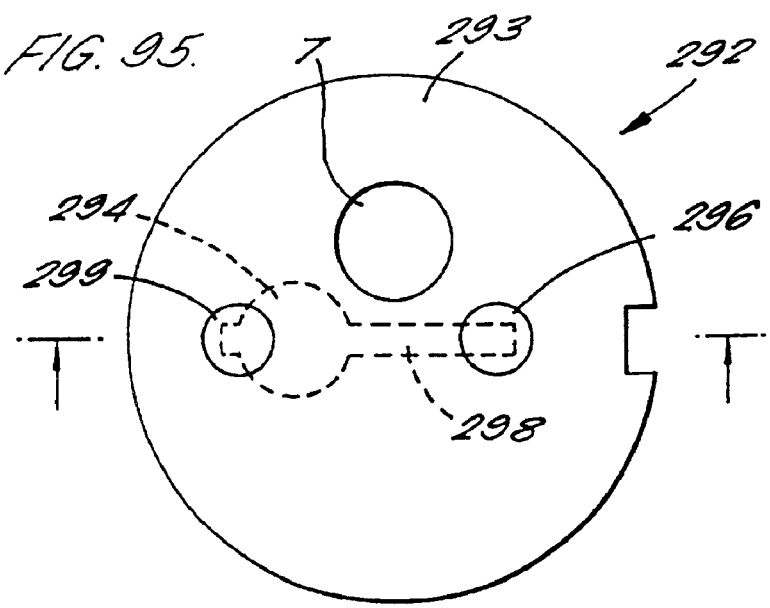
FIG. 95 is a plan view of a movable portion of a transdermal delivery device cooperable with the implementing device of FIGS. 93 and 94.

In FIG. 94, the closure 286 has been discarded immediately prior to use of the implementing device 280, thereby exposing the first and second cannulas 283, 291.

Figure 96:
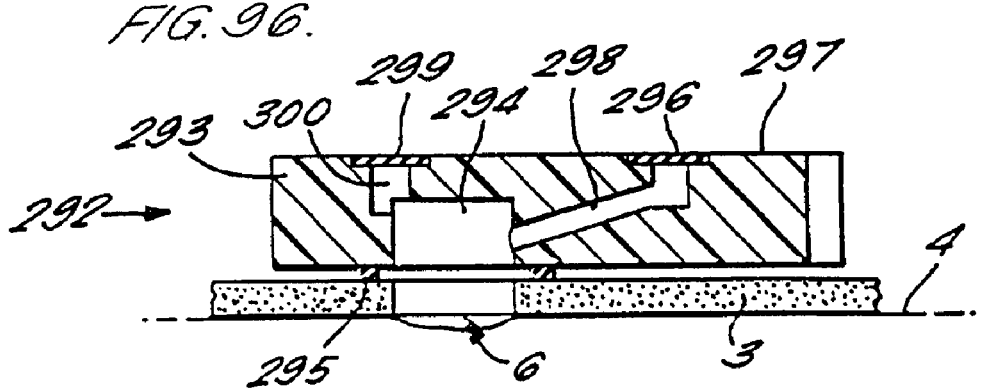
FIG. 96 is a schematic sectioned elevation of a transdermal perfusion device including the movable portion of FIG. 95.

A transdermal delivery device 292 is shown partially in FIG. 96, omitted detail corresponding to that described above with reference to FIGS. 34 to 68 for example, and having a base 3 defining an aperture 6 through which a de-epithelialised skin site is prepared by forming and opening a suction blister as described above.

The base 3 is secured adhesively to skin 4 of a patient.

The transdermal delivery device 292 has a movable portion 293 which has an access port 7 through which, in a first position of the movable portion relative to the base 3, the skin site is prepared and which, when moved into a second position as shown in FIG. 96, overlays the aperture 6 and defines an opening 294 communicating with the aperture and peripherally sealed by means of an O-ring seal 295.

A first penetrable septum 296 is located so as to be flush with an upper surface 297 of the movable portion 293 with a duct 298 extending between the first septum and the opening 294 whereby fluid may be introduced by penetration of the first septum in order to access the opening 294.

A second septum 299 is similarly provided and communicates via a second duct 300 with the opening 294 to allow suction to be applied by penetrating the second septum to thereby draw fluid into the opening.

Figure 97:
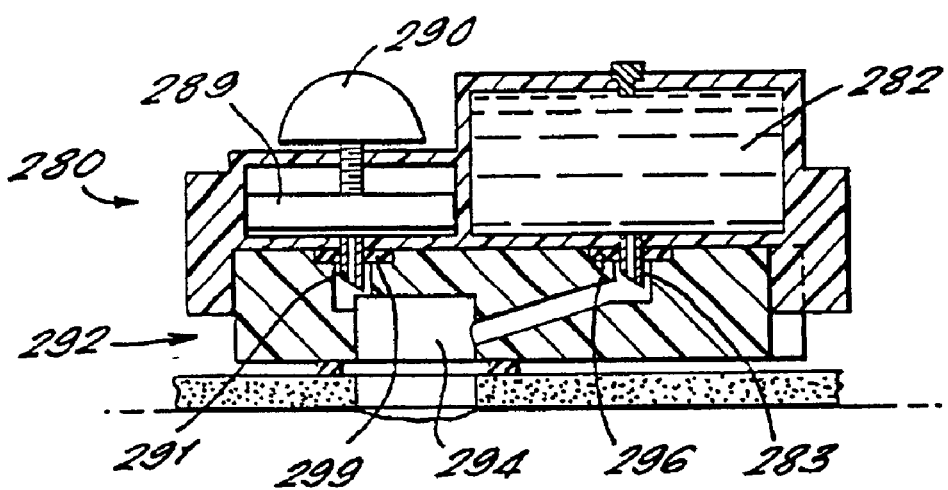
FIG. 97 is a schematic sectioned elevation of the implementing device of FIGS. 93 and 94 when fitted to the movable portion of FIGS. 95 and 96.
Figure 98:
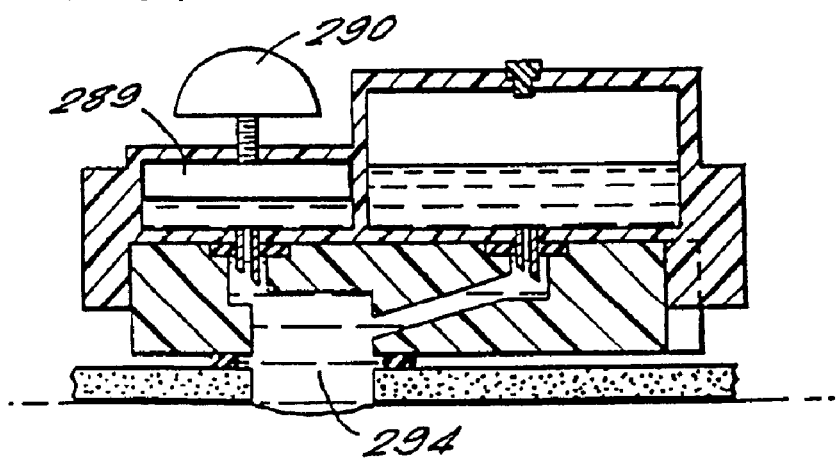
FIG. 98 is a schematic sectioned elevation of the apparatus of FIG. 97 following actuation of a suction means to draw fluid from a reservoir.

In FIG. 97, the implementing device is shown connected to the movable portion 293 with the first and second cannulas 283, 291 penetrating the first and second septums 296 and 299 respectively. FIG. 98 illustrates the manner in which fluid within the fluid receiving chamber 282 can be caused to flow into the opening in order to deliver fluid in contact with the de-epithelialised dermis, the actuator 290 having been retracted to raise the piston 289 thereby creating suction at the opening 294.

Liquid contained in the reservoir may thereby deliver transdermally and typically will comprise aqueous solution of a drug. During prolonged delivery, the actuator 290 may be progressively retracted in order to refresh the liquid contained in the opening 294 with further liquid drawn from the reservoir thereby maintaining a required concentration.

The implementing device 280 may be disconnected from the movable portion 293 simply by pulling them apart and if required, a further implementing device may be substituted. In this way, fresh doses of the drug may be administered or the drug may be varied either in concentration or in composition simply by interchanging implementing devices in which appropriate drugs are contained in the respective reservoirs. Alternatively, different types of implementing device as discussed above may be substituted for purposes other than the delivery of drugs.

The apparatus of FIGS. 93 to 98 may be modified to include a reservoir in which the walls of the fluid receiving chamber 283 are collapsible.

A further alternative device 301 will now be described with reference to FIGS. 99 to 111 using corresponding reference numerals to previous Figures where appropriate for corresponding elements.

Figure 101:
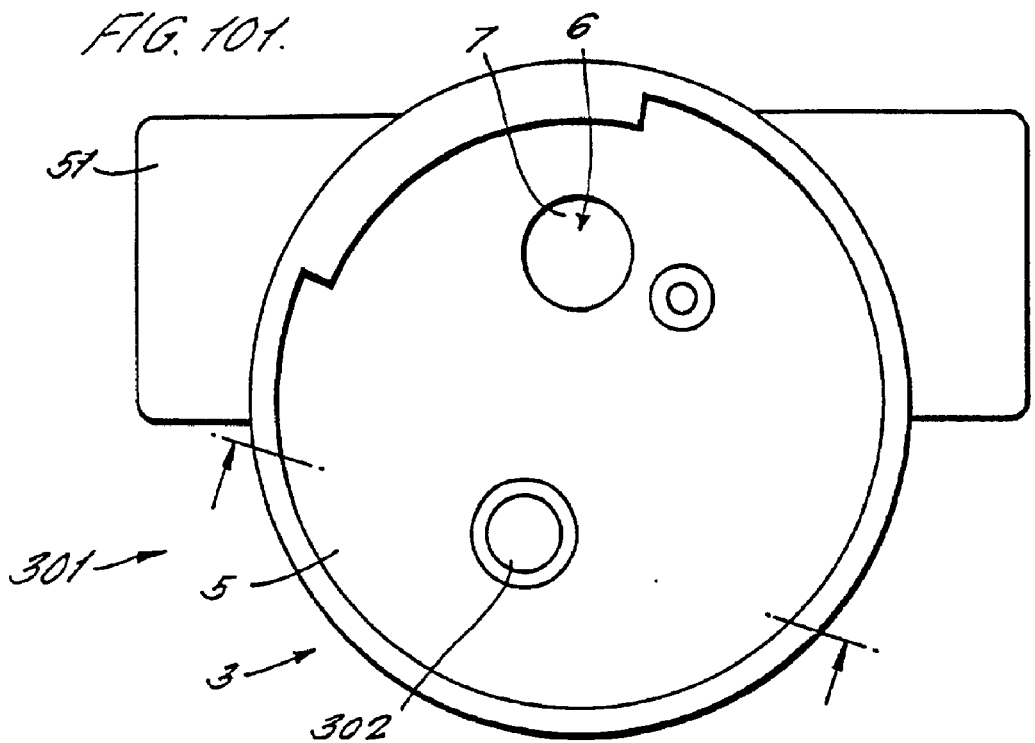
FIG. 101 is a schematic plan view of the device of FIGS. 99 and 100.

The alternative device 301 shown in plan view in FIG. 101 differs from the device 1 of FIGS. 34 to 52 in the construction of the rotatable portion 5 but otherwise functions in the same way to apply suction to the skin, to form a suction blister and to remove the epithelial roof of the blister to thereby define a de-epithelialised erosion at the treatment site. In the FIGS. 99 to 111 the device 301 in its various stages of operation is illustrated after the stage of forming the de-epithelialised erosion and removal from the device of the suction tube 15 with its associated components illustrated in FIG. 38.

Figure 99:
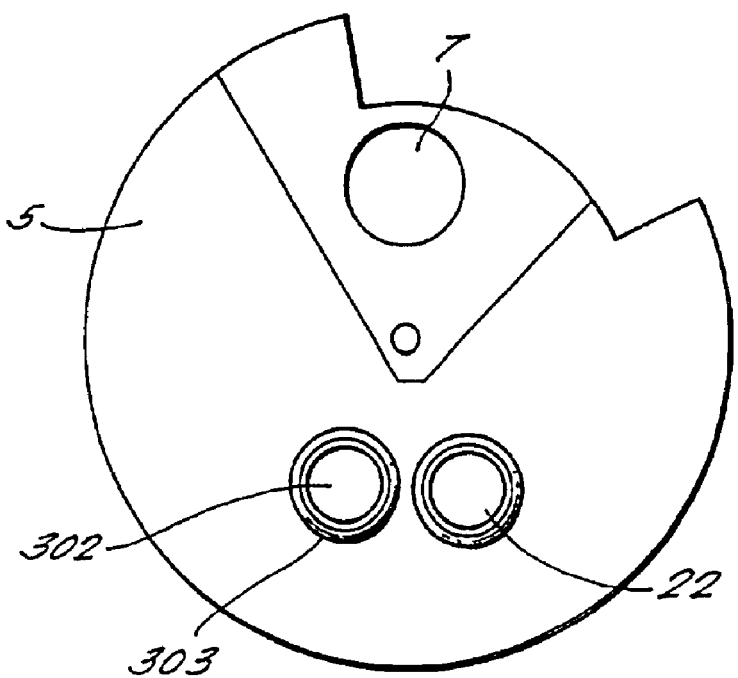
FIG. 99 is an underneath plan view of a rotatable portion of an alternative device, the rotatable portion being cooperable with a base of the type shown in FIG. 40 and an actuating ring of the type shown in FIG. 46.
Figure 100:
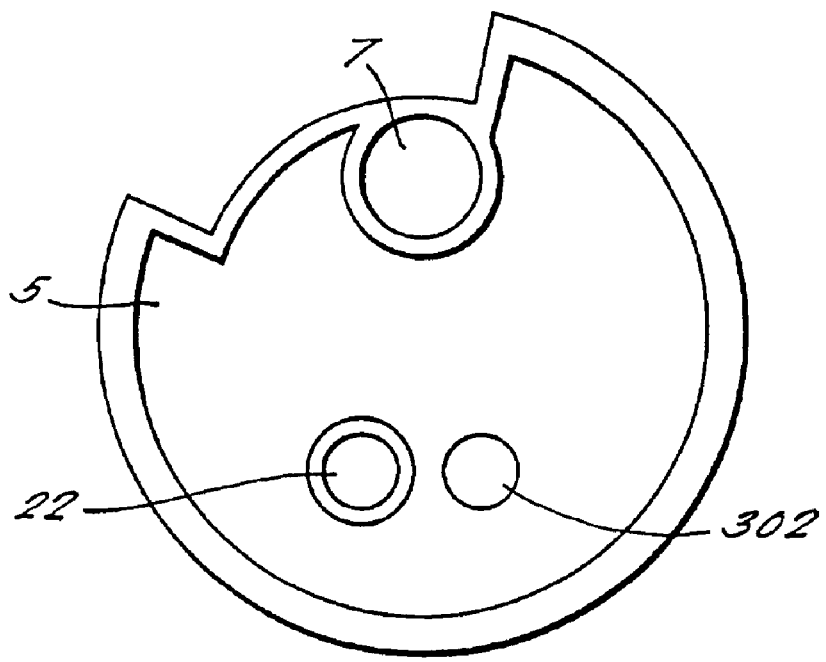
FIG. 100 is a plan view of the rotatable portion of FIG. 99 with the cover plate removed.

The device 301 includes a drug delivery reservoir having an outlet port 22 as shown in the underneath view of FIG. 99 and, formed in a separate compartment of the rotatable portion adjacent to the reservoir outlet port, a sampling port 302. By rotation of the rotatable portion 5 either the reservoir outlet port 22 or the sampling port 302 may be brought into registration with the base aperture 6 to access the de-epithelialised skin erosion so that the device 301 may be used either for drug delivery or sampling respectively.

As shown in FIG. 99 the reservoir outlet port 22 is provided with an O-ring seal 24 and the sampling port 302 is provided with an O-ring seal 303. As shown in FIG. 102, the O-ring seal 303 is operable between the upper surface 23 of the base 3 and the underneath surface 304 of the rotatable portion 5, the O-ring seal being captively retained relative to the rotatable portion by a locating groove so as to be rotatable in registration with the sampling port 302.

Figure 103:
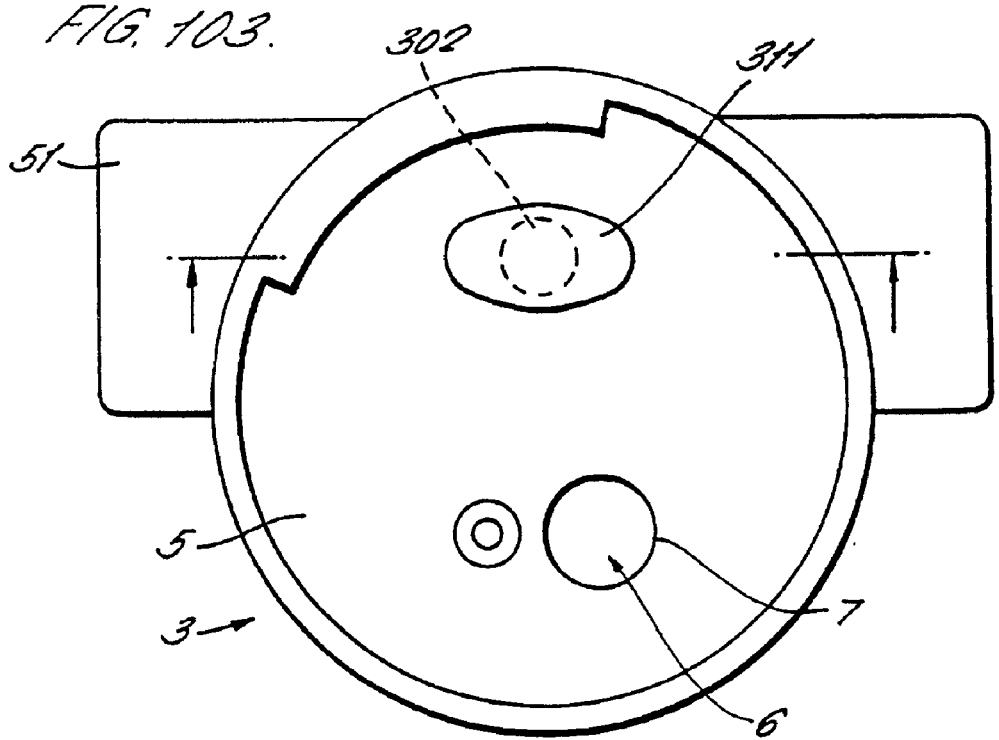
FIG. 103 is a plan view of the device of FIGS. 99 to 102 showing the rotatable portion moved into a position where the sampling port is in use.

As shown in FIG. 103, the rotatable portion 5 may be rotated into a position in which the sampling port 302 overlays the de-epithelialised erosion 305 in order to sample exudate generated at the skin erosion 305 from the exposed dermis. In this configuration, as shown in FIG. 104, an air tight seal continues to be maintained between the base 3 and the skin 4 by means of an adhesive layer 306 which thereby provides an air tight seal. The O-ring seal 303 maintains this air tight seal between the base 3 and the rotatable portion 5 so that the sampling port 302 defines a cylindrical sampling chamber 307 into which exudate including plasma filtrate may fill.

A screw fitting 308 is mounted on the rotatable portion 5 at the upper entrance to the sampling chamber 307 thereby enabling a screw threaded sampling piston 309 to be inserted into the sampling chamber and advanced or retracted to any desired axial position thereby enabling the volume of the sampling chamber 307 to be variable. In FIG. 104 the sampling piston 309 is shown in a fully advanced position in which the head of the piston is advanced into close proximity with the erosion 305 and volume of the sampling chamber 307 is thereby minimised. To initiate a sampling procedure, the sampling piston 309 is initially inserted into the sampling port 309 and advanced into the fully advanced position as shown in FIG. 104. The sampling piston 309 includes an axially extending bore 310 allowing air trapped within the sampling chamber 307 to freely escape during the advancement of the sampling piston into the fully advanced position thereby avoiding any excess pressure in the sampling chamber which might otherwise have the undesirable effect of causing separation of the base 3 from the skin by disruption of the adhesive layer 306.

An occlusive cap 311 is then screw fitted to the outer end portion 312 of the sampling piston so as to close the bore 310 and constituting an openable closure. The piston 310 is then retracted by screw action to a fully retracted position as shown in FIG. 105 thereby creating a partial vacuum in the sampling chamber 307, typically in the range 100 to 200 millimeters of mercury below atmospheric pressure.

This position is maintained for a period of approximately 15 minutes during which time exudate accumulates in the sampling chamber 307. The rate of production of exudate is enhanced by the partial vacuum created in the sampling chamber, the transdermal convective movement of liquid and entrained molecules from the plasma of the patient to the surface of the erosion being increased several fold. During this process, the intact semi-permeable capillary membrane of the dermis acts as a sieve to prevent significant contamination of the exudate liquid volume with red and white blood cells.

Figure 108:
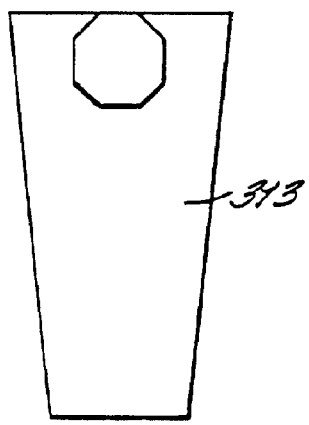
FIG. 108 is a side elevation of the cuvette of FIG. 107.
Figure 107:
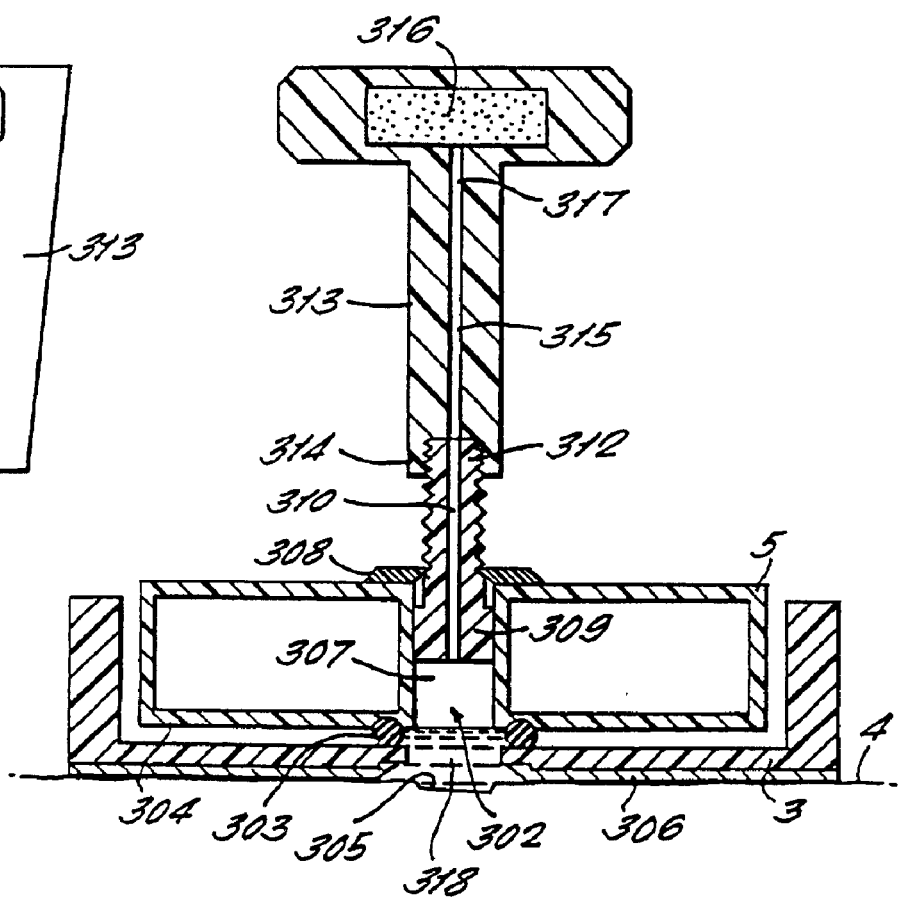
FIG. 107 is a sectional elevation of the device of FIGS. 99 to 106 after fitting of a cuvette to the sampling piston.

The occlusive cap 311 is then released from its screw fitting with the piston 309 and detached, thereby allowing air to enter the bore 310 and equalise pressure within the sampling chamber 307 with atmospheric pressure. A cuvette 313 as shown in FIGS. 107 and 108 is then fitted to the outer end portion 312 of the sampling piston 309 by means of a screw fitting 314 as shown in FIG. 107, the cuvette defining a capillary slot 315 which when fitted to the piston lies in communication with the bore 310, the cuvette being formed of a transparent plastics material and having an absorbent pad 316 arranged to provide an air vent to an upper end 317 of the slot 315.

Figure 109:
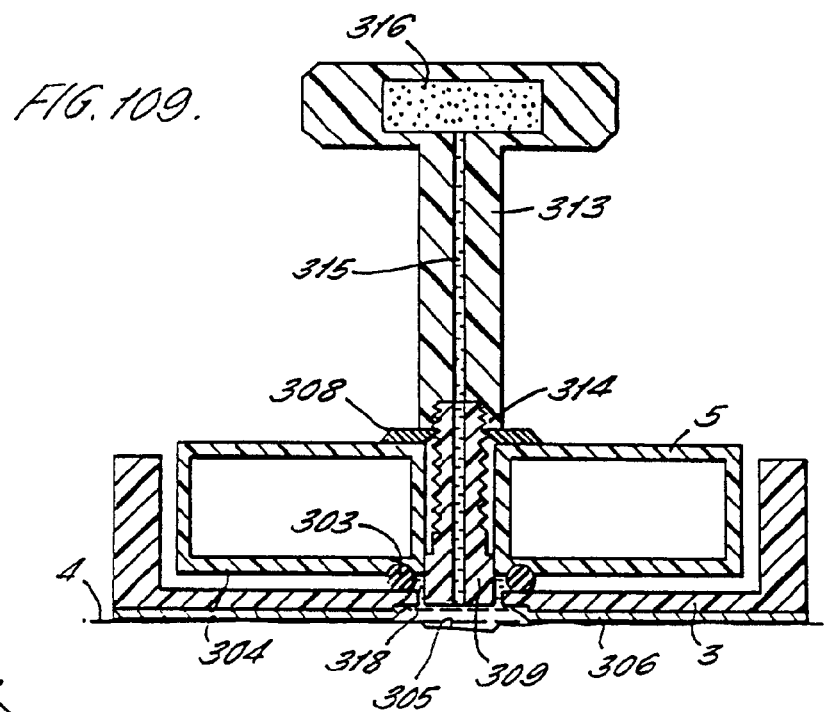
FIG. 109 is a sectional elevation showing the device of FIG. 107 with the sampling piston fully advanced.

As shown in FIG. 109 the sampling piston 309 may then be advanced into the sampling chamber 307 so as to displace the exudate 318 from the sampling chamber 307 into the cuvette 313 so as to fill the slot 315, excess exudate being absorbed by the pad 316.

Figure 111:
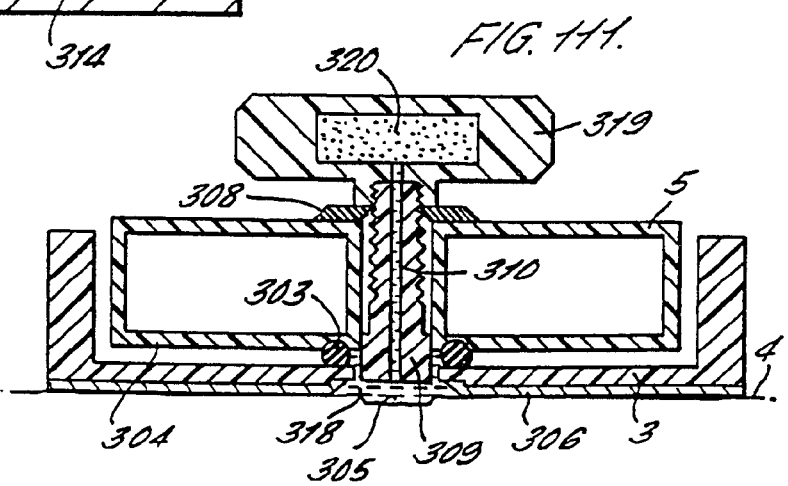
FIG. 111 is a sectional elevation of the device of FIGS. 99 to 110 in which a capillary active plug is fitted to the sampling piston.

The cuvette 313 may then be detached by reverse screw action from the sampling piston 309 and replaced by a plug 319 as shown in FIG. 111 which is attachable by screw action to the sampling piston and includes a pad 320 of capillary active material for venting the sampling chamber to ambient air and collecting exudate continuing to emanate from the erosion 305 and collected via the bore 310.

Figure 110:
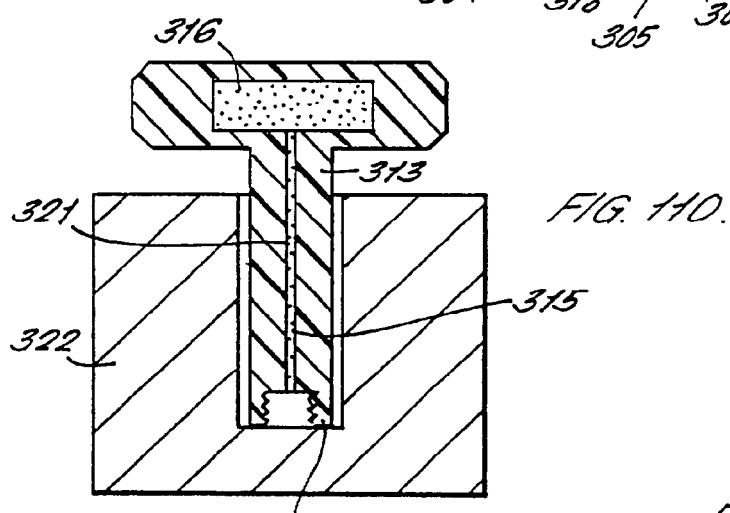
FIG. 110 is a sectional elevation of the cuvette of FIGS. 107 to 109 after removal from the device and insertion into a photometer.

The cuvette 313 containing a sample 321 of the exudate as shown in FIG. 110 may then be inserted into an analysing apparatus 322 such as a photometer.

The cuvette also contains a reagent located on a sidewall of the slot 315 and selected to perform a chemical test on the sample. A range of reagents may be included in a single cuvette. The analysing apparatus may therefore be set up to respond to optically detectable changes in the reagent.

The alternative device 301 may also be used for the delivery of a drug to the erosion 305 by rotation of the rotatable portion 5 so as to bring the outlet port 22 of a drug reservoir within the rotatable portion into registration with aperture 6 formed in the base 3 in a manner corresponding to the arrangement described above with reference to FIG. 36.

The alternative device may include other forms of openable closure, such as a valve mechanism.

The alternative device 301 may be provided with a skin heating element as described above with reference to FIG. 55, the effect of heating being to enhance rates of sampling and delivery.

Figure 112:
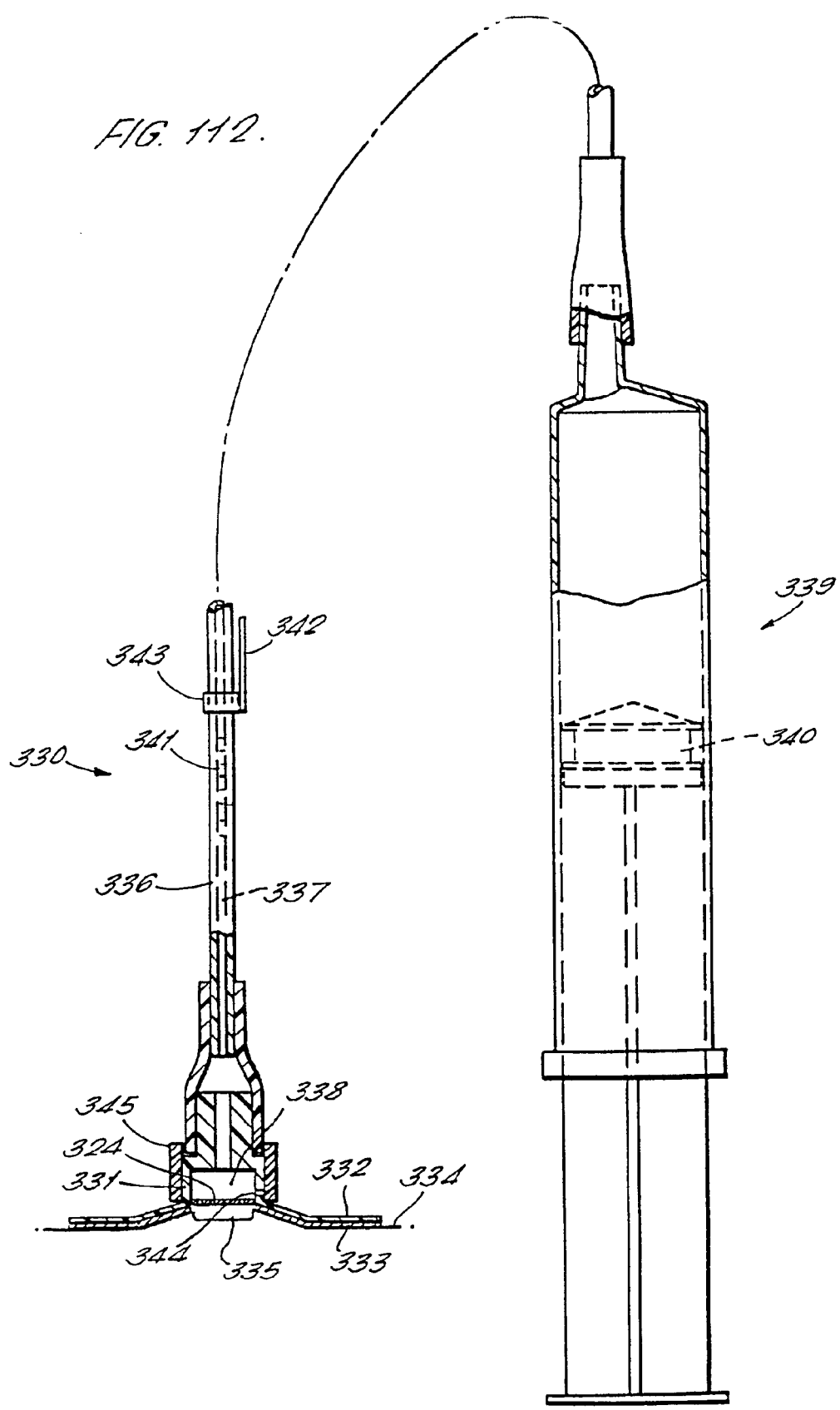
FIG. 112 is a part sectioned elevation of a further alternative sampling device for use in sampling exudate from a de-epithelialised skin site.
Figure 113:
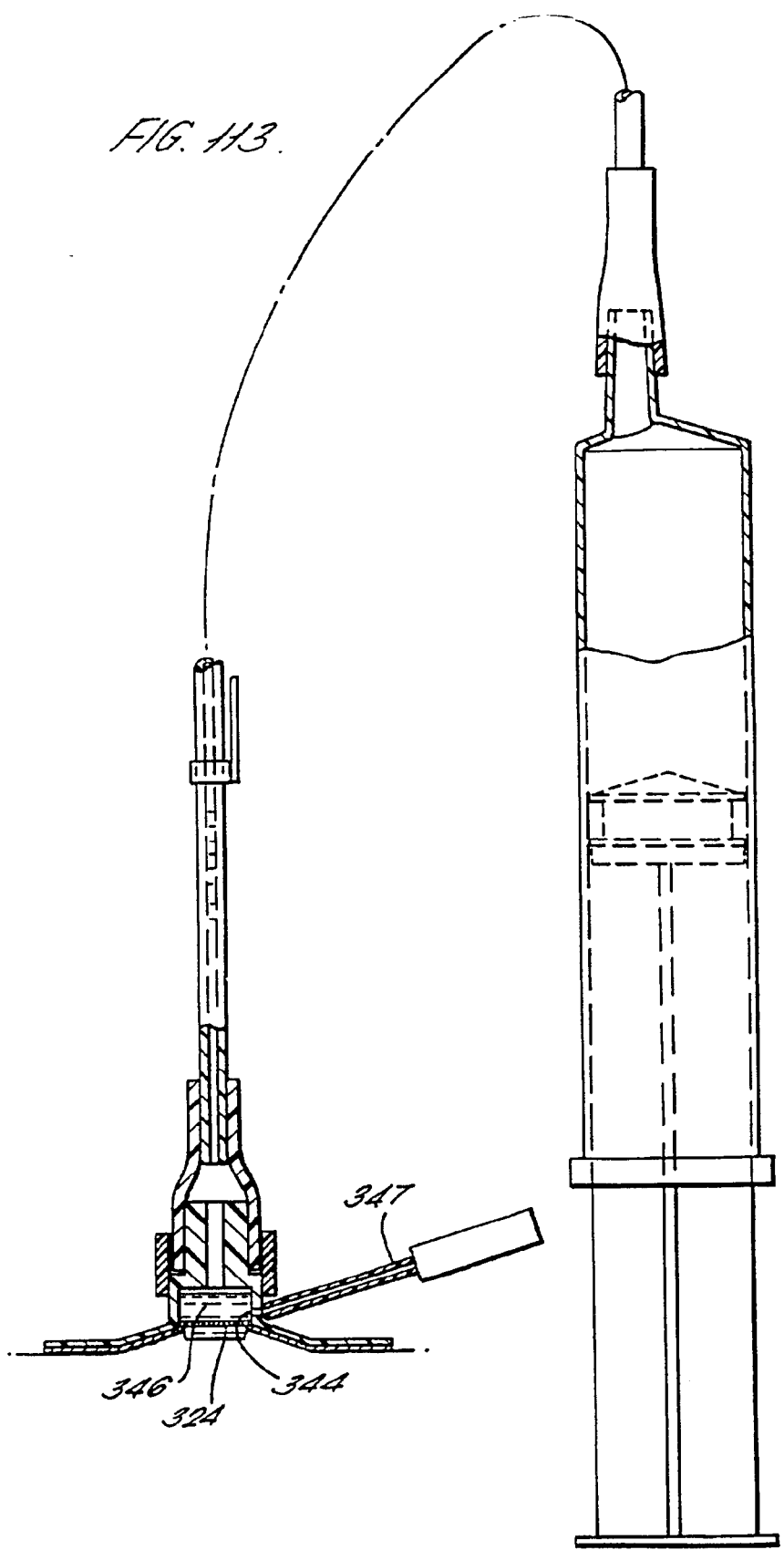
FIG. 113 is a part sectioned elevation of the device of FIG. 112 showing the extraction of the sample using a cuvette.

The sampling of exudate may alternatively be undertaken using a separate sampling device 330 as shown in FIGS. 112 and 113. The sampling device 330 comprises a cylindrical suction cup 331 forming part of an enclosure having a partially flared peripheral annular flange 332 having an adhesive layer 333 which in use is presented to the skin 334 of a patient at a location symmetrically surrounding a de-epithelialised skin erosion 335, the erosion having been formed by any convenient method, but preferably using a suction blister forming device of the type described above for example with reference to FIG. 34. The suction cup 331 is provided with an entrance grid 324 or sieve to prevent the intrusion of tissue at the erosion. (The grid 324 may optionally be omitted).

A capillary tube 336 is connected to the suction cup 331 and defines a capillary bore 337 communicating with a suction chamber 338 defined by the suction cup.

The capillary tube 336 is connected to a syringe 339 operable to create a partial vacuum in the suction chamber 338 by retraction of a piston 340, the syringe 339 being lockable at any position along its stroke so as to maintain any required level of partial vacuum.

A slug of liquid 341 is located in the bore 337 adjacent to a scale 342 attached to the tube 336 by a clamp 343 and arranged so as to extend along the length of the bore.

The scale 342 and the slug of liquid 341 thereby together comprise an indicator responsive to the volume of air displaced along the bore between the chamber and the syringe.

A side hole 344 is formed in the suction cup 331 at a location adjacent to the flange 332 and is normally closed by a resilient sleeve 345 which externally overlays a cylindrical side wall portion of the suction cup.

In use, the flange is adhered to the skin as shown in FIG. 112 such that the erosion 335 is open to the air within the suction chamber 338 and the piston 340 is retracted within the syringe 339 to create a partial vacuum within the suction chamber. The creation of this partial vacuum is accompanied by displacement of air from the chamber through the bore 337 thereby causing the slug of liquid to move in a direction away from the suction cup. After a short period in which a relatively high level of partial vacuum is applied to the suction chamber 338 in order to remove any pockets of air lodged between the adhesive layer and the skin adjacent to the suction chamber, the piston is partially returned to an intermediate position at which a lower level of partial vacuum is applied to the suction chamber 338. The position of the clamp 343 is adjusted that a zero of the scale 342 coincides with the location of the slug of liquid 341. This level of partial vacuum is maintained for a period sufficient to accumulate exudate 346 within the suction chamber 338 as shown in FIG. 113, the rate of transdermal production of exudate being enhanced by the presence of the partial vacuum such that typically a period of 30 minutes is sufficient to accumulate a volume of 100 to 300 microliters using a partial vacuum of 200 mm mercury below atmospheric pressure.

Accumulation of exudate within the suction chamber 338 is accompanied by progressive movement of the slug of liquid 341 as air is displaced from the suction chamber 338. The indicator comprising the scale 342 may therefore be used to sense completion of the exudate collection phase. At the end of this phase, the piston 340 is returned to its rest position so that suction is no longer applied in the suction chamber 338.

A sample of exudate may then be taken by displacing the sleeve 345 as shown in FIG. 113 to expose the outlet of the side hole 344, a microcuvette 347 for example then being used to draw exudate through the side hole by capillary action. The microcuvette 347 in this example consists of a transparent plastic slide having a capillary slot into which exudate liquid is drawn. The microcuvette 347 is then inserted into an analyser such as a photometer in order to perform immediate analysis of the exudate.

The sampling device 330 thereby provides a means of taking a sample of exudate from an erosion created by a de-epithelialising method, the sampling device being operable to enhance the rate at which exudate is collected by applying a partial vacuum over the erosion. This partial vacuum promotes a convection process by which exudate flows transdermally in response to a pressure differential through the semi-permeable membrane constituted by the exposed dermis. Moreover the dermis constitutes a sieve allowing plasma to pass and retaining blood cells. Relatively large molecules such as sugar and insulin are able to pass through the dermis thereby making it possible to perform analysis on the concentration of such constituents of the exudate as might for example be required in the treatment of diabetes.

The sampling device 330 may be modified to include alternative indicators such as those described above with reference to FIGS. 59, 90, 91 and 92. The sampling device 330 may be further modified by creating a partial vacuum using a modified syringe having a screw threaded piston adjustor to allow continuous axial adjustment of the piston position or alternatively by the use of a micropump.

Throughout the description and claims the term perfusion should be understood to encompass both the partial and complete diffusion of a fluid through body tissue i.e. including the partial diffusion of a fluid in which certain molecules contained in the fluid are diffused through tissue leaving a residue of undiffused fluid.

What is claimed is:

1. A method of transdermal administration of fluids through the skin of a human or animal body, comprising the steps of:
    attaching a housing to the body such that a contact surface of the housing is held in contact with a portion of skin by an adhesive layer, the housing defining a chamber and the contact surface defining an aperture communicating with the chamber;
    applying suction to the skin at a treatment site which is accessible via the aperture until an area of the skin's epidermis at the treatment site is detached from the skin's underlying dermis;
    disrupting the detached area of epidermis such that the dermis is exposed within the chamber; and
    supplying fluid to the chamber such that the fluid may be absorbed by the dermis without intervention of the epidermis.

* * * * *